(12) United States Patent
Bertozzi et al.

(10) Patent No.: US 6,974,580 B2
(45) Date of Patent: Dec. 13, 2005

(54) MYCOBACTERIAL SULFATION PATHWAY PROTEINS AND METHODS OF USE THEREOF

(75) Inventors: Carolyn R. Bertozzi, Berkeley, CA (US); Spencer J. Williams, Berkeley, CA (US); Joseph D. Mougous, El Cerrito, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/891,383

(22) Filed: Jul. 13, 2004

(65) Prior Publication Data

US 2004/0249131 A1 Dec. 9, 2004

Related U.S. Application Data

(60) Division of application No. 10/286,606, filed on Oct. 31, 2002, now Pat. No. 6,863,895, which is a continuation-in-part of application No. 10/126,279, filed on Apr. 19, 2002, now Pat. No. 6,858,213.

(60) Provisional application No. 60/285,394, filed on Apr. 20, 2001, and provisional application No. 60/345,953, filed on Oct. 26, 2001.

(51) Int. Cl.[7] .................. A61K 39/04; A61K 39/02; A61K 39/00
(52) U.S. Cl. ................ 424/248.1; 424/9.1; 424/9.2; 424/130.1; 424/164.1; 424/168.1; 424/180.1; 424/200.1; 424/234.1; 435/4; 435/7.1; 435/7.4; 435/15; 435/29; 435/183; 435/440; 435/471
(58) Field of Search ................ 424/9.1, 9.2, 130.1, 424/164.1, 168.1, 180.1, 200.1, 234.1, 248.1; 435/4, 7.1, 7.4, 15, 29, 183, 193, 440, 471

(56) References Cited

U.S. PATENT DOCUMENTS 6,046,002 A 4/2000 Davis et al.

OTHER PUBLICATIONS

Bloom, et al. *Science*, (1999) vol. 257: 105–1064.
Bronzna, et al. *Infect. Immun.*, (1991) vol. 59: 2542–2548.
Cole, et al. *Nature*, (1998) vol. 393: 537–544.
Daffe, et al. *Adv. Microb. Physiol.*, (1998) vol. 39: 149–152.
Goren, et al. *Proc. Natl. Acad. Sci. USA*, (1976) vol. 73: 2510–2514.
Hemmerich, et al. *Glycobiol.*, (2000) vol. 10: 848–856.
Khoo, et al. *J. Biol. Chem.*, (1999) vol. 274: 9778–9785.
Lopez Marin, et al. *Biochem.*, (1992) vol. 31: 11106–11111.
Pabst, et al. *J. Immunol.*, (1988) vol. 140: 634–640.
Tsukamara, et al. *Microbiol. Immunol.*, (1981) vol. 25: 215.
Zhang, et al. *J. Immunol.*, (1991) vol. 146: 2730–2736.
Gavel et al., ATP Sulfurylases from Sulfate–Reducing Bacteria of the Genus Desulfovibrio. A Novel Metalloprotein Containing Cobalt and Zinc. Biochemistry Oct. 26, 1998, vol. 37, pp. 16225–16232.
Abola et al. Reduction of Adenosine-5' Phosphosulfate Instead of 3' Phosphoadenosine-5' Phosphosulfate in Cyteine Biosynthesis by Rhizobium Meliloti and other Members of the Family Rhizobiaceae.

*Primary Examiner*—Rodney P Swartz
(74) *Attorney, Agent, or Firm*—Paula A. Borden; Bozicevic, Field & Francis, LLP

(57) ABSTRACT

Novel mycobacterial sulfation pathway proteins and polypeptides related thereto, as well as nucleic acid compositions encoding the same, are provided. The subject polypeptide and nucleic acid compositions find use in a variety of applications, including research, diagnostic, and therapeutic agent screening applications. Also provided are methods of inhibiting growth and/or virulence of a pathogenic mycobacterium, and methods of treating disease conditions associated with a pathogenic mycobacterium, particularly by administering an inhibitor of a mycobacterial sulfation pathway protein. The present invention further provides genetically modified mycobacteria having a defect in a sulfation pathway enzyme gene; and immunogenic compositions that include such genetically modified mycobacteria.

13 Claims, 27 Drawing Sheets

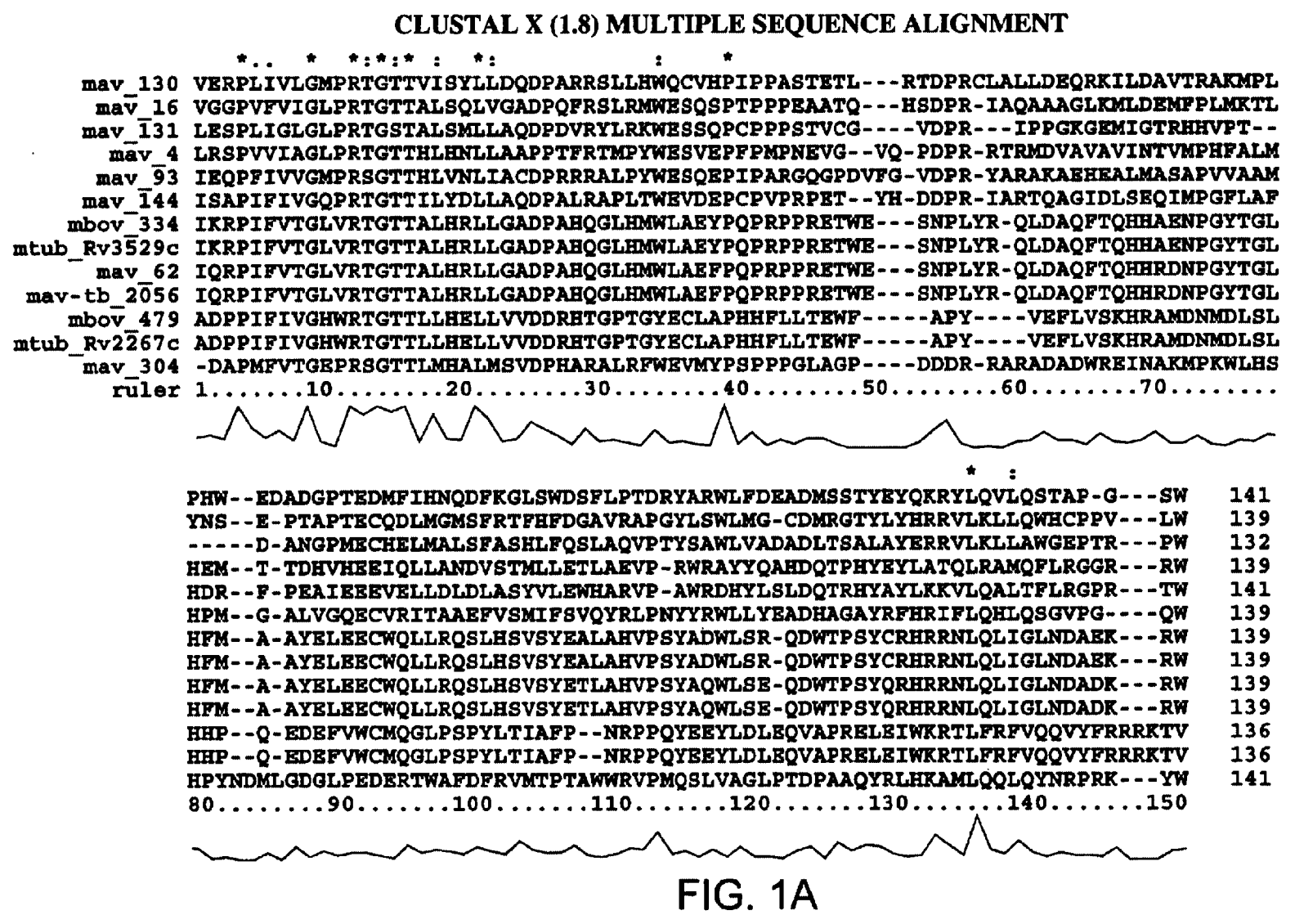

CLUSTAL X (1.8) MULTIPLE SEQUENCE ALIGNMENT

```
                  *   *:*:*  :  *:                                                *
     mav_130   VERPLIVLGMPRTGTTVISYLLDQDPARRSLLHWQCVHPIPPASTETL---RTDPRCLALLDEQRKILDAVTRAKMPL
      mav_16   VGGPVFVIGLPRTGTTALSQLVGADPQFRSLRMWESQSPTPPEAATQ---HSDPR-IAQAAAGLKML

```
                       **   *          *    *   *:*::   .  *
mav_130       SLKMPSHSVHIEALLKVFPDARLIWAHRDPYKATGSLCNLWRLPQSLVMNTELLDQTEMGRLAMWQMRYHVDRPLRARER    288
mav_16        HLKTPVHDMFALDALVEAYPDAKFLWSHRDPAKVMASVCSLIQYVRSWSS--DRNDPHELGREQVDSWVEGVRRAMDFRRR    284
mav_131       RLKCPSHVLWLDRLAAVFPDAKFVMTHRDPTDVILSVADLYADIIGQFT--DDIDRPYIGRLNVEHWSLGMARTLQFRAA    277
mav_4         LLKSPQHLEQVPVLDRVFPDSIVVFTHRDPVPVALSMIAMITYSARMHR--SPVPVRQIAESWIDRLGQMLAALVRDRDV    284
mav_93        VLKSPQHCEQLGPLMATFPDATIAFTHRDPVAVIQSAITMMAYSDRLRR--TSIDPQWLLDYWSDRVERLLSACVRDRDL    287
mav_144       LLKSPAHLWQLDALLAEYPDALIVQTHRDPLNVISSIAALTHELRGMCSDESSITECAAQSYEEIVVGLDREMALRDRGA    285
mbov_334      VLKNPSHLFALDALMATYPDALVVQTHRPVETIMASMCSLAQHTTEGWS--TKFVGAQIGADAMDTWSRGLERFNAARAK    285
mtub_Rv3529c  VLKNPSHLFALDALMATYPDALVVQTHRPVETIMASMCSLAQHTTEGWS--TKFVGAQIGADAMDTWSRGLERFNAARAK    285
mav_62        VLKNPSHLFALDALMATYPDALVIQTHRPVETIMASMCSLAQHTABGWS--TTFVGAQIGADAMDTWSRGLERFNTARAK    285
mav-tb_2056   VLKNPSHLFALDALMATYPDALVIQTHRPVETIIGVDVLAGPAHREGWS--TTFVGAQIGADALMNTWSRGLERFNTARG-    228
mbov_479      ILKNPTHSFRIKVLLEVFPQAKFIHIVRDPYVVYPSTIHLEKALYRIHG-LQQPTFDGLDDKVVSTYVDLYRKLDEGREL    282
mtub_Rv2267c  ILKNPTHSFRIKVLLEVFPQAKFIHIVRDPYVVYPSTIHLEKALYRIHG-LQQPTFDGLDDKVVSTYVDLYRKLDEGREL    282
mav_304       VLKG-FHGFRLKELFDTYPDARMVWLHRDPVQVAASRTMMMADIAEGMVG--PVDLHAEAKHLEMTRASIANTMTN-PL    287
ruler         .....160.......170.......180.......190.......200.......210.......220.......230

IGDERFFFHMYYHEMMRDPMDVMRRIYEWADEPLTAEFTEARMRNWLAHHFPQDRFALNAY--RLD-EYGLTV                288
NGDERFADVSFADLQTDPVGTLRASYQSLGLDFTDDTLHAVTQWARTERPGSRGHHDY--DLA-DYGLTP                   284
GNDNRFYDIDFRAMQADPIGEVTGLYRWLGEQVSDEFEGRMNSWWAQAATEREPSSHA--DPV-QFGIDL                   277
IGPDRSIDIRFDDFMADELGVAERVYALADEPFTDDARAAVADYLAGHRRGRLGNVET--SYE-MFGLDE                   284
VAPERSVDISFHQLSGNEIPVIERLYERGGVELPQRVRDRFQRYLDGNPRGKHGRIRY--QLQRHFGISA                   287
VPPGRVIDVRYADFMKDFMPWTTIKDIYERLDRELRPDABQRMREFLASHP-SDGGRSRY--TWS-DTGLDA                 285
YDSAQFYDVDYHDLIADPLGTVADIYRHFGLTLSDEARQAMTTVHAESQSGARAPKHS--YSLADYGLTV                   285
YDSAQFYDVDYHDLIADPLGTVADIYRHFGLTLSDEARQAMTTVHAESQSGARAPKHS--YSLADYGLTV                   285
YNPAQFYDVDYKELIADPLGTVADIYRHFGLTLTEEAKAAMAKTHADSQSGERAPKHS--YSLADYGLSV                   285
------------------------------------------------------QVQPGAVLRRR------------L         228
VDPTRFYELRYEDLIGDPEGLRRLYQHLGLGDFECYLPRLRQYLADHADYKTNSYQL--TVEQR-AIVD                    282
VDPTRFYELRYEDLIGDPEGLRRLYQHLGLGDFECYLPRLRQYLADHADYKTNSYQL--TVEQR-AIVD                    282
VDDPRILHLSYTDFIADHVGAVRRYYAFCGRELTAEAESAMRAYLADNPGDRYGKFRYSTQLLTDIGEDL                   287
.....240.......250.......260.......270.......280.......290.......300
```

FIG. 1B

```
mav_130        EALQPIFAEY-LDTFDIELEGRP----------     310
mav_16         EGVRERFADY-LAVYDATA--------------     302
mav_131        DSIRPLFADY-ITAAADWTAHADI---------     300
mav_4          DSLRERFAPY-VERFLA----------------     300
mav_93         DELRARFGFY-FDKFDVRPE-------------     306
mav_144        GAVRERVRAY-QDRYGVPTEALR----------     307
mbov_334       EMVKERFAGL-----------------------     295
mtub_Rv3529c   EMVKERFAGL-----------------------     295
mav_62         ETVKERFAGL-----------------------     295
mav-tb_2056    QGVDRRPAG------------------------     237
mbov_479       EHWGEIIDRYGYDRHTPEPARLRPAVGG-----     310
mtub_Rv2267c   EHWGEIIDRYGYDRHTPEPARLRPAVGG-----     310
mav_304        DALHAEFRPF-RERFGVPIENRG----------     309
       ruler   ........310........320..........
```

Rv2267c (SEQ ID NO:23)

atgaaggctctccgttcgtcgtctcgactttcccggtggcgcgagtgggccgcaccgctgtgggtcggctg
caacttctcggcctggatgcggcttttgatccgtaaccgcttcgccgtgcatcacagccgctggcacttcg
cggtcctctatacgtttctcagcatggtcaattcctgtctgggggttgtggcagaagatcgttttcggtagg
cgagtggccgaaacggtgatcgccgatccgccaatcttcattgttgggcattggcgtaccggcaccacctt
gctgcatgaactgttggtcgtcgatgatcgccacaccggtcccaccggctacgaatgccttgcgccacacc
attttctactgaccgagtggtttgcgccatatgtggaattcctggtatcgaagcatcgggcaatggacaac
atggatttgagcttgcatcacccgcaggaagacgagttcgtgtggtgtatgcagggcctgccgtcgccgta
tctgaccatcgcattcccgaaccggccgccccagtatgaggagtacctggatctagagcaggtggcaccgc
gagaactagaaatctggaaacggaccctgttccggttcgttcagcaggtgtacttccgccgtcgcaagacg
gtgatcctcaagaatccaacgcatagtttttcgaatcaaggtgctgctggaggtattcccgcaagcgaagtt
catccacatcgtccgagatccctatgtggtctatccatcaaccatccatcttcataaggcgctgtaccgca
tacatggcttgcaacaaccgacgttcgacgggttggacgacaaggtcgtgtcgacctacgtcgacctatac
cgaaagttggacgaaggccgagaactcgttgaccccacacgcttttacgaattgcgttatgaggatttgat
cggtgatcccgagggacagctgcgccggctataccagcacctgggactgggcgacttcgagtgttacctgc
cgcgtctgcggcaatacctagctgaccatgcggactacaaaaccaacagctatcaactgaccgtcgagcag
cgtgcgattgtcgatgagcactggggcgagatcatcgaccgctacggctacgatcgtcacacacctgagcc
ggcacgtcttcggcctgcggttggcggc

FIG. 4

Rv3529c (SEQ ID NO:15)

atgactcggcgtcccgatcggaaagatgtggccaccgtcgacgaactgcacgcatcggctaccaaactggt
gggtctcgacgattttggcaccgacgacgacaactaccgtgaggcgctgggtgtgttgctggacgcttacc
agggcgaagccggcctcaccgtgttgggcagcaagatgaaccggttcttcctgcgcggtgcgctggtggcc
aggctactgtcccagtccgcgtggaagcagtatccggagcacgtcgacgttgccatcaaacggcctatctt
cgtcaccgggttggtgcgcaccggaaccactgcgctgcaccggctgctgggcgccgacccggcccaccaag
gcctgcacatgtggctggccgagtaccgcagccgcgcccccgcgcgagacctgggagtcaaacccgttg
tatcgccagctcgatgcacagttcacccagcatcatgccgagaatccgggatacaccggcttgcatttcat
ggcggcctacgagttggaggagtgttggcagctgttgcggcagtcgctgcattcggtgtcgtacgaggcgc
tggcgcatgtacccagctatgccgactggttgtcacgccaggactggacgccgtcgtattgccggcaccgc
cgcaacctgcagctgattgggctcaacgatgccgaaaagcggtgggtactaaagaatccgagtcatctatt
tgccctggatgcgctgatggcgacctatcccgatgccctggtggtgcagactcaccggccggtggagacga
tcatggcgtcgatgtgctcgctggcgcagcacaccacagaagggtggtcgacgaagtttgtgggcgcccag
atcggtgcggacgcgatggacacctggtcgcgtgggctggagcggttcaatgccgcacgggccaaatatga
ttcggcccagttctacgacgtggactaccacgacttgattgccgatccgctgggtacggtggcagatatct
accggcacttcgggttgacgctgtccgacgaggctcgacaggcaatgacaaccgtccacgccgagagccag
agcggtgcccggggccccaaagcattcctattcgttggctgactacgggctcacggtcgaaatggtcaaaga
gcggttcgccgggctgtga

FIG. 5

Rv1373 (SEQ ID NO:27)

atgaattcagaacacccgatgaccgaccgggttgtgtatcgatcgttgatggccgacaacctgcgatggga
tgccctgcaattgcgcgacggcgacatcattatctcggcgccgtccaagagcggcctgacctggacacagc
gcctggtgtccctgctggtgttcgacgggcccgacttgcccggacccttgtcgacggtgtccccgtggctc
gaccagaccattcggcccatcgaggaagtggtcgctactctcgatgcccagcagcaccgccggttcatcaa
gacccacacgccgttggacggcctggtgctcgacgaccgcgtcagctacatctgcgtaggacgcgacccgc
gcgatgccgcggtgtcaatgctgtaccaatcggccaacatgaacgaagaccggatgcggattctgcacgag
gccgtagtgccgtttcacgagcgaatcgcccccccgtttgcggaactcggtcatgcgcgcagcccgaccga
ggagttccgggattggatggaggggccgaatcagcctcccctggcataggtttcacacatctgaagggga
tcggcactctggccaacatcctgcaccagctaggcacggtatgggtccgccgtcacctacccaacgtggcc
ttgtttcattacgccgattaccaggcggacttggcgggcgagctgctccggccggcaagggtcctcggtat
cgccgcgacccgcgatcgagcccgggacctggcgcagtacgccacgctggatgcgatgcgctcccgcgcgt
cagaaatcgctcctaacaccaccgacggcatctggcacagtgacgagcgtttcttccgccggggcgggagt
ggcgactggcagcagttcttcaccgaagccgagcacctgcgctactaccaccgcatcaaccagctggcgcc
acctgatctgctggcctgggcacacgagggccgccggggatacgacccggccaac

FIG. 6

AST1 (SEQ ID NO:17)
ATGAATCGCTTCTTTCTGCGCGGCGCCCTGGTGGCGCGCCTGCTGTCGGAGTCGGCCTGGAAGCAATACCC
GCAGTACGCCGACGTCGCGATCCAACGGCCGATCTTCGTCACCGGCCTGGTGCGCACCGGGACCACGGCGC
TGCACCGGCTGCTGGGCGCCGATCCCGCGCATCAGGGCCTGCACATGTGGCTGGCCGAATTCCCGCAGCCG
CGGCCGCCGCGCGAGACCTGGGAGTCCAACCCGCTGTACCGCCAGCTCGACGCGCAATTCACCCAGCACCA
CCGGGACAACCCCGGCTACACCGGGCTGCACTTCATGGCCGCCTACGAGCTGGAGGAGTGCTGGCAGCTGC
TGCGGCAGTCGCTGCACTCGGTGTCGTATGAAACGCTGGCGCACGTCCCCAGTTACGCGCAGTGGCTGTCC
GAACAGGACTGGACGCCGTCGTATCAGCGGCACCGCCGCAACCTTCAGCTGATCGGGCTCAACGACGCCGA
TAAGCGCTGGGTGCTGAAGAACCCCAGCCACCTGTTCGCGCTGGACGCGTTGATGGCCACCTACCCGGATG
CGCTGGTGATCCAGACTCATCGCCCGGTCGAAACGATCATGGCGTCGATGTGCTCGCTGGCCCAGCACACC
GCCGAAGGATGGTCGACCACGTTCGTCGGGGCCCAAATCGGCGCTGACGCAATGGATACCTGGTCGCGGGG
GCTGGAGCGGTTCAACACCGCACGGGCCAAGTACAACCCGGCGCAGTTCTACGACGTCGACTACAAGGAGT
TGATCGCCGACCCGCTGGGCACCGTGGCCGACATCTACCGGCACTTCGGCCTGACGCTGACGGAGGAGGCG
AAGGCGGCCATGGCCAAGACCCACGCCGACAGCCAGTCCGGCGAGCGGGCGCCCAAGCACAGCTACTCGCT
GGCCGACTACGGCCTCAGCGTGGAGACGGTCAAGGAGCGGTTCGCCGGGCTGTGA

FIG. 7

AST2 (SEQ ID NO:7)

```
ATGATGGCCGCGATGGCCCCGCAGTGCCCGCTGGATGCCGACGCGCTGCACGCCCAGGCCAGCGCCGACAC
CGGCCTGCACGACTTCGGGCCCGACGACTACCGGGAGCGCCTCGAGGTCTACCTGACCGCGCTGCGCGAAA
TCGACGGGCTGCACGCCGCCGGGACGGTCAACTTCTACGGTCAGCTGCTGCAGATCCTCAAGAACCGGCTG
CTGCTGACCGACCTGCTCAAGCGCCATCCCGAGATCCACGACATCGAACTGCGCTCCCCGGTGGTGATCGC
CGGGCTGCCCCGCACCGGCACCACCCACCTGCACAACCTGCTGGCCGCGCCACCCACCTTCCGCACCATGC
CCTACTGGGAAAGCGTGGAGCCGTTTCCGATGCCCAATGAGGTTGGCGTGCAACCGGATCCGCGGCGAACC
CGGATGGACGTCGCGGTCGCGGTGATCAACACGGTGATGCCGCATTTCGCGCTGATGCACGAGATGACCAC
CGATCACGTCCACGAGGAGATCCAGTTGCTGGCCAACGACGTGTCCACCATGCTGCTGGAGACGCTCGCCG
AGGTGCCGCGCTGGCGCGCCTACTACCAGGCCCACGATCAGACGCCGGCACTACGAATATCTGGCCACCCAG
CTGCGGGCGATGCAGTTCCTGCGCGGCGGCCGGCGCTGGCTGCTCAAGTCGCCTCAGCATCTCGAGCAGGT
GCCGGTGCTGGATCGGGTGTTCCCGGACAGCATCGTCGTGTTCACCCACCGCGACCCGGTGCCGGTGGCGC
TGTCGATGATCGCGATGATCACCTACTCGGCCCGCATGCACCGCTCGCCGGTGCCGGTGCGCCAGATCGCC
GAGTCCTGGATCGACCGCCTGGGGCAGATGCTGGCCGCGCTGGTCCGCGACCGCGACGTCATCGGCCCGGA
CCGTTCGATCGACATCCGCTTCGACGACTTCATGGCCGACGAACTCGGCGTGGCCGAGCGGGTCTACGCCC
TGGCGGACGAGCCGTTCACCGACGACGCGCGCGCGGCCGTCGCCGACTACCTGGCGGGTCACCGCCGCGGC
CGGCTGGGCAACGTCGAAACGTCCTACGAGATGTTCGGGTTGGACGAGGACAGCCTGCGCGAGCGTTTCGC
CCCCTACGTCGAGCGGTTCCTGGCCTAA
```

FIG. 8

AST3 (SEQ ID NO:3)

ATGACGTTCGACGTCGACGAGTTGGAGCAGGGCGCTTGCGCGGCGACCGATCTCGAGGACTTCGGCTCGCC
GTACTACCGCGAGGGACTCGAACGCATTGTTGACGCGCTGAACACCGAGGCGGACCTGAACGACATGGGCC
GGGTCATCCAGCACGCCACTATCAGCAACGCGCTAATCCAACGTCTCAAGGTCGAGCAGACCTACGCTGCG
CACCCAGAGATCGACGAGCAGGTGGTGGGCGGCCCCGTGTTCGTGATCGGATTACCCCGCACCGGGACCAC
CGCCCTGAGCCAACTCGTCGGCGCCGATCCGCAGTTCCGGTCGCTGCGGATGTGGGAATCCCAATCACCCA
CCCCGCCACCGGAAGCCGCCACCCAGCACAGCGACCCACGGATCGCACAGGCCGCCGCCGGCCTGAAAATG
CTCGACGAGATGTTCCCGCTGATGAAAACGCTGTACAACTCCGAGCCCACGGCACCTACCGAATGCCAGGA
CTTGATGGGAATGAGCTTTCGTACCTTTCACTTTGACGGTGCCGTGCGCGCACCGGGATATCTGTCCTGGC
TGATGGGCTGCGACATGCGGGGCACCTATCTGTATCACCGGCGGGTGCTCAAACTCCTGCAATGGCACTGC
CCACCGGTGCTGTGGCACCTCAAGACTCCGGTGCACATGTTCGCCCTCGACGCCCTCGTCGAGGCCTACCC
GGACGCCAAGTTCCTGTGGAGTCACCGCGACCCCGCCAAGGTGATGGCCTCGGTATGCAGCCTCATTCAAT
ACGTACGCAGCTGGAGTAGCGACCGCAACGACCCTCACGAGCTCGGCCGTGAGCAGGTCGACAGCTGGGTC
GAAGGAGTCCGTCGCGCAATGGATTTCCGTCGCCGCAACGGCGACGAGCGCTTCGCCGACGTGTCCTTCGC
CGACTTGCAGACCGACCCGGTCGGCACCCTGCGCGCCAGCTACCAGTCCCTGGGCCTGGACTTCACCGATG
ACACTTTGCACGCGGTCACGCAGTGGGCGCGGACGCATCGACCCGGTTCCCGTGGCCACCATGACTACGAC
TTGGCCGACTACGGCCTGACGCCCGAAGGTGTTCGGGAACGGTTCGCGGACTACCTCGCCGTCTACGACGC
GACGGCATGA

FIG. 9

AST4 (SEQ ID NO:11)

```
ATGCCTGGAGCCGCGCCGCCGGCACAGCTCGGTGACGAACCGCGGCGTGCGGCCGGACGCGGACGGACGGG
TGCGCATCGCGATCTCCGCGCGGGACTTCGGGTTTGGCCATTGGCTGGACACCGGCGGCCGGCATCGCGGC
TTCGTCGTGCTGCGCTGGCTGGACAACCCGAGCCCGCCCGAGGTCGCGGTGTCGGTGCGCGAAGCGCGGGA
GCGACCGTGAGCCTGCAGGACCGGTTCGCCCCGGAACGGCTGATCGCCGCCGCCTGTGAGGAGGCCGGCAG
CGACGACTTCGGCGCCGAGGGCTGGCGGCCCGGGCTGCACCGCCTCACCGACGGGCTGATCAACGACGCGC
GGCTGTCCGACATCGGCGTCGAGATCGCTCACCTGGACATCATGCGGGCGCTGAAGAACCGGCTCAACGTA
ATCGCTTGGCGCAAAGCACATCCCGAGGTGGCCGAGCAGAAGATCAGCGCCCCGATCTTCATCGTCGGCCA
GCCGCGCACCGGGACGACGATCCTCTACGACCTGCTCGCCCAGGATCCCGCGCTGCGCGCGCCGCTCACCT
GGGAGGTCGACGAGCCCTGTCCGGTGCCGCGGCCCGAGACCTATCACGACGATCCGCGCATCGCCCGGACA
CAGGCCGGCATCGACCTGTCCGAGCAGATCATGCCCGGGTTCCTGGCCTTTCACCCGATGGGCGCGCTGGT
CGGGCAGGAGTGTGTGCGCATCACCGCGGCCGAGTTCGTCAGCATGATCTTCTCTGTGCAGTACCGGCTGC
CGAACTACTACCGCTGGCTGCTGTACGAGGCGGACCACGCGGGCGCCTACCGCTTCCACCGAATTTTCCTG
CAGCACTTGCAGTCCGGCGTGCCCGGGCAGTGGTTGCTGAAATCCCCGGCGCACCTGTGGCAGCTGGATGC
GCTGCTGGCCGAGTACCCGGACGCGCTGATCGTGCAGACCCACCGCGATCCGCTCAACGTCATCTCCTCCA
TCGCGGCGCTGACCCATCACCTGCGCGGGATGTGTAGCGACGAGTCCAGCATCACCGAGTGCGCGGCGCAG
TCCTACGAGGAGATCGTCGTGGGCCTGGACCGCGAGATGGCCCTGCGCGACCGGGGCGCCGTGCCGCCCGG
GCGCGTGATCGACGTGCGGTACGCCGATTTCATGAAGGACCCGTGGACCACGATCAAAGACATCTATGAGC
GGCTGGACCGCGAGCTGCGGCCCGATGCCGAGCAGAGAATGCGCGAATTCCTCGCGTCGCATCCCTCCGAC
GGTGGGCGCAGCCGCTACACCTGGTCGGACACCGGGCTGGACGCCGGTGCGGTGCGTGAGCGGGTGCGCGC
CTATCAGGACCGCTACGGGGTACCCACCGAGGCGTTGCGCTGA
```

FIG. 10

AST5 (SEQ ID NO:9)

ATGCTCGCCGAGGCGATCGAACAGGCCGGCCTGCCCGGCGCCGACCTCGACGACACGCACGGCTTCGTCGA
CCGTCTGCACGTCCACGTCGCGGCGATCGAAGCCGACCACGGGCTGCGCCAGCTCACCCGGGGGTCGCTGC
GGCAACGCGTGGTGCGGCTGCTGCGCAACCGGTTGTCGCTGACCGAGCTGCTCCAGCGGTATCCCGAGATC
GAGTCCATCCCGATCGAGCAGCCGTTCATCGTCGTCGGGATGCCGCGTTCGGGCACCACGCATCTTGTGAA
CCTGATCGCCTGCGACCCGCGCCGGCGTGCACTGCCCTATTGGGAGAGCCAGGAGCCTATCCCGGCCCGTG
GTCAGGGCCCCGACGTCTTCGGTGTCGACCCCCGGTATGCCCGCGCCAAGGCGGAACACGAGGCGCTGATG
GCCAGCGCGCCCGTGGTGGCCGCCATGCACGACCGGTTTCCCGAGGCGATCGAGGAGGAAGTGGAACTGCT
CGACCTCGATCTGGCCTCCTACGTCCTGGAATGGCATGCGCGGGTGCCCGCCTGGCGCGATCACTACCTGA
GCCTGGACCAAACCCGGCACTACGCCTACCTGAAGAAGGTGTTGCAGGCGTTGACCTTCCTGCGCGGGCCG
CGGACCTGGGTGCTCAAAAGTCCGCAGCACTGCGAGCAGCTCGGCCCGCTGATGGCGACCTTCCCCGATGC
GACGATCGCGTTCACGCACCGCGACCCCGTCGCAGTGATCCAGTCGGCGATCACCATGATGGCCTACTCGG
ATCGGTTGCGCCGCACCAGCATTGACCCGCAGTGGCTGCTGGACTACTGGAGCGACCGGGTGCACCGACTG
CTGAGCGCCTGCGTCCGCGACCGCGACCTGGTGGCCCCGGAACGCAGCGTCGACATCAGCTTCCATCAGTT
GAGCGGCAACGAGATCCCGGTGATCGAACGGCTGTATGAGCGCGGCGGGGTGGAATTGCCGCAGCGGGTGC
GCGACCGCTTTCAGCGCTACCTGGACGGAAATCCGCGCGGTAAGCACGGCCGCATCCGCTACCAGTTGCAG
CGCCATTTCGGCATCTCCGCCGACGAGCTGCGCGCCCGTTTCGGCTTCTACTTCGACAAGTTCGACGTGCG
CCCCGAATGA

FIG. 11

AST6 (SEQ ID NO:5)

ATGTCGCCGGCGGACAGTGGATGGGCTGATCCAATGCCGGCAGTCAACGATCTCCTGCAAACCGCGGTTGC
CCAGACCGGTCTCGACGATTTCGGGGATGATTCCTTTCGAGAAGGCCTCGAGATACTGTTGACGTCGCTGC
GCGATGAGGCCCGGCTCAACGCCAAAGGTGAGGCCTTCATCTATCCGCGGATCACCGCATACCTTGCTCAG
CGGCTGCAGGTCGAGGATTGGTACCGCCGGCATCCCGAGATCGACGAGGTGTCCCTCGAGTCTCCGCTGAT
CGGGCTCGGCTTGCCGCGCACAGGGTCGACGGCATTGTCGATGCTGCTCGCTCAGGACCCCGATGTCCGGT
ATCTGCGCAAATGGGAGTCCTCCCAACCGTGTCCGCCGCCGTCGACCGTGTGCGGTGTGGATCCGCGCATC
CCGCCCGGCAAGGGGGAAATGATCGGCACTCGCCACCATGTGCCCACGGACGCCAACGGGCCGATGGAATG
TCACGAGCTGATGGCTCTGAGTTTCGCCTCCCACCTGTTCCAGTCGCTGGCCCAAGTTCCCACCTATTCGG
CGTGGCTGGTGGCCGACGCCGACCTCACCTCGGCGCTCGCGTACGAGCGTCGGGTGCTCAAGCTGCTGGCC
TGGGGTGAGCCGACGCGGCCGTGGAGGCTGAAATGCCCCTCGCACGTGCTCTGGCTTGACCGCCTGGCCGC
GGTCTTCCCAGACGCCAAATTCGTGATGACGCACCGTGATCCCACCGACGTCATCCTGTCAGTCGCCGACC
TCTACGCCGACATCATCGGCCAGTTCACCGACGACATCGACCGCCCTATATCGGGCGGCTCAACGTCGAG
CATTGGTCGTTGGGCATGGCCCGCACGCTGCAGTTCCGGGCAGCGGGCAACGATAACCGGTTCTATGACAT
CGACTTTCGCGCGATGCAGGCCGACCCGATCGGCGAGGTGACGGGATTATATCGCTGGCTTGGCGAACAGG
TCAGCGACGAATTCGAGGGCCGAATGAACAGCTGGTGGGCGCAGGCGGCAACCGAGCGCGAACCCAGCAGC
CATGCTGACCCTGTTCAGTTCGGGATCGACCTGGATTCGATACGGCCGCTGTTCGCCGACTACATCACGGC
CGCCGCCGACTGGACCGCACACGCCGACATCTAG

FIG. 12

AST7 (SEQ ID NO:1)

ATGAGCGACTTCGACAACATCACCACCGCCGACGACGTCTTCAAGCTGGCCGCGCAGCGCACCGGCCTCAG
CGAAATCGACTCCGACTCTTGGCGAGAGGGCCTGGCGCTGATCGTCGACGAGGTCAACACCTCGCCGGTCT
TCACGCCGTTCGGGCGCCAGCGAGTCCTCGACGACGCCACCAACGCGCTGGGCCGGCGCCTACAGGTGCAC
GCCTACATCCAGGACCACCCCGAGGTGCTCGACGCGCCGGTCGAGCGGCCGCTCATCGTGCTCGGCATGCC
GCGCACCGGCACCACGGTCATCAGTTACCTGCTCGACCAGGACCCGGCCCGGCGGTCGCTGCTGCACTGGC
AGTGCGTGCATCCGATCCCGCCGGCGAGCACCGAGACGCTGCGCACCGACCCGCGCTGCCTGGCCCTGCTG
GACGAGCAGCGCAAGATCCTGGACGCCGTGACACGGGCGAAAATGCCGCTGCCGCACTGGGAAGACGCCGA
CGGCCCGACCGAGGACATGTTCATCCACAACCAGGACTTCAAGGGCCTGTCCTGGGATTCCTTCCTGCCCA
CAGACCGCTACGCGCGGTGGCTGTTCGACGAAGCCGACATGAGCAGCACGTACGAGTACCAGAAGCGATAC
CTGCAGGTGCTGCAGTCCACCGCCCCGGGCAGCTGGAGCCTGAAGATGCCGTCGCATTCGGTGCACATCGA
GGCGCTGCTCAAGGTGTTCCCGGACGCCCGGCTGATCTGGGCCCACCGCGACCCGTACAAGGCGACCGGTT
CGCTGTGCAACCTGTGGCGGCTGCCGCAGAGCCTGGTGATGAACACCGAGCTTCTCGATCAGACGGAGATG
GGCCGGCTGGCGATGTGGCAGATGCGCTACCACGTCGACCGGCCGCTGCGGGCCCGCGAGCGCATCGGCGA
CGAGCGCTTCTTCCACATGTACTACCACGAGATGATGCGCGACCCGATGGACGTCATGCGGCGCATCTACG
AGTGGGCCGACGAGCCGTTGACCGCCGAAACCGAAGCGCGCATGCGCAATTGGCTCGCTCACCACCCGCAG
GACCGGTTCGCGCTCAACGCCTATCGCCTCGACGAATACGGCCTGACCGTCGAAGCGCTCCAGCCGATCTT
CGCCGAATACCTCGACACCTTCGACATTGAACTGGAAGGCAGGCCGTGA

FIG. 13

AST8 (SEQ ID NO:25)

ATGCTCGCGGCCGCCGAGGCGGAGACCGGGCTGCACGACTACGGCGATCCGACGTTGCCGCAACGCTTCAC
CGTCGCCGTCGAACACCTGAACGCCCTGGGGCTGGACGCCGATGGCCGCTTCGAAGCCGCGCAGGTGTGTC
GCTGGCTGCTGACCTCCCGCCTGGAACTCATCGAGGACCGCAACCGCTACCCGATCGGGGCCGAGGTGATC
GACGCGCCGATGTTCGTCACTGGTGAACCTCGTTCGGGCACAACGCTTATGCACGCGCTGATGTCGGTCGA
CCCGCACGCGCGGGCGTTGCGGTTCTGGGAGGTGATGTACCCGTCGCCGCCGCCGGGGCTGGCGGGGCCCG
ACGACGACCGCCGGGCGCGGGCGGACGCCGACTGGCGTGAGATCAACGCGAAGATGCCGAAGTGGCTGCAC
AGCCACCCCTACAACGACATGCTGGGCGACGGCCTGCCCGAAGACGAACGCACCTGGGCGTTCGACTTCCG
GGTGATGACGCCCACCGCGTGGTGGCGGGTGCCGATGCAGTCGCTGGTCGCCGGCCTGCCCACCGACCCGG
CCGCGCAGTACCGGCTGCACAAAGCGATGCTGCAACAGCTGCAATACAACAGGCCGCGAAAGTATTGGGTG
CTGAAGGGCTTTCATGGGTTTCGACTCAAGGAGCTGTTCGACACCTACCCCGATGCGCGGATGGTGTGGCT
GCACCGCGACCCCGTCCAGGTCGCCGCGTCGCGCACCATGATGATGGCCGACATCGCCGAGGGCATGGTCG
GGCCGGTCGACCTGCACGCAGAGGCGAAGAAGCACCTCGAGATGACCCGGGCCAGCATCGCCAACACGATG
ACCAATCCCCTGGTCGACGATCCGCGCATCCTGCACCTGAGCTACACCGACTTCATCGCCGATCATGTTGG
GGCCGTGCGGCGTTATTACGCGTTCTGCGGGCGCGAGCTCACGGCCGAGGCCGAGTCGGCGATGCGGGCCT
ACCTGGCCGACAACCCCGGCGACCGGTACGGAAAGTTCCGCTATTCCACGCAATTGCTGACCGACATCGGT
GAGGACCTCGACGCGCTGCACGCCGAATTCCGGCCGTTCCGGGAACGGTTCGGCGTCCCGATCGAAAACCG
GGGCTGA

FIG. 14

*Mycobacterium tuberculosis* H37Rv CysH (SEQ ID NO:30)

MSGETTRLTEPQLRELAARGAAELDGATATDMLRWTDETFGDIGGAGGGVSGH

RGWTTCNYVVASNMADAVLVDLAAKVRPGVPVIFLDTGYHFVETIGTRDAIESV

YDVRVLNVTPEHTVAEQDELLGKDLFARNPHECCRLRKVVPLGKTLRGYSAWV

TGLRRVDAPTRANAPLVSFDETFKLVKVNPLAAWTDQDVQEYIADNDVLVNPL

VREGYPSIGCAPCTAKPAEGADPRSGRWQGLAKTECGLHAS*

FIG. 15

*Mycobacterium smegmatis* mc²155 CysH (SEQ ID NO:31)

MTDVTTSTENELRELAERGAAELADASAEELLRWTDEHFGGNYVVASNMQDAV
LVEMAAKVRPGVDVLFLDTGYHFAETIGTRDAVEAVYDVHVVNVTPERTVAEQ
DELLGKNLFARDPGECCRLRKVVPLTNALKGYSAWVTGIRRVEAPTRANAPLIS
WDNAFGLVKINPIAAWTDEDMQNYIDANGILVNPLVYEGYPSIGCAPCTSKPIPG
ADPRSGRWAGLSKTECGLHVS*

FIG. 16

*Mycobacterium avium* CysH (SEQ ID NO:32)

MTERTTKLPEAELRELAARGAAELEGASASDVLRWTDETFGGVNGPRGWATCN
YVVASSMQEAVLIDLAAKVRPGVPVVFLDTGYHFAETIGTRDAIESVYDIRVLNV
TPEHSVAEQDKLLGKDLFARDPGECCRLRKVAPLGKTLRGYSAWVTGLRRSEA
ATRANAPVIGFDEGFKLVKVNPMATWTDEDVQNYIDEHNVLNPLIYEGYSSIG
CAPCTAKPLAGADPRSGRWQGLAKTECGLHAS*

FIG. 17

```
Myctub_CysH    1  MSGETTRLTEPQLRELAARGAAELDGATATDMLRWTDETFGDIGGAGGGVSGHRGWTTCNYVVASNMADAVLVDLA
Mycavi_CysH    1  MTERTTKLPEAELRELAARGAAELEGASASDVLRWTDETFGGVNGP-----RGWATCNYVVASSMQEAVLIDLA
Mycsme_CysH    1  -MTDVTTSTENELRELAERGAAELADASAEELLRWTDEHFG---------GNYVVASNMQDAVLVEMA
consensus         ms etTrlte eLRELAaRGAAEldgAsAtdmLRWTDEtFG  i g       rgw tcNYVVASnMqdAVLvdlA
                                                                                 **    *    *     *

Myctub_CysH    77  AKVRPGVPVIFLDTGYHFEVETIGTRDAIESVYDVRVLNVTPEHTVAEQDELLGKDLFARNPHECCRLRKVVPLGKT
Mycavi_CysH    70  AKVRPGVPVVFLDTGYHFAETIGTRDAIESVYDVRVLNVTPEHSVAEQDKLLGKDLFARDPGECCRLRKVAPLGKT
Mycsme_CysH    59  AKVRPGVDVLFLDTGYHFAETIGTRDAVEAVYDVHVVNVTPERTVAEQDELLGKNLFARDPGECCRLRKVVPLTNA
consensus         AKVRPGVpVifLDTGYHFaETIGTRDAiEsVYDvrVlNVTPEhtVAEQDeLLGKdlFARdPgECCRLRKVvPLgkt
                                                                                               *

Myctub_CysH   153  LRGYSAWVTGLRRVDAPTRANAPLVSFDETFKLVKVNPLAAWTDQDVQEYIADNDVLVNPLIVREGYPSIGCAPCTA
Mycavi_CysH   146  LRGYSAWVTGLRRSEAATRANAPVIGFDEGFKLVKVNPMATWTDEDVQNYIDEHNVLVNPLIYEGYSSIGCAPCTA
Mycsme_CysH   135  LKGYSAWVTGIRRVEAPTRANAPLISWDNAFGLVKINPIAAWTDEDMQNYIDANGILVNPLVEGYPSIGCAPCTS
consensus         LrGYSAWVTGlRRveApTRANAPlisfDegFkLVKvNPlAaWTDeDvQnYIddn vLVNPLvyEGYpSIGCAPCTa Myctub_CysH   229  KPAEGADPRSGRWQGLAKTECGLHAS (SEQ ID NO:27)
Mycavi_CysH   221  KPLAGADPRSGRWQGLAKTECGLHAS (SEQ ID NO:29)
Mycsme_CysH   211  KPIPGADPRSGRWAGLSKTECGLHVS (SEQ ID NO:28)
consensus         KPl GADPRSGRWqGLaKTECGLHaS (SEQ ID NO:30)
```

FIG. 18
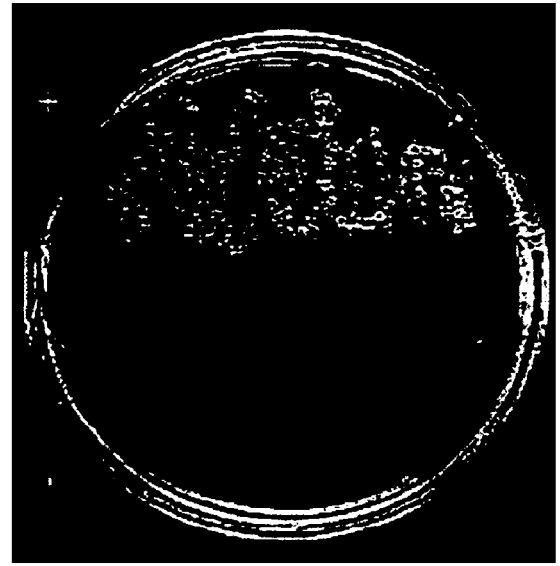
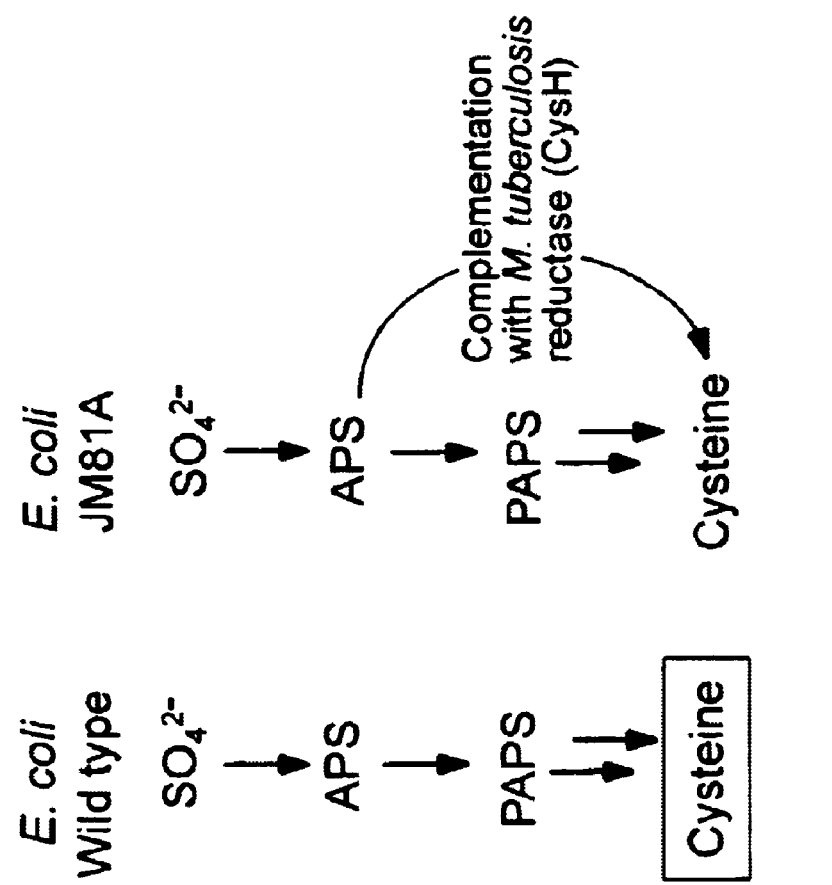

FIG. 19

*Mycobacterium smegmatis* mc²155 CysN/CysC (SEQ ID NO:34)

MSANTTLLRLATAGSVDDGKSTLIGRLLYDSKAVMEDQLAAVERTSKERGHDY

TDLALVTDGLRAEREQGITIDVAYRYFATAKRKFIIADTPGHIQYTRNMVTGTST

AQLAIVLVDARNGLLEQSRRHAFLASLLGIRHIVLAVNKMDLIGWDQERFEAIRD

EFHTFAARLDVHDVTAIPLSALQGDNVVTKSDKTPWYEGPALLAHLEDVYIAGD

RNLVDVRFPVQYVIRPQTLDHADHRSYAGTVASGVMRPGDEIVVLPSGKSSRITE

IAGPGGPVDEAFPPMAVSISLADDIDISRGDMIARPGNQPRVTQDFDATVCWMA

DDASLEPGREYLIKHTTRTTRAKVVDLDYRLDVNTLHRDKSATALKLNELGRISL

RTRTPLLLDEYSRNPATGSFILIDPHTNGTVGAGMVLRDARNESASPNTVRHENLI

TAEDRLTRGRTVWFTGLSGSGKSSVAMLVEQKLLGKGVPAYVLDGDNLRHGLN

ADLGFSMADRAENLRRLAHVASLLADSGQIVLVPAISPLEEHRELARRVSTESGV

EFFEVFCDTPLADCEARDPKGLYAKARAGEITHFTGIDSPYQRPKHPDLRLTPEHS

LDELADMVIEMLETRR*

FIG. 20

*Mycobacterium avium* CysN/CysC (SEQ ID NO:35)

MAAPTTLLRLATAGSVDDGKSTLIGRLLYDSKAVMEDQWAAVEQTSKDRGHDYTD

LALVTDGLRAEREQGITIDVAYRYFATPKRKFIIADTPGHIQYTRNMVTGASTAQLVI

VLVDARHGLLEQSRRHAFLASLLGIQHIVLAVNKMDLIGWDREKFESIRDEFHAFAA

RLDVHDVATIPISALHGDNVVTKSDQTPWYEGPALLSHLEEVYIAGDRNLVDVRFPV

QYVIRPHTHEHQDHRSYAGTVASGVMRPGDEVVVLPVGKRTRITAIEGPNGPVQEAF

PPMAVSLTLADEIDISRGDLIARTHNQPRIAQDFDATVCWMADNTTLEPGRDYVIKHT

TRTTHARVTGLDYRLDVNTLHRDKTATALKLNELGRISLRTQVPLLLDEYTRNPSTGS

FILIDPHTNGTVAAGMVLRDASAQAASPNTVRHKSSAIAAARPRGKTVWFTGLSGSG

KSSVAMLVEQKLLEKGAQAYVLDGDNLRHGLNADLGFSMADRAENLRRLAHVAAL

LADCGNVVLVPAISPLAEQRELARKVHADAGFDFIEVFCDTPIEECEKRDPKGLYAKA

RAGEITQFTGIDSPYQPPAKPDLRLTPDGTVEEQAQRVIDLLESRG*

MYCOBACTERIAL SULFATION PATHWAY PROTEINS AND METHODS OF USE THEREOF

CROSS-REFERENCE

This application is a divisional of U.S. patent application Ser. No. 10/286,606, filed Oct. 31, 2002, now U.S. Pat. No. 6,863,895, which is a continuation-in-part application of U.S. patent application Ser. No. 10/126,279, filed Apr. 19, 2002, now U.S. Pat. No. 6,858,213, which claims the benefit of U.S. Provisional Patent Application No. 60/285,394, filed Apr. 20, 2001, and U.S. Provisional Patent Application No. 60/345,953, filed Oct. 26, 2001, which applications are incorporated herein by reference in their entirety.

STATEMENT REGARDING FEDERALLY SPONSORED RESEARCH

This invention was made with U.S. government support under grant No. R01 GM59907-01 awarded by the National Institutes of Health. The U.S. government may have certain rights in this invention.

FIELD OF THE INVENTION

This invention is in the field of mycobacterial proteins, and in particular, mycobacterial sulfation pathway proteins.

BACKGROUND OF THE INVENTION

Mycobacteria are a significant cause of morbidity and mortality, particularly among immunocompromised or elderly individuals and in countries with limited medical resources. Ninety-five percent of human infections are caused by seven species: *Mycobacterium tuberculosis, M. avium* (also known as the mycobacterium avium complex or *M. avium-intracellulare*), *M. leprae, M. kansasii, M. fortuitum, M. chelonae,* and *M. absecessus*. The most common mycobacterial infections in the United States are pulmonary infections by *M. tuberculosis* or *M. avium*. Such mycobacterial infections have been of increasing concern over the past decade, particularly in light of the increasing incidence of multi-drug resistant strains.

*Mycobacterium tuberculosis* (Mtub) is the causative agent of the disease tuberculosis in humans. Estimates indicate that one-third of the world's population, including 10 million in the U.S., are infected with *M. tuberculosis,* with 8 million new cases and 3 million deaths reported world wide each year. Although incidence of tuberculosis steadily decreased since the early 1900s, this trend changed in 1984 with increased immigration from endemic countries and increased infection among homeless individuals, drug and alcohol abusers, prisoners, and HIV-infected individuals. The increasing occurrence of drug-resistant strains requires continued research into new and more effective treatments.

*M. avium* infection poses the greatest health risk to immunocompromised individuals, and is one of the most common opportunistic infections in patients with AIDS (Horsburgh (1991) *New Eng. J Med.* 324:1332–1338). In contrast with disease in other patients, *M. avium* infection can be very serious in immunocompromised individuals (e.g., AIDS patients, who have a low CD4+ T-cell count (Crowe, et al. (1991) *J. AIDS* 4:770–776)), and can result in disseminated infection in which virtually no organ is spared.

Treatment of mycobacterial infections is complicated and difficult. For example, treatment of *M. tuberculosis* and of *M. avium* infections requires a combination of relatively toxic agents, usually three different drugs, for at least six months. The toxicity and intolerability of these medications usually result in low compliance and inadequate treatment, which in turn increases the chance of therapeutic failure and enhances the selection for drug-resistant organisms. Treatment of mycobacterial infections is further complicated in pregnant women, patients with pre-existing liver or renal diseases, and immunocompromised patients, e.g., AIDS patients.

Sulfotransferases are enzymes that catalyze the transfer of a sulfate from a donor compound to an acceptor compound, usually placing the sulfate moiety at a specific location on the acceptor compound. In mycobacteria, the most notable sulfated compounds identified to date are the "sulfatides" of Mtub. Sulfatides are a closely related set of sulfated glycolipids. They are characterized by a common trehalose-2-sulfate core disaccharide. Sulfatide-1 (sulfolipid-1 or SL-1), the most abundant of the sulfatides, has been extensively studied both structurally and biologically. The molecule consists of a 2,3,6,6'-tetra-O-acyl-trehalose-2'-sulfate. Other members of the family differ in the number and type of the acyl substituents, but not in the core sulfated disaccharide. Reported biological properties of the purified SL-1 include its ability to inhibit macrophage phagosome/lysosome fusion, to enhance the secretion of TNF-α, to inhibit macrophage priming, and to activate human neutrophils.

Recently, a second set of sulfated structures have been identified and characterized in Mycobacteria. A sulfate group has been found in an ester linkage to a sugar residue of a mycobacterial glycopeptidolipid (GPL), in one case at the 2-position of a 3,4-di-O-methylrhamnose in the GPL of *M. fortuitum,* and in another case at the 4-position of a 6-deoxy-talose in a GPL of a drug-resistant strain of *M. avium.*

To date, numerous virulence factors and potential drug targets have been studied in Mtub and *M. avium* (Mav). No single genetic or metabolic entity, however, has yet to be identified as solely or even mostly responsible for the organisms' ability to cause disease in humans. In particular, information regarding the enzymes responsible for synthesizing sulfated macromolecules in mycobacteria is needed. As such, there is continued interest in identifying additional genes and gene products in Mycobacterium species that can serve as diagnostic tools, and as targets for therapeutic intervention.

*Literature* Bloom and Murray (1999) *Science* 257:105–1064 Daffe and Draper (1998) *Adv. Microb. Physiol.* 39:149–152; Hemmerich and Rosen (2000) *Glycobiol.* 10:848–856; Goren et al. (1976) *Proc. Natl. Acad. Sci. USA* 73:2510–2514; Bronzna et al. (1991) *Infect. Immun.* 59:2542–2548; Pabst et al. (1988) *J. Immunol.* 140:634–640; Zhang et al. (1991) *J. Immunol* 146:2730–2736; Lopez Marin et al. (1992) *Biochem.* 31:11106–11111; Khoo et al. (1999) *J. Biol. Chem.* 274:9778–9785; Tsukamara and Mizuno (1981) *Microbiol. Immunol.* 25:215; Cole et al. (1998) *Nature* 393:537–544; U.S. Pat. No. 6,046,002.

SUMMARY OF THE INVENTION

Novel mycobacterial sulfation pathway proteins and polypeptides related thereto, as well as nucleic acid compositions encoding the same, are provided. The subject polypeptide and nucleic acid compositions find use in a variety of applications, including research, diagnostic, and therapeutic agent screening applications. Also provided are methods of inhibiting growth and/or virulence of a pathogenic mycobacterium, and methods of treating disease conditions associated with a pathogenic mycobacterium, particularly by administering an inhibitor of a mycobacterial sulfation pathway protein. The present invention further provides genetically modified mycobacteria having a defect in a sulfation pathway enzyme gene; and immunogenic compositions that include such genetically modified mycobacteria.

BRIEF DESCRIPTIONS OF THE DRAWING

FIGS. 1A–C provide an alignment of the amino acid sequences of mycobacterial sulfotransferases. The amino acid sequences provided in FIGS. 1A–C are as follows: mav_130 (SEQ ID NO:02); mav_16 (SEQ ID NO:04); mav_131 (SEQ ID NO:06); mav_4 (SEQ ID NO:08); mav_93 (SEQ ID NO:10); mav_144 (SEQ ID NO:12); mbov_334 (SEQ ID NO:13); mtub_Rv3529c (SEQ ID NO: 15); mav_62 (SEQ ID NO:17); mav-tb_2056 (SEQ ID NO:18); mbov_479 (SEQ ID NO:19); mtub_Rv2267c (SEQ ID NO:21); and mav_304 (SEQ ID NO:23).

FIG. 2 provides an alignment of the amino acid sequences of mycobacterial sulfotransferases. The sequences of *Mycobacterium avium* glycosyl sulfotransferases correspond to the sequences in FIG. 1 as follows: identified as AST1 (mav_62) (SEQ ID NO:17); AST2 (mav_4) (SEQ ID NO:08); AST3 (mav_16) (SEQ ID NO:04); AST4 (mav_144) (SEQ ID NO:12); AST5 (mav_93) (SEQ ID NO:10); AST6 (mav_131)(SEQ ID NO:06); AST7 (mav_130) (SEQ ID NO:02); AST8 (mav_304) (SEQ ID NO:23). Additional sequences depicted in FIG. 2 are as follows: SST1 (SEQ ID NO:59); Rv1373 (SEQ ID NO:25); Rv2267c (SEQ ID NO:21); Rv3529c (SEQ ID NO:15); hGST3 (SEQ ID NO:60); and consensus (SEQ ID NO:26).

FIG. 3 provides the nucleotide sequence of Rv2267c (SEQ ID NO:20).

FIG. 4 provides the nucleotide sequence of Rv3529c (SEQ ID NO:14).

FIG. 5 provides the nucleotide sequence of Rv1373 (SEQ ID NO:24).

FIG. 6 provides the nucleotide sequence of AST1 (SEQ ID NO:16; mav_62 ).

FIG. 7 provides the nucleotide sequence of AST2 (SEQ ID NO:7; mav_4).

FIG. 8 provides the nucleotide sequence of AST3 (SEQ ID NO:3; mav_16).

FIG. 9 provides the nucleotide sequence of AST4 (SEQ ID NO:11; mav_144).

FIG. 10 provides the nucleotide sequence of AST5 (SEQ ID NO:9; mav_93).

FIG. 11 provides the nucleotide sequence of AST6 (SEQ ID NO:5; mav_131).

FIG. 12 provides the nucleotide sequence of AST7 (SEQ ID NO:1; mav_130).

FIG. 13 provides the nucleotide sequence of AST8 (SEQ ID NO:22; mav_304).

FIG. 14 provides the amino acid sequence of an APS reductase from *M. tuberculosis* H37Rv (SEQ ID NO:27).

FIG. 15 provides the amino acid sequence of an APS reductase from *M. smegmatis* mc$^2$155 (SEQ ID NO:28).

FIG. 16 provides the amino acid sequence of an APS reductase from *M. avium* SEQ ID NO:29).

FIG. 17 provides an alignment of the amino acid sequences of APS reductases from *M. tuberculosis, M. smegmatis,* and *M. avium.*

FIG. 18 depicts complementation of *E. coli* JM81A by *M. tuberculosis* CysH.

FIG. 19 provides the amino acid sequence of an APS kinase from *M. smegmatis* mc$^2$ 155 (SEQ ID NO:31).

FIG. 20 provides the amino acid sequence of an APS kinase from *M. avium* SEQ ID NO:32).

Figure 23:
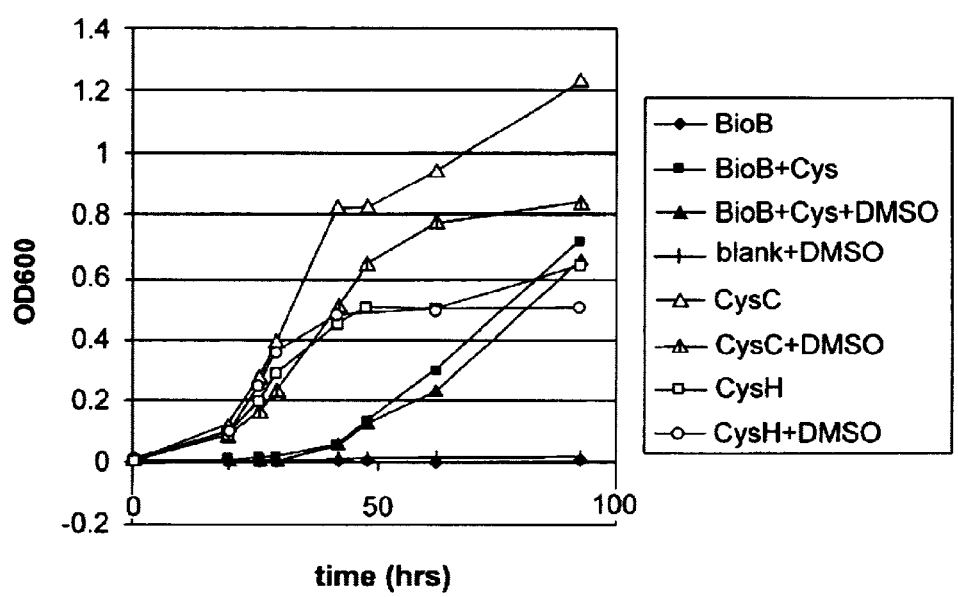

FIG. 23 depicts a growth curve for JM81A; JM81A complemented with CysC; JM81A complemented with CysH; in the presence and absence of DMSO.

Figure 24:
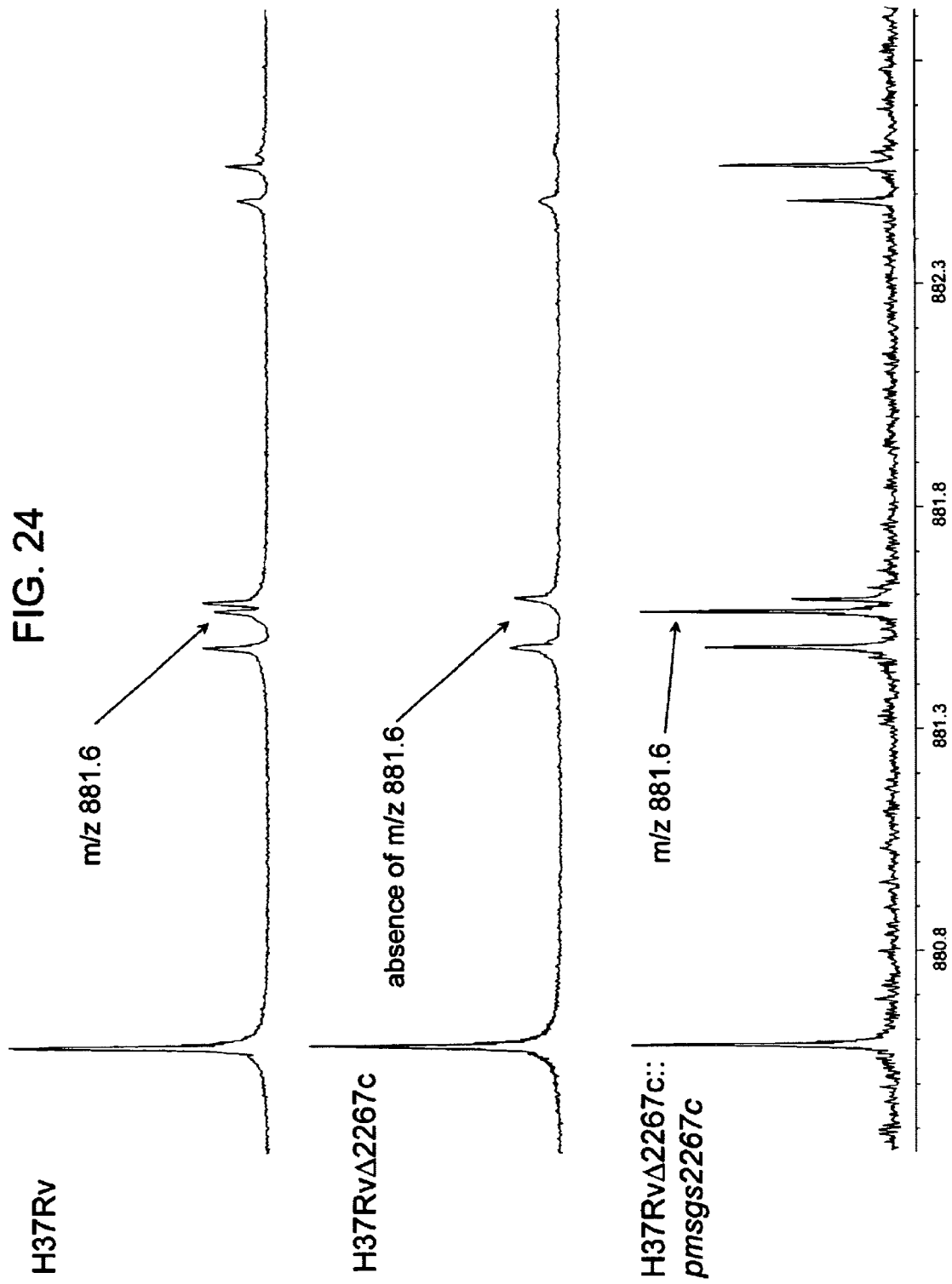

FIG. 24 depicts Fourier transform ion cyclotron resonance mass spectroscopy FT-ICR MS) analysis of *M. tuberculosis* extracts.

Figure 25:
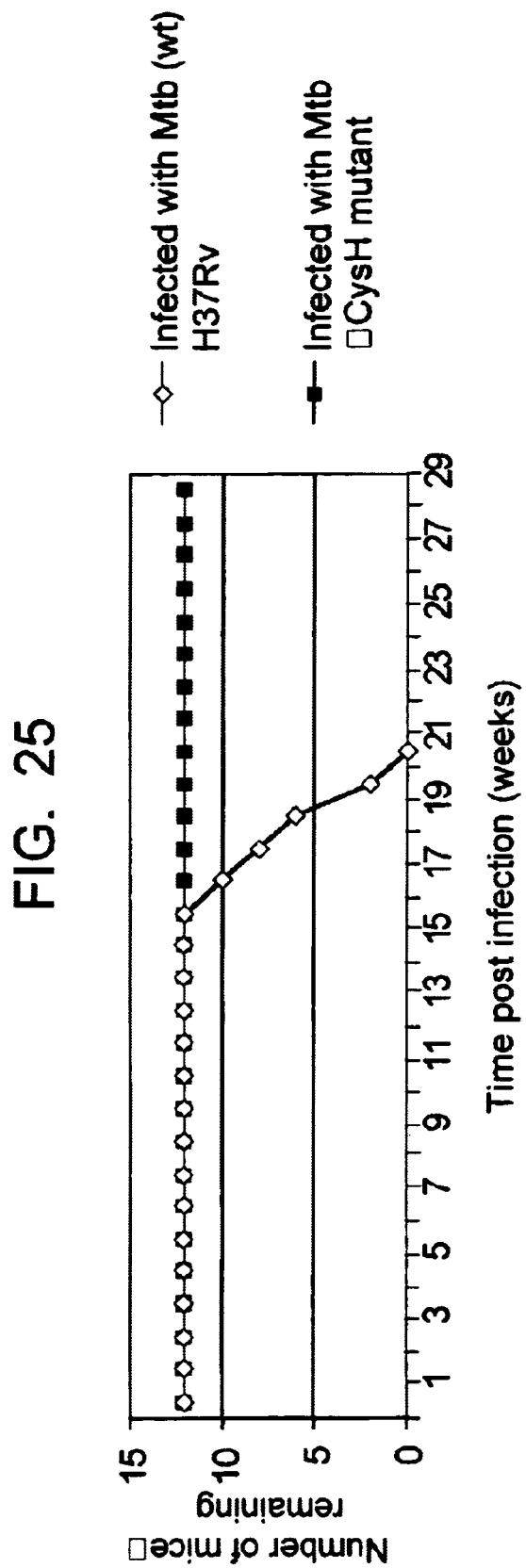

FIG. 25 depicts survival of mice infected with *M. tuberculosis* wild-type H37Rv or mutant *M. tuberculosis* H37RvΔCysH.

DETAILED DESCRIPTION OF THE INVENTION

Novel mycobacterial sulfation pathway proteins and polypeptides related thereto, as well as nucleic acid compositions encoding the same, are provided. The subject polypeptide and nucleic acid compositions find use in a variety of applications, including research, diagnostic, and therapeutic agent screening applications. Also provided are methods of inhibiting growth and/or virulence of a pathogenic mycobacterium, and methods of treating disease conditions associated with a pathogenic mycobacterium, particularly by administering an inhibitor of a mycobacterial sulfation pathway protein. The present invention further provides genetically modified mycobacteria having a defect in a sulfation pathway enzyme gene; and immunogenic compositions that include such genetically modified mycobacteria.

DEFINITIONS

The terms "polynucleotide" and "nucleic acid molecule" are used interchangeably wherein to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes single-, double-stranded and triple helical molecules. "Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as oligomers or oligos and may be isolated from genes, or chemically synthesized by methods known in the art.

The following are non-limiting embodiments of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A nucleic acid molecule may also comprise modified nucleic acid molecules, such as methylated nucleic acid molecules and nucleic acid molecule analogs. Analogs of purines and pyrimidines are known in the art. Nucleic acids may be naturally occurring, e.g. DNA or RNA, or may be synthetic analogs, as known in the art. Such analogs may be preferred for use as probes because of superior stability under assay conditions. Modifications in the native structure, including alterations in the backbone, sugars or heterocyclic bases, have been shown to increase intracellular stability and binding affinity. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O- phosphorothioate, 3'-CH$_2$-5'-O-phosphonate and 3'-NH-5'-O-phosphoroamidate. Peptide nucleic acids replace the entire ribose phosphodiester backbone with a peptide linkage.

Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity.

Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

A "substantially isolated" or "isolated" polynucleotide is one that is substantially free of the sequences with which it is associated in nature. By substantially free is meant at least 50%, preferably at least 70%, more preferably at least 80%, and even more preferably at least 90% free of the materials with which it is associated in nature. As used herein, an "isolated" polynucleotide also refers to recombinant polynucleotides, which, by virtue of origin or manipulation: (1) are not associated with all or a portion of a polynucleotide with which it is associated in nature, (2) are linked to a polynucleotide other than that to which it is linked in nature, or (3) does not occur in nature.

Hybridization reactions can be performed under conditions of different "stringency". Conditions that increase stringency of a hybridization reaction of widely known and published in the art. See, for example, Sambrook et al. (1989). Examples of relevant conditions include (in order of increasing stringency): incubation temperatures of 25° C., 37° C., 50° C. and 68° C.; buffer concentrations of 10×SSC, 6×SSC, 1×SSC, 0.1×SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or deionized water. Examples of stringent conditions are hybridization and washing at 50° C. or higher and in 0.1×SSC (9 mM NaCl/0.9 mM sodium citrate).

Stringent hybridization conditions are, for example, 50° C. or higher and 0.1×SSC (15 mM sodium chloride/01.5 mM sodium citrate) or lower. Another example of stringent hybridization conditions is overnight incubation at 42° C. in a solution: 50% formamide, 5×SSC (150 mM NaCl, 15 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65° C. Stringent hybridization conditions are hybridization conditions that are at least as stringent as the above representative conditions. Other stringent hybridization conditions are known in the art and may also be employed to identify nucleic acids of this particular embodiment of the invention.

"$T_m$" is the temperature in degrees Celsius at which 50% of a polynucleotide duplex made of complementary strands hydrogen bonded in anti-parallel direction by Watson-Crick base pairing dissociates into single strands under conditions of the experiment. $T_m$ may be predicted according to a standard formula, such as:

$$T_m = 81.5 + 16.6 \log[X^+] + 0.41 \ (\% \ G/C) - 0.61 \ (\% \ F) - 600/L$$

where [X+] is the cation concentration (usually sodium ion, Na+) in mol/L; (% G/C) is the number of G and C residues as a percentage of total residues in the duplex; (% F) is the percent formamide in solution (wt/vol); and L is the number of nucleotides in each strand of the duplex.

Stringent conditions for both DNA/DNA and DNA/RNA hybridization are as described by Sambrook et al. *Molecular Cloning, A Laboratory Manual,* 2nd Ed., Cold Spring Harbor Laboratory Press, Cold Spring Harbor, N.Y., 1989, herein incorporated by reference. For example, see page 7.52 of Sambrook et al.

A polynucleotide or polypeptide has a certain percent "sequence identity" to another polynucleotide or polypeptide, meaning that, when aligned, that percentage of bases or amino acids are the same when comparing the two sequences. Sequence similarity can be determined in a number of different manners. To determine sequence identity, sequences can be aligned using the methods and computer programs, including BLAST, available over the world wide web at http://ww.ncbi.nlm.nih.gov/BLAST/. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See *Meth. Mol. Biol.* 70: 173–187 (1997). Also, the GAP program using the Needleman and Wunsch alignment method can be utilized to align sequences. See *J. Mol. Biol.* 48:443–453 (1970)

Of interest is the BestFit program using the local homology algorithm of Smith Waterman (Advances in Applied Mathematics 2:482–489 (1981) to determine sequence identity. The gap generation penalty will generally range from 1 to 5, usually 2 to 4 and in many embodiments will be 3. The gap extension penalty will generally range from about 0.01 to 0.20 and in many instances will be 0.10. The program has default parameters determined by the sequences inputted to be compared. Preferably, the sequence identity is determined using the default parameters determined by the program.

This program is available also from Genetics Computing Group (GCG) package, from Madison, Wis., USA.

Another program of interest is the FastDB algorithm. FastDB is described in Current Methods in Sequence Comparison and Analysis, Macromolecule Sequencing and Synthesis, Selected Methods and Applications, pp. 127–149, 1988, Alan R. Liss, Inc. Percent sequence identity is calculated by FastDB based upon the following parameters:

Mismatch Penalty: 1.00;

Gap Penalty: 1.00;

Gap Size Penalty: 0.33; and

Joining Penalty: 30.0.

One parameter for determining percent sequence identity is the "percentage of the alignment region length" where the strongest alignment is found. The percentage of the alignment region length is calculated by counting the number of residues of the individual sequence found in the-region of strongest alignment. This number is divided by the total residue length of the target or query polynucleotide sequence to find a percentage.

An example is shown below:

```
Target sequence:   GCGCGAAATACTCACTCGAGG      (SEQ ID NO: 59)
                        |  |||  ||||  |||
Query sequence:    TATAGCCCTAC.CACTAGAGTCC    (SEQ ID NO: 60)
                   1    5    10   15
```

The region of alignment begins at residue 9 and ends at residue 19. The total length of the target sequence is 20 residues. The percent of the alignment region length is 11 divided by 20 or 55%, for example.

Percent sequence identity is calculated by counting the number of residue matches between the target and query polynucleotide sequence and dividing total number of matches by the number of residues of the target or query sequence found in the region of strongest alignment. For the example above, the percent identity would be 10 matches divided by 11 residues, or approximately, 90.9%.

The percent of the alignment region length is typically at least about 55% of total length of the sequence, more typically at least about 58%, and even more typically at least about 60% of the total residue length of the sequence. Usually, percent length of the alignment region can be as great as about 62%, more usually as great as about 64% and even more usually as great as about 66%.

The term "host cell" includes an individual cell or cell culture which can be or has been a recipient of any recombinant vector(s) or isolated polynucleotide of the invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with a recombinant vector or a polynucleotide of the invention. A host cell which comprises a recombinant vector of the invention is a "recombinant host cell."

The term "binds specifically," in the context of antibody binding, refers to high avidity and/or high affinity binding of an antibody to a specific polypeptide i.e., epitope of a subject polypeptide. Antibody binding to an epitope on a specific mycobacterial sulfation pathway polypeptide is preferably stronger than binding of the same antibody to any other epitope, particularly those which may be present in molecules in association with, or in the same sample, as the specific polypeptide of interest, e.g., binds more strongly to an epitope on a specific mycobacterial sulfation pathway polypeptide than to an epitope on a different mycobacterial sulfation pathway polypeptide so that by adjusting binding conditions the antibody binds almost exclusively to an epitope of the specific mycobacterial sulfation pathway polypeptide and not to any other epitope on the mycobacterial sulfation pathway polypeptide, and not to any other mycobacterial sulfation pathway polypeptide which does not comprise the epitope. In some embodiments, an antibody of the invention binds to a mycobacterial sulfation pathway polypeptide of one species, but not another, and thus can distinguish between sulfation pathway polypeptides from two mycobacterial species. Antibodies which bind specifically to a polypeptide of interest may be capable of binding other polypeptides at a weak, yet detectable, level (e.g., 10% or less of the binding shown to the polypeptide of interest). Such weak binding, or background binding, is readily discernible from the specific antibody binding to the compound or polypeptide of interest, e.g. by use of appropriate controls. In general, antibodies of the invention which bind to a specific mycobacterial sulfation pathway polypeptide with a binding affinity of $10^7$ mole/liter or more, preferably $10^8$ mole/liter or more are said to bind specifically to the specific mycobacterial sulfation pathway polypeptide. In general, an antibody with a binding affinity of $10^6$ mole/liter or less is not useful in that it will not bind an antigen at a detectable level using conventional methodology currently used.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also include samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, serum, plasma, biological fluid, and tissue samples.

"Treatment" or "treating" as used herein means any therapeutic intervention in a subject, usually a mammalian subject, generally a human subject, including: (i) prevention, that is, causing the clinical symptoms not to develop, e.g., preventing infection and/or preventing progression to a harmful state; (ii) inhibition, that is, arresting the development or further development of clinical symptoms, e.g., mitigating or completely inhibiting an active (ongoing) infection so that pathogen load is decreased to the degree that it is no longer harmful, which decrease can include complete elimination of an infectious dose of the pathogen from the subject; and/or (iii) relief, that is, causing the regression of clinical symptoms,. e.g., causing a relief of fever, inflammation, and/or other symptoms caused by an infection.

The term "effective amount" or "therapeutically effective amount" means a dosage sufficient to provide for treatment for the disease state being treated or to otherwise provide the desired effect (e.g., induction of an effective immune response). The precise dosage will vary according to a variety of factors such as subject-dependent variables (e.g., age, immune system health, etc.), the disease (e.g., the species of the infecting pathogen), and the treatment being effected. In the case of an intracellular pathogen infection, an "effective amount" is that amount necessary to substantially improve the likelihood of treating the infection, in particular that amount which improves the likelihood of successfully preventing infection or eliminating infection when it has occurred.

By "subject" or "individual" or "patient" or "host" is meant any subject for whom or which therapy is desired. Human subjects are of particular interest. Other subjects may include non-human primates, cattle, sheep, goats, dogs, cats, birds (e.g., chickens or other poultry), guinea pigs, rabbits, rats, mice, horses, and so on. Of particular interest are subjects having or susceptible to intracellular pathogen infection, particularly mycobacterial infection; more particularly to infection by M. tuberculosis, M. avium, and the like.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a polynucleotide" includes a plurality of such polynucleotides and reference to "the mycobacterium" includes reference to one or more mycobacteria and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

POLYPEPTIDE COMPOSITIONS

Novel mycobacterial sulfation pathway polypeptides, as well as polypeptide compositions related thereto, are provided. The subject sulfation pathway polypeptides are present in other than their natural environment, e.g., they are isolated. The term polypeptide composition as used herein refers to both the full length mycobacterial protein as well as portions or fragments thereof. Also included in this term are variations of the naturally occurring mycobacterial protein, where such variations are homologous or substantially similar to the naturally occurring protein, as described in greater detail below, as well as corresponding homologs from other mycobacterial species.

Mycobacterial sulfation pathway polypeptides are polypeptides that are components of a biosynthetic pathway whose end product is a sulfated glycopeptidolipid or a sulfated glycolipid found in a mycobacterium. Mycobacterial sulfation pathway polypeptides of the invention include, but are not limited to, sulfotransferases, ATP sulfurylases; adenylyl phosphosulfate (APS) reductases; 3'-phosphoadenosine-5'-phosphosulfate (PAPS) reductases; APS kinases; sulfatases; and sulfate transporters.

In the following description of the subject invention, the term M-ST is used to refer to mycobacterial sulfotransferases. A mycobacterial sulfotransferase of the invention comprises one or more of the following motifs: (1) a 5'-phosphosulfate binding loop; (2) a 3'-phosphate binding motif; and (3) a conserved RYEDL motif (SEQ ID NO:52). The 5'-phosphosulfate binding loop and the 3'-phosphate binding motif are necessary to bind the sulfate donor 3'-phosphoadenosine-5'-phosphosulfate (PAPS). PAPS is a universal sulfotransferase substrate that serves as the sulfate donor.

In particular embodiments, a mycobacterial sulfation pathway protein, e.g., an M-ST polypeptide, of the invention has an amino acid sequence of any one of the proteins identified as mav_130 (SEQ ID NO:2); mav_16 (SEQ ID NO:4); mav_131 (SEQ ID NO:6); mav_4 (SEQ ID NO:8); mav_93 (SEQ ID NO:10); mav_144 (SEQ ID NO:12); mbov_334 (SEQ ID NO:13); mtub_rv3529c (SEQ ID NO:15); mav_62 (SEQ ID NO:17); mav-tb_2056 (SEQ ID NO:18); mbov_479 (SEQ ID NO:19); mtub_rv2267c (SEQ ID NO:21); and mav_304 (SEQ ID NO:23) in FIG. 1; and rv1373 (SEQ ID NO:25) in FIG. 2. In some embodiments, an M-ST polypeptide of the invention has the sequence identified as "consensus" (SEQ ID NO:26) in FIG. 2.

Also provided are M-ST homologs. The subject M-ST homologs have a sequence that is substantially identical to Mav-130 (as shown in FIG. 1), having the amino acid sequence set forth in SEQ ID NO:02, where by "substantially identical" is meant that the protein has an amino acid sequence identity to the sequence set forth in SEQ ID NO:02 of at least about 75%, at least about 85%, at least about 85%, at least about 90, at least about 95, at least about 98%, or at least about 99%.

The mycobacterial sulfation pathway proteins of the subject invention (e.g. M-ST, etc.) are present in a non-naturally occurring environment, e.g. are separated from their naturally occurring environment. In certain embodiments, the subject proteins are present in a composition that is enriched for subject protein as compared to its naturally occurring environment. For example, purified subject protein is provided, where by purified is meant that subject protein is present in a composition that is substantially free of non-subject proteins, where by substantially free is meant that less than 90%, usually less than 60% and more usually less than 50% of the composition is made up of non-subject proteins. The proteins of the subject invention may also be present as an isolate, by which is meant that the protein is substantially free of other proteins and other naturally occurring biologic molecules, such as oligosaccharides, lipids commonly found in mycobacteria, polynucleotides and fragments thereof, and the like, where substantially free in this instance means that less than 70%, usually less than 60% and more usually less than 50%, less than about 40%, less than about 30%, or less than about 20%, of the composition containing the isolated protein is some other naturally occurring biological molecule. In certain embodiments, the proteins are present in substantially pure form, where by substantially pure form is meant at least 95%, usually at least 97% and more usually at least 99% pure.

In addition to the naturally occurring proteins, polypeptides which vary from the naturally occurring proteins are also provided. By "an M-ST" polypeptide is meant an amino acid sequence encoded by an open reading frame (ORF) of an M-ST polynucleotide, described in greater detail below, including the full length M-ST protein and fragments thereof, particularly biologically active fragments and/or fragments corresponding to functional domains, e.g. acceptor binding site (postulated to be the most 5' consensus region, the donor binding site, e.g. RYEDL, and the like; and including fusions of the subject polypeptides to other proteins or parts thereof. Thus, in some embodiments, an M-ST polypeptide comprises at least about 10, at least about 25, at least about 50, at least about 75, at least about 100, at least about 125, at least about 150, at least about 175, at least about 200, at least about 225, at least about 250, at least about 275, or at least about 300, contiguous amino acids of any one of SEQ ID NOs: 2, 4, 6, 8, 10, 12, 13, 15, 17, 18, 19, 21, 23, and 25. In many embodiments, an M-ST polypeptide of the invention comprises the complete amino acid sequence of any one of SEQ ID NOs: 2, 4, 6, 8, 10, 12, 13, 15, 17, 18, 19, 21, 23, and 25.

Also provided are polypeptides that include an amino acid sequence of any one of SEQ ID NOs: 27, 28, and 29, depicted in FIGS. 14–17. Polypeptides of interest that include an amino acid sequence of any one of SEQ ID NOs: 27, 28, and 29 are those that exhibit APS reductase activity. Also provided are polypeptides that include an amino acid sequence that has at least about 75%, at least about 80%, at least about 85%, at least about 90%, at least about 95%, at least about 97%, at least about 98%, or at least about 99% amino acid sequence identity to the amino acid sequence set forth in any one of SEQ ID NOs: 27, 28, and 29, depicted in FIGS. 14–17. Also provided are polypeptides that include at least about 10, at least about 25, at least about 50, at least about 75, at least about 100, at least about 125, at least about 150, at least about 175, at least about 200, or at least about 225 contiguous amino acids of the amino acid sequence set forth in any one of SEQ ID NOs: 27, 28, and 29, depicted in FIGS. 14–17.

Also provided are polypeptides that include an amino acid sequence of any one of SEQ ID NOs: 31 and 32, depicted in FIGS. 19, and 20, respectively. Polypeptides of interest that include an amino acid sequence of any one of SEQ ID NOs: 31 and 32 are those that exhibit APS kinase activity. Also provided are polypeptides that include an amino acid sequence that has at least about 75%, at least about 80%, at least about 85%, at least about 90%, at least about 95%, at least about 97%, at least about 98%, or at least about 99% amino acid sequence identity to the amino acid sequence set forth in any one of SEQ ID NOs: 31 and 32, depicted in FIGS. 19, and 20, respectively. Also provided are polypeptides that include at least about 10, at least about 25, at least about 50, at least about 75, at least about 100, at least abut 125, at least about 150, at least about 175, at least about 200, at least about 250, at least about 300, at least about 350, at least about 400, at least about 450, at least about 500, at least about 550, or at least about 600 contiguous amino acids of the amino acid sequence set forth in any one of SEQ ID NOs: 31 and 32, depicted in FIGS. 19, and 20, respectively.

Also provided are mutants of a mycobacterial sulfation pathway polypeptide, e.g., an M-ST, an APS reductase, an APS kinase, etc. In some embodiments, mutants have altered physical characteristics, compared to a "wild-type" or naturally occurring mycobacterial sulfation pathway polypeptide. Physical characteristics of a mutant mycobacterial sulfation pathway polypeptide of the invention include one or more of the following: (1) increased solubility in aqueous solution;: (2) correct folding during translation; (3) mutations that alter antigenicity; and (4) mutations that increase or decrease enzyme turnover. Mutants can be generated using well-known techniques for mutagenesis of a nucleic acid molecule. Random mutagenesis of a polynucleotide comprising a nucleotide sequence encoding a mycobacterial sulfation pathway polypeptide can be carried out, using techniques that are standard in the art, and the polypeptides encoded thereby evaluated for various physical properties described above. Mutants can also be selected for various physical properties.

For example, one can select for properly folded mutants in the following manner. Following random mutagenesis of a polynucleotide comprising a nucleotide sequence encoding a mycobacterial sulfation pathway polypeptide, the polynucleotide can be cloned into an expression vector comprising a nucleotide sequence encoding a detectable marker protein, e.g., a chromoprotein or fluoroprotein (fluorescent protein) (e.g., green fluorescent protein from *Aequorea victoria;* or any fluorescent protein from, e.g., an anthozoan species) such that a fusion protein is encoded. Fluorescent proteins include, but are-not limited to, a green fluorescent protein (GFP), including, but not limited to, a "humanized" version of a GFP, e.g., wherein codons of the naturally-occurring nucleotide sequence are changed to more closely match human codon bias; a GFP derived from *Aequoria victoria* or a derivative thereof, e.g., a "humanized" derivative such as Enhanced GFP, which are available commercially, e.g., from Clontech, Inc.; a GFP from another species such as *Renilla reniformis, Renilla mulleri,* or *Ptilosarcus guernyi,* as described in, e.g., WO 99/49019 and Peelle et al. (2001) *J. Protein Chem.* 20:507–519; "humanized" recombinant GFP (hrGFP) (Stratagene); any of a variety of fluorescent and colored proteins from Anthozoan species, as described in, e.g., Matz et al. (1999) *Nature Biotechnol.* 17:969–973; and the like. Where the fusion partner is an enzyme that yields a detectable product, the product can be detected using an appropriate means, e.g., β-galactosidase can, depending on the substrate, yield colored product, which is detected spectrophotometrically, or a fluorescent product; luciferase can yield a luminescent product detectable with a luminometer; etc.

The fusion protein comprises the mycobacterial sulfation pathway protein fused in-frame to the detectable marker protein. After transfection into a suitable host cell, e.g., *Mycobacterium smegmatis, E. coli,* and the like) colonies are examined visually for the presence of the detectable marker protein. If the detectable marker protein is detectable, e.g., it fluoresces or is colored, then it is likely properly folded. The mycobacterial sulfation pathway polypeptide is therefore also likely to be properly folded.

The subject proteins and polypeptides may be obtained from naturally occurring sources or synthetically produced. Where obtained from naturally occurring sources, the source chosen will generally depend on the species from which the protein is to be derived. For example, Mtub sulfotransferase is generally derived from *Mycobacterium tuberculosis*. The subject proteins may also be derived from synthetic means, e.g. by expressing a recombinant gene encoding protein of interest in a suitable host, as described in greater detail below. Any convenient protein purification procedures may be employed, where suitable protein purification methodologies are described in Guide to Protein Purification, (Deuthser ed.) (Academic Press, 1990). For example, a lysate may prepared from the original source, e.g. a mycobacterium or the expression host, and purified using HPLC, exclusion chromatography, gel electrophoresis, affinity chromatography, and the like.

POLYNUCLEOTIDE COMPOSITIONS; RECOMBINANT VECTORS; HOST CELLS

Also provided are polynucleotide compositions encoding mycobacterial sulfation pathway proteins (e.g., M-ST and the like) or fragments thereof, where the nucleotide sequence of the polynucleotide differs from a wild-type or naturally occurring polynucleotide that comprises a nucleotide sequence encoding a mycobacterial sulfation pathway protein. The invention further provides recombinant vectors comprising a subject polynucleotide, as well as host cells comprising a subject polynucleotide and host cells comprising a subject recombinant vector.

By mycobacterial sulfation pathway polynucleotide composition is meant a composition comprising a sequence of polynucleotide having an open reading frame that encodes mycobacterial sulfation pathway polypeptide of the invention, and is capable, under appropriate conditions, of being transcribed and translated such that a mycobacterial sulfation pathway polypeptide is produced. Also encompassed in this term are polynucleotides that are homologous or substantially similar or identical to the polynucleotides encoding mycobacterial sulfation pathway polypeptides. Thus, the subject invention provides genes encoding mycobacterial sulfation pathway polypeptides and homologs thereof.

The nucleotide sequences set forth in SEQ ID NO:1, 3, 5, 7, 9, 11, 14, 16, 20, 22, and 24 encode polypeptides identified as SEQ ID NO:2, 4, 6, 8, 10, 12, 15, 17, 21, 23, and 25, respectively. In all embodiments, the nucleotide sequences set forth in SEQ ID NO: 1, 3, 5, 7, 9, 11, 14, 16, 20i 22, and 24 are specifically excluded. Polynucleotides of the invention comprise nucleotide sequences that differ in nucleotide sequence from the sequences set forth in SEQ ID NO: 1, 3, 5, 7, 9, 11, 14, 16, 20, 22, and 24 by at least about 5%.

In some embodiments a mycobacterial sulfation pathway polynucleotide of the invention shares from about 50% to about 60%, from about 60% to about 65%, from about 65% to about 70%, from about 70% to about 75%, from about 75% to about 80% from about 80% to about 85%, from about 85% to about 90%, from about 90% to about 95%, nucleotide sequence identity to the coding region of any one of SEQ ID NOs: 1, 3, 5, 7, 9, 11, 14, 16, 20, 22, and 24. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et at. (1990), *J. Mol. Biol.* 215:403–10 (using default settings). The sequences provided herein are essential for recognizing related and homologous proteins in database searches.

In some embodiments, a mycobacterial sulfation pathway polynucleotide of the invention encodes a mycobacterial sulfation pathway polypeptide. In some of these embodiments, a mycobacterial sulfation pathway polynucleotide of the invention comprises a nucleotide sequence that encodes a polypeptide comprising at least about 10, at least about 25, at least about 50, at least about 75, at least about 100, at least about 125, at least about 150, at least about 175, at least about 200, at least about 225, at least about 250, at least about 275, or at least about 300, contiguous amino acids of any one of SEQ ID NOs: 2, 4, 6, 8, 10, 12, 15, 17, 21, 23, and 25. In many embodiments, a mycobacterial sulfation pathway polynucleotide of the invention comprises a nucleotide sequence that encodes a polypeptide comprising the complete amino acid sequence of any one of SEQ ID NOs:2, 4, 6, 8, 10, 12, 15, 17, 21, 23, and 25.

In other embodiments, a mycobacterial sulfation pathway polynucleotide includes a nucleotide sequence that encodes a polypeptide having at least about 75%, at least about 80%, at least about 85%, at least about 90%, at least about 95%, at least about 97%, at least about 98%, or at least about 99% amino acid sequence identity with any one of SEQ ID NOs:27, 28, 29, 30, 31, and 32.

In other embodiments, a mycobacterial sulfation pathway polynucleotide includes a nucleotide sequence that encodes a polypeptide that includes at least about 10, at least about 25, at least about 50, at least about 75, at least about 100, at least about 125, at least about 150, at least about 175, at least about 200, or at least about 225 contiguous amino acids of the amino acid sequence set forth in any one of SEQ ID NO:27, 28, and 29, depicted in FIGS. 14–17.

In other embodiments, a mycobacterial sulfation pathway polynucleotide includes a nucleotide sequence that encodes a polypeptide that includes at least about 10, at least about 25, at least about 50, at least about 75, at least about 100, at least about 125, at least about 150, at least about 175, at least about 200, at least about 250, at least about 300, at least about 350, at least about 400, at least about 450, at least about 500, at least about 550, or at least about 600 contiguous amino acids of the amino acid sequence set forth in any one of SEQ ID NOs:31 and 32, depicted in FIGS. 19, and 20, respectively.

Mycobacterial sulfation pathway polynucleotides of the invention differ from wild-type mycobacterial polynucleotides. The subject polynucleotides are typically generated by random or directed mutagenesis of wild-type mycobacterial sulfation pathway polynucleotides. The source of wild-type mycobacterial sulfation pathway polynucleotide is any mycobacterial species, e.g., by *M. tuberculosis, M. avium* (or *M. avium-intracellulare*), *M. leprae* (particularly *M. leprae* infection leading to tuberculoid leprosy), *M. kansasii, M. fortuitum, M. chelonae,* and *M. absecessus.*

Nucleic acids encoding the polypeptides of the subject invention may be cDNA or genomic DNA or a fragment thereof. The term "mycobacterial sulfation pathway gene" refers to the open reading frame encoding specific mycobacterial sulfation pathway proteins and polypeptides, as well as adjacent 5' and 3' non-coding nucleotide sequences involved in the regulation of expression, up to about 20 kb beyond the coding region, but possibly further in either direction. The gene may be introduced into an appropriate vector for extrachromosomal maintenance or for integration into a host genome.

The term "cDNA" as used herein is intended to include all nucleic acids that share the arrangement of sequence elements found in native mature mRNA species, where sequence elements are coding regions, as well as 3' and 5' non-coding regions. Normally mRNA species have a sequence of a continuous open reading frame encoding a mycobacterial sulfation pathway protein.

A genomic sequence of interest comprises the nucleic acid present between the initiation codon and the stop codon, as defined in the listed sequences that are normally present in a native chromosome. It may further include the 3' and 5' untranslated regions found in the mature mRNA. It may further include specific transcriptional and translational regulatory sequences, such as promoters, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence. The genomic DNA flanking the coding region, either 3' or 5', or internal regulatory sequences, contains sequences required for proper expression (e.g., expression during a specific phase of growth or exposure to a regulator of expression).

The mycobacterial sulfation pathway genes are isolated and obtained in substantial purity, generally as other than an intact chromosome. Usually, the DNA will be obtained substantially free of other nucleic acid sequences that do not include a mycobacterial sulfation pathway sequence or fragment thereof, generally being at least about 50%, usually at least about 90% pure and are typically "recombinant", i.e. flanked by one or more nucleotides with which it is not normally associated on a naturally occurring chromosome.

In addition to the plurality of uses described in greater detail in following sections, the subject nucleic acid compositions find use in the preparation of all or a portion of the subject polypeptides, as described above. For expression, an expression cassette may be employed. The expression vector will provide a transcriptional and translational initiation region, which may be inducible or constitutive, where the coding region is operably linked under the transcriptional control of the transcriptional initiation region, and a transcriptional and translational termination region. These control regions may be native to a mycobacterial sulfation pathway gene, or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for the production of fusion proteins, where the exogenous fusion peptide provides additional functionality, i.e. increased protein synthesis, stability, reactivity with defined antisera, an enzyme marker, e.g. β-galactosidase, a fluoroprotein, a chromoprotein, etc.

Expression vectors for introducing exogenous coding sequences into mycobacteria are known in the art, any of which can be used herein. See, e.g., U.S. Pat. No. 5,968,733; U.S. Pat. No. 6,074,866; U.S. Pat. No. 6,015,696; Triccas et al. (1998) *FEMS Microbiol. Lett.* 167:151–156; and Das-Gupta et al. (1998) *Biochem. Biophys. Res. Commun.* 246:797–804. Examples of expression vectors include those that utilize Hsp60 promoters, the promoter normally associated with the coding region for the specific protein, the glutamine synthase promoter, or the inducible acetamidase promoter. Many of these promoters are used in the pMS series of vectors. These vectors often include the Hyg (hygromycin) resistance gene. Vectors can provide for inducible expression of a protein, by using an inducible promoter, e.g., the acetamidase promoter (inducible by adding acetamide to the culture medium), and the like.

Expression cassettes may be prepared comprising a transcription initiation region, the gene or fragment thereof, and a transcriptional termination region. Of particular interest is the use of sequences that allow for the expression of functional epitopes or domains, usually at least about 8 amino acids in length, more usually at least about 15 amino acids in length, to about 25 amino acids, and up to the complete open reading frame of the gene. After introduction of the DNA, the cells containing the construct may be selected by means of a selectable marker, the cells expanded and then used for expression.

Subject proteins and polypeptides may be expressed in prokaryotes or eukaryotes in accordance with conventional ways, depending upon the purpose for expression. For large scale production of the protein, a unicellular organism, such as *Mycobacterium smegmatis, E. coli, B. subtilis, S. cerevisiae,* insect cells in combination with baculovirus vectors, or cells of a higher organism such as vertebrates, e.g., mammals, e.g. COS 7 cells, may be used as the expression host cells. Of particular interest in many embodiments is the use of non-pathogenic strains of mycobacteria, e.g., *Mycobacterium smegmatis, Mycobacterium bovis*-BCG (Bacille Calmette Guerin), and the like. Small peptides can also be synthesized in the laboratory. Polypeptides that are subsets of the complete mycobacterial sulfation pathway protein sequence may be used to identify and investigate parts of the protein important for function.

ANTIBODIES SPECIFIC FOR A MYCOBACTERIAL SULFATION PATHWAY POLYPEPTIDE OF THE INVENTION

The invention provides antibodies that are specific for a subject mycobacterial sulfation pathway polypeptide. Suitable antibodies are obtained by immunizing a host animal with peptides comprising all or a portion of the subject protein. Suitable host animals include mouse, rat sheep, goat, hamster, rabbit, etc.

The immunogen may comprise the complete protein, or fragments and derivatives thereof. Preferred immunogens comprise all or a part of one of the subject proteins, where these residues contain the post-translation modifications, such as glycosylation, found on the native target protein. Immunogens comprising one or more epitopes are produced in a variety of ways known in the art, e.g. expression of cloned genes using conventional recombinant methods, isolation from mycobacteria, etc.

For preparation of polyclonal antibodies, the first step is immunization of the host animal with a subject protein, where the subject protein will preferably be in substantially pure form, comprising less than about 1% contaminant. The immunogen may comprise the complete subject protein, fragments or derivatives thereof. To increase the immune response of the host animal, the subject protein may be combined with an adjuvant, where suitable adjuvants include alum, dextran, sulfate, large polymeric anions, oil & water emulsions, e.g. Freund's adjuvant, Freund's complete adjuvant, and the like. The subject protein may also be conjugated to synthetic carrier proteins or synthetic antigens. A variety of hosts may be immunized to produce the polyclonal antibodies. Such hosts include rabbits, guinea pigs, rodents, e.g. mice, rats, sheep, goats, and the like. The subject protein is administered to the host, usually intradermally, with an initial dosage followed by one or more, usually at least two, additional booster dosages. Following immunization, the blood from the host will be collected, followed by separation of the serum from the blood cells. The Ig present in the resultant antiserum may be further fractionated using known methods, such as ammonium salt fractionation, DEAE chromatography, and the like.

Monoclonal antibodies are produced by conventional techniques. Generally, the spleen and/or lymph nodes of an immunized host animal provide a source of plasma cells. The plasma cells are immortalized by fusion with myeloma cells to produce hybridoma cells. Culture supernatant from individual hybridomas is screened using standard techniques to identify those producing antibodies with the desired specificity. Suitable animals for production of monoclonal antibodies to the mycobacterial protein include mouse, rat, hamster, etc. The antibody may be purified from the hybridoma cell supernatants or ascites fluid by conventional techniques, e.g. affinity chromatography using protein according to the subject invention bound to an insoluble support, protein A sepharose, etc.

The antibody may be produced as a single chain, instead of the normal multimeric structure. Single chain antibodies are described in Jost et al. (1994) *J.B.C.* 269:26267–73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

For in vivo use, particularly for injection into humans, it is desirable to decrease the antigenicity of the antibody. An immune response of a recipient against the blocking agent will potentially decrease the period of time that the therapy is effective. Methods of humanizing antibodies are known in the art. The humanized antibody may be the product of an animal having transgenic human immunoglobulin constant region genes (see for example International Patent Applications WO 90/10077 and WO 90/04036). Alternatively, the antibody of interest may be engineered by recombinant DNA techniques to substitute the CH1, CH2, CH3, hinge domains, and/or the framework domain with the corresponding human sequence (see WO 92/02190).

The use of Ig cDNA for construction of chimeric immunoglobulin genes is known in the art (Liu et al. (1987) *P.N.A.S.* 84:3439 and (1987) *J. Immunol.* 139:3521). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) *Sequences of Proteins of Immunological Interest*, N.I.H. publication no. 91–3242. Human C region genes are readily available from known clones. The choice of isotype will be guided by the desired effector functions, such as complement fixation, or activity in antibody-dependent cellular cytotoxicity. Preferred isotypes are IgG1, IgG3 and IgG4. Either of the human light chain constant regions, kappa or lambda, may be used. The chimeric, humanized antibody is then expressed by conventional methods.

In yet other embodiments, the antibodies may be fully human antibodies. For example, xenogeneic antibodies which are identical to human antibodies may be employed. By xenogeneic human antibodies is meant antibodies that are the same has human antibodies, i.e. they are fully human antibodies, with exception that they are produced using a non-human host which has been genetically engineered to express human antibodies. See e.g. WO 98/50433; WO 98,24893 and WO 99/53049, the disclosures of which are herein incorporated by reference.

Antibody fragments, such as Fv, $F(ab')_2$ and Fab may be prepared by cleavage of the intact protein, e.g. by protease or chemical cleavage. Alternatively, a truncated gene is designed. For example, a chimeric gene encoding a portion of the $F(ab')_2$ fragment would include DNA sequences encoding the CH1 domain and hinge region of the H chain, followed by a translational stop codon to yield the truncated molecule.

Consensus sequences of H and L J regions maybe used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g. SV-40 early promoter, (Okayama et al. (1983) *Mol. Cell. Bio.* 3:280), Rous sarcoma virus LTR (Gorman et al. (1982) *P.N.A.S.* 79:6777), and moloney murine leukemia virus LTR (Grosschedl et al. (1985) *Cell* 41:885); native Ig promoters, etc.

GENETICALLY ALTERED MYCOBACTERIA

The invention further provides genetically altered mycobacteria. A polynucleotide of the invention, or a wild-type mycobacterial sulfation pathway polynucleotide, or other polynucleotide, can be used to genetically alter a mycobacterium. In some embodiments, a genetically altered mycobacterium over-expresses a sulfation pathway enzyme. In some embodiments, the invention provides knock-out mutants, where an endogenous mycobacterial sulfation pathway gene is functionally disabled via homologous recombination. Such genetically altered mycobacteria are attenuated, i.e., their ability to invade and infect is reduced. A subject genetically modified mycobacterium is therefore useful in immunogenic compositions, e.g., as vaccines. A subject genetically modified mycobacterium is also useful in cell-based screening assays (described below), where a subject genetically modified mycobacterium that has a functionally disabled sulfation pathway gene is useful as a control.

Homologous recombination is carried out using well-established techniques. Exogenous DNA, which includes DNA homologous to genomic DNA of the recipient mycobacterium (homologous DNA), as well as DNA which is not homologous to genomic DNA of the recipient mycobacterium (nonhomologous DNA), is introduced into a mycobacterium. Exogenous DNA is integrated into genomic DNA. The DNA construct includes homologous DNA for targeting into a homologous genomic locus and DNA which acts to knock out (inactivate) or activate a resident (endogenous) mycobacterial gene. In the case of inactivation, the mycobacterial gene is "knocked out", in the sense that it is rendered inactive by addition of DNA whose presence interferes with its ability to function, by removal or replacement of sequences necessary for it to be functional or by its complete removal from the mycobacterial genome. Methods of homologous recombination in mycobacteria are described in detail in Ganjam et al. (1991) *Proc. Natl. Acad. Sci. USA* 88:5433–5437; Aldovini et al. (1993) *J. Bacteriol.* 175:7282–7289, which are incorporated herein by reference.

Knock-out by homologous recombination are performed using established techniques. See, e.g., U.S. Pat. No. 6,136,324. General protocols for generating knockouts are provided in the Examples section. For example, an allelic replacement method can be performed, as described in the Examples, using well-known techniques. See, e.g., Parish and Stoker (2000) *Microbiology* 146(8):1969–75.

Any other method of genetically modifying a mycobacterium, such that is functionally disabled sulfation pathway enzyme gene is generated, can be used. Standard methods include random and site-specific mutagenesis. Random or site-specific mutagenesis is used to generate mutants in a transcriptional or translation control element, in a coding region, and the like, to generate a genetically modified mycobacterium that has a functionally disabled sulfation pathway enzyme gene.

In general, a subject genetically modified mycobacterium has a functionally disabled sulfation pathway gene. A subject genetically modified, attenuated mycobacterium typically has a genetic modification in one or more of a sulfotransferase gene, an ATP sulfurylase gene, an APS reductase gene, a PAPS reductase gene, an APS kinase gene, a sulfatase gene, and a sulfate transporter gene, such that the gene is functionally disabled. A "functionally disabled sulfation pathway gene" is a sulfation pathway gene that is genetically altered such that the level of protein encoded by the gene is at background levels (e.g., undetectable, or at or near the lower limit of detection), or is undetectable; such that the protein encoded by the gene is produced but is non-functional; such that the encoded protein produced and is functional but is produced at levels that are too low to be effective in carrying out the normal function of the protein in the bacterium; or such that the encoded protein produced is functional but is produced at levels that are lower than normal (e.g., lower than wild-type levels) such that bacterial virulence is attenuated.

A subject genetically modified mycobacterium that has a functionally disabled sulfation pathway enzyme gene exhibits reduced virulence as a result of the functional disablement of the gene. Virulence in a subject genetically modified mycobacterium is reduced by at least about 10%, at least about 20%, at least about 25%, at least about 30%, at least about 40%, at least about 50%, at least about 60%, at least about 70%, at least about 80%, at least about 90%, or more (e.g., 95%, 99%, 100%), compared with a wild-type mycobacterium of the same species and not having the genetic modification, e.g., a wild-type mycobacterium that is virulent.

In some embodiments, the $LD_{50}$ of a subject genetically modified mycobacterium is at least about 2-fold, at least about 5-fold, at least about 10-fold, at least about 20-fold, at least about 25-fold, at least about 50-fold, at least about 100-fold, at least about 150-fold, at least about 200-fold, or at least about 250-fold, or more, higher than the $LD_{50}$ of a wild-type mycobacterium of the same species and not having the genetic modification.

Virulence is determined using any known assay. The term "virulence" encompasses two features of a pathogenic organism: its infectivity (i.e., the ability to colonize a host) and the severity of the disease produced. Virulence can be expressed as the $LD_{50}$, i.e., the dose that will kill 50% of inoculated animals within a given time. Virulence can also be expressed as transmissibility, i.e., the ability of a bacterium to cause a demonstrable infection in a given animal host. Transmissibility is usually detected by culture methods. The dose required is the $ID_{50}$, the infection dose in 50% of animals. Virulence can also be expressed as communicability. Virulence can be tested using any known assay, including, but not limited to, mouse colony formation assay, in which the number of mycobacterial colonies in the lung of infected mice is counted at various time points after infection; and macrophage infectivity assays. Other laboratory animals such as rabbits and guinea pigs can also be used. Virulence can also be determined in a cell culture assay using macrophages. Bacteria are incubated with cultured macrophages and the number of bacteria that enter the macrophages determined by washing the macrophages, lysing them, culturing their contents on plates, and counting "colony forming units."

In particular embodiments, a subject genetically altered mycobacterium has a functionally disabled APS reductase gene. In other particular embodiments, a subject genetically modified mycobacterium has a functionally disabled APS kinase gene. In still other particular embodiments, a subject genetically altered mycobacterium has a functionally disabled sulfotransferase gene. Examples of such mycobacteria are found in Examples 3, 6, and 9. In some embodiments, a genetically altered mycobacterium is a strain that is normally pathogenic, but exhibits reduced virulence by virtue of the genetic modification. In particular embodiments, a subject genetically altered mycobacterium is *M. tuberculosis*. The present invention also provides immunogenic compositions comprising genetically altered mycobacterium, which compositions are described in more detail below.

METHODS

The invention further provides screening methods and therapeutic methods. Screening methods identify agents that reduce an activity of a mycobacterial sulfation pathway polypeptide. Therapeutic methods of the invention include methods of treating a mycobacterial infection in an individual, methods of reducing viability of a pathogenic mycobacterium, methods of reducing virulence of a pathogenic mycobacterium, and methods of increasing a protective immune response to a mycobacterium.

SCREENING ASSAYS

The present invention further provides in vitro screening assays to identify agents that modulate an activity of a component of a mycobacterial sulfation pathway, e.g., a component of a pathway whose end product is a sulfated macromolecule. The screening assays are designed to identify agents that are useful as therapeutic agents for treating mycobacterial infections. Both cell-based and cell-free assays are provided.

In some embodiments, the screening assays are cell-free screening assays. In these embodiments, the methods generally involve contacting a mycobacterial sulfation pathway component with a test agent, and determining the effect, if any, on an activity, e.g., an enzymatic activity, of the pathway component. Sulfation pathway components that are suitable for use in a cell-free screening assay include, but are not limited to, mycobacterial sulfotransferases; mycobacterial ATP-sulfurylases; mycobacterial APS kinases; mycobacterial PAS and PAPS reductases; and mycobacterial sulfatases. For example, recombinant M-ST polypeptide can be combined with $^{35}$S-labeled sulfate donor such as [$^{35}$S]-PAPS, candidate inhibitor compound, and an acceptor molecule.

In other embodiments, the methods provide cell-based assays. In these embodiments, the methods generally involve contacting a host cell which produces an M-ST polypeptide with a labeled sulfate, e.g. $^{35}$S-labeled sulfate and a candidate agent, and determining the effect, if any, on the amount of sulfate incorporation into a substrate for the M-ST in the presence and absence of a candidate agent.

Suitable sulfate acceptor molecules include, but are not limited to, glycopeptidolipids (GPL), including, but not limited to, a GPL containing a 3,4,-di-O-methylrhamnose, and a GPL containing a 6-deoxy-talose; trehalose-containing glycolipids; and glycolipids or glycoproteins of mammalian origin.

A variety of different candidate agents ("test agents") may be screened by the screening methods of the invention. Candidate agents encompass numerous chemical classes, though typically they are organic molecules, and may be small organic compounds having a molecular weight of more than 50 and less than about 2,500 daltons. Candidate agents comprise functional groups necessary for structural interaction with proteins, e.g., hydrogen bonding, and can include at least an amine, carbonyl, hydroxyl or carboxyl group, or at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents, also referred to herein as "test agents") are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

An agent of interest which modulates a sulfotransferase activity of a subject polypeptide decreases the activity at least about 10%, at least about 15%, at least about 20%, at least about 25%, more preferably at least about 50%, more preferably at least about 100%, or 2-fold, more preferably at least about 5-fold, more preferably at least about 10-fold or more when compared to a suitable control.

Agents that decrease a sulfotransferase or other activity of a subject polypeptide to the desired extent may be selected for further study, and assessed for cellular availability, cytotoxicity, biocompatibility, etc. For example, a candidate agent is assessed for any cytotoxic activity it may exhibit toward a eukaryotic cell, using well-known assays, such as trypan blue dye exclusion, an MTT ([3-(4,5-dimethylthiazol-2-yl)-2,5-diphenyl-2 H-tetrazolium bromide]) assay, and the like. Agents that do not exhibit cytotoxic activity toward eukaryotic cells are considered candidate agents for use in therapeutic methods for treating a mycobacterial infection.

Cell-free assays

Cell-free assay methods generally comprise:

a) contacting a test agent with a sample containing a mycobacterial sulfation pathway polypeptide; and b) assaying an activity of the mycobacterial sulfation pathway polypeptide in the presence of the substance. An increase or a decrease in the measured activity in comparison to the activity in a suitable control (e.g., a sample comprising a mycobacterial sulfation pathway polypeptide in the absence of the substance being tested) is an indication that the substance modulates an activity of the mycobacterial sulfation pathway polypeptide.

Cell-free assays may be designed in a number of ways. In some embodiments, a mycobacterial sulfation pathway polypeptide (e.g. M-ST) is combined with $^{35}$S-labeled sulfate donor such as [$^{35}$S]-PAPS, a candidate inhibitor compound ("a test agent"), and an acceptor molecule, which may be a natural or synthetic GL, GPL, or a simple nucleophile capable of accepting sulfate (such as phenolic compounds, and the like). The amount of [$^{35}$S]-sulfate transferred to the acceptor by the candidate agent is then determined by counting the acceptor-associated radioactivity or product quantitation with an antibody specific for the sulfated acceptor, or in a suitable scintillation proximity assay format.

An "agent which inhibits a sulfotransferase activity of a mycobacterial sulfotransferase polypeptide", as used herein, describes any molecule, e.g. synthetic or natural organic or inorganic compound, protein or pharmaceutical, with the capability of altering a sulfotransferase activity of a sulfotransferase polypeptide, as described herein. Generally a plurality of assay mixtures is run in parallel with different agent concentrations to obtain a differential response to the various concentrations. Typically, one of these concentrations serves as a negative control, i.e. at zero concentration or below the level of detection. Sulfotransferase activity can be measured using any assay known in the art.

A variety of other reagents may be included in the screening assay. These include reagents like salts, neutral proteins, e.g. albumin, detergents, etc that are used to facilitate optimal protein-ligand binding and/or reduce non-specific or background interactions. Reagents that improve the efficiency of the assay, such as protease inhibitors, nuclease inhibitors, anti-microbial agents, etc. may be used.

The above screening methods may be designed a number of different ways, where a variety of assay configurations and protocols may be employed, as are known in the art. For example, one of the components may be bound to a solid support, and the remaining components contacted with the support bound component. The above components of the method may be combined at substantially the same time or at different times. Incubations are performed at any suitable temperature, typically between 4° and 40° C. Incubation periods are selected for optimum activity, but may also be optimized to facilitate rapid high-throughput screening. Typically between 0.1 and 1 hours will be sufficient. Following the contact and incubation steps, the subject methods will generally, though not necessarily, further include a washing step to remove unbound components, where such a washing step is generally employed when required to remove label that would give rise to a background signal during detection, such as radioactive or fluorescently labeled non-specifically bound components. Following the optional washing step, the amount of incorporated sulfate will then be detected.

Cell-based assays

Cell-based assay generally involve contacting a cell that produces a mycobacterial sulfation pathway polypeptide with a test agent, and determining the effect, if any, on an activity of the peptide.

In some embodiments, a cell is a mycobacterial cell that produces the mycobacterial sulfation pathway polypeptide endogenously, or a cell, such as a mycobacterial cell, that is transformed with nucleic acid molecule that comprises a nucleotide sequence encoding a mycobacterial sulfation pathway polypeptide. The cell is grown in a culture medium in the presence of a labeled sulfate (e.g., $^{35}SO_4$) and the test agent. After a period of time, such as 30 minutes, 1 hour, 2 hours, 4 hours, or 12 hours, an extract of the cells is prepared, and the amount of radioactivity in a sulfated GL or GPL is measured, e.g., using thin-layer chromatography or other technique.

Genetic complementation assay

In some embodiments, a genetic complementation assay is provided. In these embodiments, a mutant bacterial cell that does not express a sulfation pathway gene (e.g., by virtue of being knocked out) is used. In some embodiments, a bacterial cell other than a mycobacterium is used. The mutant bacterium serves as a control, and is kept alive by providing necessary nutrients, and the like. A test bacterium is the mutant bacterium that has been genetically transformed with a nucleic acid that includes a sequence that encodes a functional mycobacterial sulfation pathway protein that the bacterium (e.g., by virtue of the knock-out, i.e., a genetic defect) lacks, thereby complementing the defect. The test bacterium and the control bacterium are individually contacted (e.g., in separate cultures) with a test agent. A test agent that kills the test bacterium, but not the control bacterium, is a candidate anti-mycobacterial agent. Viability of the bacterium is determined using standard methods, e.g., measuring the optical density of a culture grown in a liquid medium.

Thus, in some embodiments, the invention provides a method for identifying an agent that inhibits a mycobacterial sulfation pathway gene (e.g., inhibits transcription of the gene or translation of a corresponding mRNA) or gene product. The method generally involves contacting a test mutant bacterium and a control mutant bacterium with a test agent. The mutant bacterium does not produce a polypeptide encoded by the mycobacterial sulfation pathway gene by virtue of a genetic defect and that has been genetically transformed with a construct that includes a nucleotide sequence that encodes the mycobacterial sulfation pathway gene product, thereby genetically complementing the genetic defect. The control mutant bacterium includes the same mutation as the test mutant bacterium, but is not genetically complemented. The control mutant bacterium is maintained in medium that provides a component that keeps the bacterium alive despite the genetic defect. The effect of the test agent on the viability of the test mutant bacterium and the control mutant bacterium is determined. A decrease in the viability of the test mutant bacterium, and no decrease in the viability of the control mutant bacterium, indicates that the test agent is a candidate anti-mycobacterial agent.

This screening method can be generally applied to any mycobacterial sulfation pathway gene for which a knockout strain of another organism can be found and that satisfies three conditions: (1) The knockout or mutant organism is unable to survive under some or all conditions; (2) The knockout organism may be kept alive by genetic complementation with a gene supplied from another organism, the organism of interest (usually, but not necessarily, on a plasmid); and (3) The knockout organism may be kept alive through the administration of or supplementation by some external agent or agents.

External agents may include a substrate or compound that the knockout cell may be able to utilize to restore function; but may also include a second complementation gene that may work by a method unrelated to that of the first complementation gene to keep the knockout organism alive. The condition given in (3) functions as the control and the condition given in (2) functions as the experimental organism.

Thus, in some embodiments, the invention provides a method of identifying an agent that inhibits an activity of a mycobacterial sulfation pathway enzyme. The method generally involves culturing a first and a second bacterial cell in separate cultures in the presence of a test agent. The first and second bacterial cells contain a defect in a sulfation pathway enzyme, and the second bacterial cell has been transfected with a polynucleotide comprising a nucleotide sequence that encodes a mycobacterial sulfation pathway enzyme that complements the defect. After a suitable period of time, the growth of the first bacterial cell and the growth of the second bacterial cell are compared, e.g., the number of bacteria in the first culture is compared with the number of bacteria in the second culture (e.g., by measuring optical density of the cultures). A slower rate of growth in the second culture, compared with the growth rate of the first culture, indicates that the agent specifically inhibits the mycobacterial sulfation pathway enzyme.

A suitable period of time for growing the bacteria is generally from about 1 hour to about 2 hours, from about 2 hours to about 4 hours, from about 4 hours to about 8 hours, from about 8 hours to about 16 hours, from about 16 hours to about 24 hours, from about 24 hours to about 36 hours, from about 36 hours to about 48 hours, or from about 48 hours to about 72 hours. Typically, the bacteria are grown (cultured) at a temperature of about 37° C.

A reduction in growth of the second culture, relative to the first culture, indicates that the agent specifically inhibits the mycobacterial sulfation pathway enzyme. Generally, a reduction of at least about 10%, at least about 20%, at least about 25%, at least about 30%, at least about 40%, at least about 50%, at least about 60%, at least about 70%, at least about 80%, or at least about 90%, or more, of the second culture, compared to the growth of the first culture, indicates that the test agent inhibits the mycobacterial sulfation pathway enzyme and is therefore a candidate agent for treating a mycobacterial infection. For example, after a suitable time in culture, if the $A_{600}$ of the second culture is reduced by at least about 10%, at least about 20%, at least about 25%, at least about 30%, at least about 40%, at least about 50%, at least about 60%, at least about 70%, at least about 80%, or at least about 90%, compared to the $A_{600}$ of the first culture, then the test agent is of interest as a candidate agent for treating mycobacterial infection.

Figure 22:
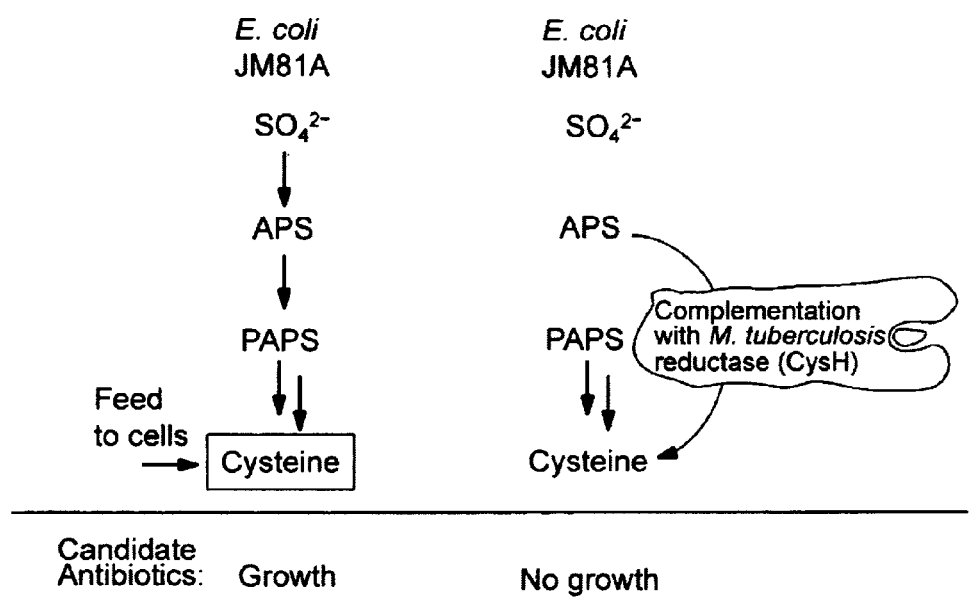
FIG. 22 depicts a screen for inhibitors of APS reductase and APS kinase.

The following is one non-limiting example of such an assay. To discover inhibitors of mycobacterial APS reductase and APS kinase, the genetic complementation system described in Example 4 is used. The screening method is shown schematically in FIG. 22.

Survival or death of these *E. coli* mutant strains grown in minimal media is used in a real-time assay system. Specifically, the complementation plasmids bearing the CysH and CysC genes described above allows *E. coli* JM81A to survive in minimal media using sulfate as the sole sulfur source through complementing the defective pathway in this strain. The knockout strain may be used as a control, being kept alive by the administration of either cysteine or methionine, thereby bypassing the defective pathway. Test compounds are administered to each, namely the complemented strain and the control strain, and the strains monitored for survival by measuring their cell density (usually absorbance measured on a spectrophotometer at 600 nm wavelength). An example of such an assay is shown in FIG. 23.

There are four possible outcomes.
(1) Both the complemented strain and the control strain survive,
(2) both strains die;
(3) the complemented strain dies and the control strain lives; or
(4) the complemented strain lives while the control strain dies.

In case (1) the compound has no activity. In case (2) the compound is not selective in its activity. In case (4) the compound has no activity against the gene borne on the complementation plasmid. However, in case (3), whatever factor the compound is acting upon in the complemented strain differs from that in the control strain. In this case it is likely that the compound is actually acting to inhibit the gene or gene product borne on the complementation plasmid. Thus, compounds that give a response corresponding to outcome (3) represent lead compounds that are likely to be inhibitors of APS kinase or APS reductase. These compounds should have the desirable properties of selectivity (being active against only the gene in question among all of the other essential genes in *E. coli*, and also of being bioavailable, that is they are able to enter the cell (in this case *E. coli*) and to act on the desired target.

THERAPEUTIC METHODS

Methods of treating a mycobacterial infection

The invention further provides methods of treating a mycobacterial infection in an individual. The methods generally involve administering to an individual a therapeutically effective amount of an agent that reduces a level and/or an activity of a mycobacterial sulfation pathway polypeptide, wherein the agent contacts a mycobacterium in the individual and reduces viability and/or virulence of the mycobacterium.

An agent that reduces a level and/or activity of a mycobacterial sulfation pathway polypeptide is administered to an individual in a therapeutically effective amount. As used herein, a "therapeutically effective amount" of an agent that reduces an activity and/or a level of a mycobacterial sulfation pathway polypeptide is an amount that is sufficient to reduce viability and/or virulence by at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or more, compared to the viability and/or virulence of the mycobacterium not contacted with the agent.

Whether an agent reduces the viability and/or virulence of a mycobacterium can be readily determined by those skilled in the art using standard methods. The term "virulence" encompasses two features of a pathogenic organism: its infectivity (i.e., the ability to colonize a host) and the severity of the disease produced. Virulence can be expressed as the $LD_{50}$, i.e., the dose that will kill 50% of inoculated animals within a given time. Virulence can also be expressed as transmissibility, i.e., the ability of a bacterium to cause a demonstrable infection in a given animal host. Transmissibility is usually detected by culture methods. The dose required is the $ID_{50}$, the infection dose in 50% of animals. Virulence can also be expressed as communicability. Virulence can be tested using any known assay, including, but not limited to, mouse colony formation assay, in which the number of mycobacterial colonies in the lung of infected mice is counted at various time points after infection; and macrophage infectivity assays. Other laboratory animals such as rabbits and guinea pigs can also be used. Virulence can also be determined in a cell culture assay using macrophages. Bacteria are incubated with cultured macrophages and the number of bacteria that enter the macrophages determined by washing the macrophages, lysing them, culturing their contents on plates, and counting "colony forming units."

Methods of increasing an immune response to a mycobacterium

The invention further provides methods of eliciting an immune response to a pathogenic mycobacterium (e.g., a wild-type, virulent mycobacterium) in a host. The methods generally involve administering to a mammalian host a subject genetically altered mycobacterium (e.g., a subject genetically altered mycobacterium that is avirulent, that exhibits reduced virulence, or that is attenuated). The host mounts an immune response to the genetically altered mycobacterium. In embodiments of particular interest, the immune response provides protection against a virulent strain of mycobacterium.

In some embodiments, a subject avirulent mycobacterium that is administered is of the same species as the virulent mycobacterium, and an immune response is generated to both the avirulent and the virulent mycobacterium. In other embodiments, the avirulent mycobacterium is a different species than the virulent mycobacterium, and an immune response is generated to both the avirulent and the virulent mycobacterium. In some embodiments, administration of a subject avirulent mycobacterium elicits an immune response to more than one species of virulent mycobacterium.

A subject genetically altered mycobacterium is administered to a host. The term "virulent" in the context of mycobacteria refers to a bacterium or strain of bacteria that replicates within a host cell or animal at a rate that is detrimental to the cell or animal within its host range. More particularly virulent mycobacteria persist longer in a host than avirulent mycobacteria. Virulent mycobacteria are typically disease producing and infection leads to various disease states including fulminant disease in the lung, disseminated systemic milliary tuberculosis, tuberculosis meningitis, and tuberculosis abscesses of various tissues. Infection by virulent mycobacteria often results in death of the host organism. Typically, infection of guinea pigs is used as an assay for mycobacterial virulence. In contrast, the term "avirulent" or "attenuated" refers to a bacterium or strain of bacteria that either does not replicate within a host cell or animal within its host range, or replicates at a rate that is not significantly detrimental to the cell or animal.

Acceptable routes of administration include, but are not limited to, intramuscular, subcutaneous, intradermal, oral, inhalational (e.g., intranasal, oral, intratracheal), and the like. Typically, an immunogenic composition as described below is administered in a pharmaceutically acceptable formulation, using conventional routes of administration. Additional acceptable routes of administration are as discussed below for therapeutic agents.

In response to administration of a subject genetically altered mycobacterium, a host mounts an immune response to the genetically altered mycobacterium, and, in many embodiments, to virulent strains of mycobacterium. An immune response includes, but is not limited to, a humoral immune response, wherein mycobacteria-specific antibodies are produced; and a cellular immune response, in which mycobacteria-specific cytotoxic T lymphocytes (CTLs) are produced. Whether mycobacteria-specific antibodies and/or CTLs are produced can be determined using any known assay. Such assays are standard in the art.

In many embodiments, an immune response to a genetically altered mycobacterium provides immunoprotection against one or more virulent strains of mycobacteria. Whether an immune response is immunoprotective can be determined, e.g., in an experimental animal, by counting the number of virulent mycobacteria in the animal at various time points (e.g., 7 days, 2 weeks, 1 month, 2 months, and 6 months or longer) after challenge with a virulent strain of mycobacterium. An immune response is immunoprotective if the number of virulent mycobacterium in the animal is reduced by at least about 20%, at least about 30%, at least about 40%, at least about 50%, at least about 60%, at least about 70%, at least about 80%, or at least about 90%, or more, when compared with an animal that was not administered with the genetically altered mycobacterium before challenge with a virulent mycobacterial strain, where the comparison is made at the same time point after challenge.

INTRACELLULAR PATHOGEN INFECTIONS AMENABLE TO TREATMENT

The methods and compositions described herein can be used in the treatment or prevention of any of a variety of infections by a mycobacterial species. Of particular interest is the treatment and/or prevention of infection or disease by *M. tuberculosis*, *M. avium* (or *M. avium-intracellulare*), *M. leprae* (particularly *M. leprae* infection leading to tuberculoid leprosy), *M. kansasii*, *M. fortuitum*, *M. chelonae*, and *M. absecessus*. While treatment of humans is of particular interest, the methods of the invention can also be used to prevent intracellular pathogen infection or disease in non-human subjects. For example, *M. avium* causes lymphadenitis in slaughter pigs; *M. paratuberculosis* infection causes paratuberculosis, a tuberculosis-like disease that can result in great production losses in cattle, sheep and goats; and *M. bovis* is carried by cattle and can cause a tuberculin-like infection in humans.

Individuals amenable to treatment with an agent of the invention include any individual diagnosed with an active mycobacterial infection. Individuals amenable to treatment also include individuals deemed to be at risk of having an active mycobacterial infection. At risk individuals include, but are not limited to, individuals infected with human immunodeficiency virus.

Individuals to be vaccinated include individuals that have never been infected with a mycobacterium; and individuals who have a latent mycobacterial infection.

THERAPEUTIC AGENTS

The invention further provides an agent identified using a screening method of the invention. In many embodiments, an agent identified by a screening method of the invention reduces viability and/or virulence of a pathogenic mycobacterium. Whether an agent has activity in reducing viability and/or virulence of a pathogenic mycobacterium can be determined using any known assay.

In vitro cell cultures are accepted by those skilled in the art as assays for determining the susceptibility of *M. tuberculosis* and other mycobacteria to inhibitory compounds. See, e.g., Mor et al. (Antimicrobial Agents and Chemotherapy 39:2073–2077, (1975)). A variety of assays are known to mimic physiological conditions and these include, but are not limited to Mor, et al. (supra) and Mor et al., Antimicrobial Agents and Chemotherapy 38:1161–1164, 1994. In these assays, cells susceptible to infection by *M. tuberculosis*, other mycobacteria are placed in culture in vitro. There are a number of different cell types that can be used that are susceptible to intracellular pathogens, including, but not limited to, macrophages and monocytes. Mononuclear phagocytes can be obtained as established cells lines or as primary cells taken from a patient, where the patient cells are placed into culture and used within several months. Primary human monocytes, tissue monocyte-derived macrophages (MDMs) or myeloid cell lines including HL60, U937 or THP-1 cells can be used. Myeloid cell lines are known in the art and are readily available from the ATCC (American Type Culture Collection, Rockville Md.).

Peripheral blood mononuclear cells (PBMC) can be used to generate primary monocytes and MDMs. These cells are readily isolated from heparinized blood on Ficoll-sodium diatrizoate gradients (Pharmacia Fine Chemical, Piscataway, N.J.) or the like. PBMC are cultured in wells at about 1.5 to about $2.0 \times 10^6$ mononuclear cells/ml and the monocytes or MDMs subsequently purified by adherence to glass or plastic.

Isolated alveolar macrophages can be obtained using lung lavage collection methods well known in the art. For lavage methods and the isolation of alveolar macrophages from the bronchial lavage fluid see McGowan, et al. Lung 169:215–226, 1991 and McGowan, et al. Am. Rev. Respir. Dis. 127:449–455, 1983 respectively.

Suspensions of bacterial pathogen can be tested in broth culture initially, if necessary or desired, to determine whether or not a compound or compounds directly inhibit the growth of the pathogen in suspension culture. There are a number of suspension culture methods known in the art.

A test agent can also be tested for its ability to inhibit intracellular pathogens in tissue culture assays. In general, in these assays, the macrophages are placed in culture and incubated with the intracellular pathogen at an approximate cell to pathogen ratio of preferably at least 1:1 to about 1:5 cells:pathogen. For assays assessing *M. tuberculosis* infection, freshly adherent monocytes, 12 day-old adherent MDMs, or freshly adherent alveolar macrophages are incubated with *M. tuberculosis* or other pathogenic mycobacterium at a ratio of about 1:1 to about 1:5 (phagocyte:bacterium). For *M. tuberculosis*, e.g., the bacteria are incubated with the phagocyte for 2 hr at 37° C. in RPMI/HEPES media with 2.5% serum or human serum albumin (serum-free).

The cells are washed to remove non-adherent bacteria and monolayers are replated with RPMI containing 1% autologous serum (to maintain phagocyte viability but not to sustain extracellular growth of bacteria). A test agent is added about 24 hours later and mycobacterial growth in cell lysates is then assessed over the next several days either by the radiometric BACTEC system or by colony-forming units on agarose plates. In each experiment, growth is assessed relative to control monolayers where no drug has been added.

Those skilled in the art will recognize that there are other assays that could be used to assess growth inhibition including assays to differentiate between pathogen stasis or pathogen death by plating cell lysates onto or into media known to support growth of the particular pathogen.

Whether an agent reduces virulence can be determined using any known assay for virulence.

In some embodiments, an active agent of the invention inhibits a mycobacterial APS kinase and/or a mycobacterial APS reductase. In some embodiments, the subject compounds and compositions thereof comprise a secondary amine having a first, hetero-aromatic group and a second, aromatic or cyclic ester group. The first, hetero-aromatic group may comprise any substituted or unsubstituted carbon and nitrogen containing heteroaromatic group, any substituted or unsubstituted carbon, nitrogen and oxygen containing heteroaromatic group, or any substituted or unsubstituted carbon, nitrogen and sulfur containing heteroaromatic group. The second group may comprise any substituted or unsubstituted phenyl or other aromatic group, or any substituted or unsubstituted cyclic ester.

More specifically, the subject compounds may comprise a secondary amine having the structure:

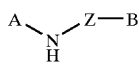

wherein A comprises a hetero-aromatic group, B comprises an aromatic group or a cyclic ester, and Z comprises a bi-functional moiety that links group B to the secondary amine nitrogen. The group Z may be omitted in certain embodiments.

By way of example, and not necessarily of limitation, the group A may comprise

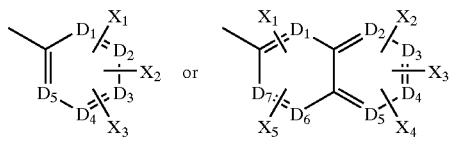

wherein $D_1$ through $D_7$ each may independently comprise either carbon or nitrogen, and $X_1$–$X_5$ each may independently comprise hydrogen or any functionality. The groups $X_1$–$X_5$ thus may each comprise, for example, hydrogen, alkyl, alkenyl, alkynyl, cycloalkyl, aryl, hetero-aryl, hydroxyl, alkoxyl, aryloxyl, amino, azido, alkylamino, halo, carboxyl, or other functional group, and stereoisomers, solvates, and pharmaceutically acceptable salts thereof.

In other embodiments, the group A may comprise:

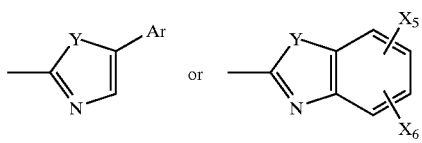

wherein Y is either oxygen or sulfur, and wherein $X_1$ and $X_2$ each may comprise hydrogen or any other functionality such as, for example, an alkyl, alkenyl, alkynyl, cycloalkyl, aryl, hetero-aryl, hydroxyl, alkoxyl, aryloxyl, amino, alkylamino, halo, carboxyl, or other group, and stereoisomers, solvates, and pharmaceutically acceptable salts thereof. In some of the specific embodiments discussed below, the group A comprises:

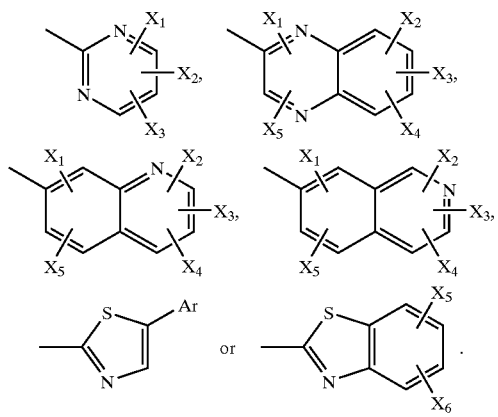

and wherein the groups $X_1$–$X_5$ each more specifically may comprise hydrogen, hydroxyl, methyl and/or alkylamino groups.

The group B may comprise, by way of example:

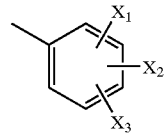

wherein $X_1$–$X_3$ each may comprise hydrogen or any functionality such as alkyl, alkenyl, alkynyl, cycloalkyl, aryl, hetero-aryl, hydroxyl, alkoxyl, aryloxyl, amino, azido, alkylamino, halo, carboxyl, or other functional group, and stereoisomers, solvates, and pharmaceutically acceptable salts thereof. In specific embodiments described below, the group B comprises a 4-aminophenyl, 4-azidophenyl, 3-hydroxyphenly, and a 2-carboxyphenyl group.

In still other embodiments, the group B may comprise:

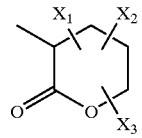

wherein $X_1$–$X_2$ each may independently comprise hydrogen or any functionality such as, for example, alkyl, alkenyl, alkynyl, cycloalkyl, keto, aryl, hetero-aryl, hydroxyl, alkoxyl, aryloxyl, amino, alkylamino, azido, halo, carboxyl, or other functional group, and stereoisomers, solvates, and pharmaceutically acceptable salts thereof. In a specific embodiment discussed below, the group B may comprise:

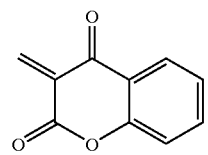

The group Z may comprise a methylene, aryl methylene, ethelyene, arylmethylene, ethelyene oxide, propylyene, propylene oxide, sulfone (-SO$_2$-), imido, keto, ether, thioether, ester, or any other group capable of linking the group B to the secondary amine functionality. In certain embodiments, the group Z may be omitted such that group B is directly joined or bonded to the secondary amine functionality.

More specifically, in certain embodiments a subject compound may comprise the following general formula:

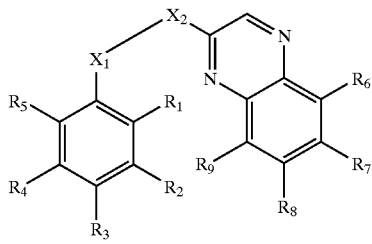

where $X_1$ and $X_2$ are each independently an ether (-O-), thioether (-S-), sulfone ($SO_2$-) -NH-, or -$CH_2$-, and where each of $R_1$–$R_9$ is independently a hydrogen, alkyl, alkenyl, alkynyl, cycloalkyl, keto, aryl, hetero-aryl, hydroxyl, alkoxyl, aryloxyl, amino, alkylamino, azido, halo, carboxyl, or other functional group; and stereoisomers, solvates, and pharmaceutically acceptable salts thereof.

In other embodiments, a subject compound may comprise the general formula:

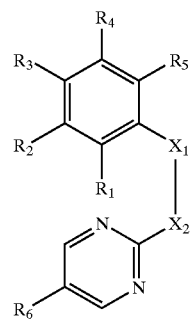

where each of $X_1$ and $X_2$ may independently comprise an ether (-O-), thioether (-S-), sulfone (-$SO_2$-), -NH-, or -$CH_2$-; and where each of $R_1$, $R_2$, $R_3$, $R_4$, $R_5$, and $R_6$ is independently a hydrogen, alkyl, alkenyl, alkynyl, cycloalkyl, keto, aryl, hetero-aryl, hydroxyl, alkoxyl, aryloxyl, amino, alkylamino, azido, halo, carboxyl, or other functional group; and stereoisomers, solvates, and pharmaceutically acceptable salts thereof.

In still other embodiments, a subject compound may have the generic formula:

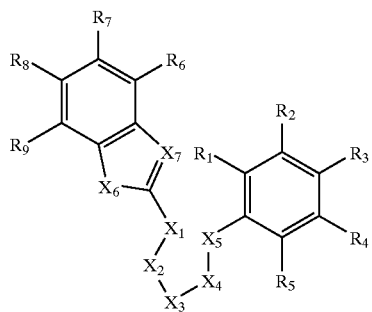

where each of $X_1$–$X_7$ may independently comprise an ether (-O-), thioether (-S-), sulfone (-$SO_2$-), N, -NH-, or -$CH_2$-; and where each of $R_1$–$R_9$ is independently a hydrogen, alkyl, alkenyl, alkynyl, cycloalkyl, keto, aryl, hetero-aryl, hydroxyl, alkoxyl, aryloxyl, amino, alkylamino, azido, halo, carboxyl, or other functional group; and stereoisomers, solvates, and pharmaceutically acceptable salts thereof.

In further embodiments, a subject compound may have the general formula:

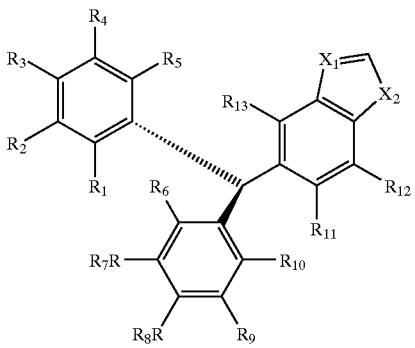

where each of $X_1$ and $X_2$ may independently comprise an ether (-O-), thioether (-S-), sulfone (-$SO_2$-), N, -NH-, or -$CH_2$-; and where each of $R_1$–$R_{13}$ is independently a hydrogen, carboxyl, alkyl, alkenyl, alkynyl, cycloalkyl, keto, aryl, hetero-aryl, hydroxyl, alkoxyl, aryloxyl, amino, alkylamino, azido, halo, or other functional group; and stereoisomers, solvates, and pharmaceutically acceptable salts thereof.

In other embodiments, a subject compound may have the general formula:

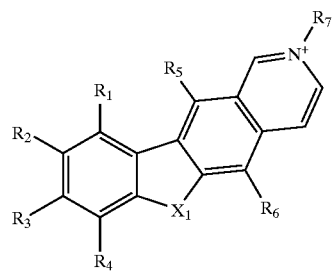

where X comprises N, C, O or S; and where each of $R_1$–$R_7$ is independently a hydrogen, carboxyl, alkyl, alkenyl, alkynyl, cycloalkyl, keto, aryl, hetero-aryl, hydroxyl, alkoxyl, aryloxyl, amino, alkylamino, azido, halo, or other functional group; and stereoisomers, solvates, and pharmaceutically acceptable salts thereof.

In other embodiments, a subject compound may have the general formula:

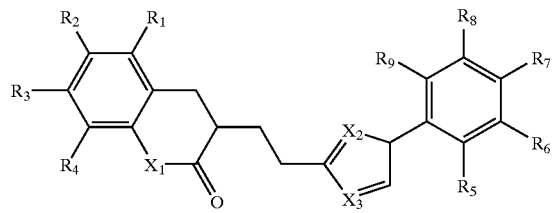

where each of $X_1$, $X_2$, and $X_3$ independently comprise C, N, O or S; and where each of $R_1$–$R_9$ is independently a hydrogen, alkyl, alkenyl, alkynyl, cycloalkyl, keto, aryl, hetero-aryl, hydroxyl, alkoxyl, aryloxyl, amino, alkylamino, azido, halo, carboxyl, or other functional group; and stereoisomers, solvates, and pharmaceutically acceptable salts thereof.

"Acyl" is a specie of heteroalkyl wherein a terminal carbon of the heteroalkyl group is in the form of a carbonyl group, i.e., (alkyl or heteroalkyl)-C=O, where examples include acetyl (CH$_3$-(C=O)-).

"Acyloxy" refers to a heteroalkylene group of the formula -C(=O)-O- bonded to "X" so as to form -C(=O)-O-X wherein X may be any of alkyl, aryl, heteroalkyl, or heteroaryl.

"Alkenyl" is a specie of alkyl group, where an alkenyl group has at least one carbon-carbon double bond.

"Alkenylene" is a specie of alkylene group where the alkylene group has at least one double bond.

"Alkyl" is a monovalent, saturated or unsaturated, straight, branched or cyclic, aliphatic (i.e., not aromatic) hydrocarbon group. In various embodiments, the alkyl group has 1–20 carbon atoms, i.e., is a C1–C20 (or $C_1$–$C_{20}$) group, or is a C1–C18 group, a C1–C12 group, a C1–C6 group, or a C1–C4 group. Independently, in various embodiments, the alkyl group: has zero branches (i.e., is a straight chain), one branch, two branches, or more than two branches; is saturated; is unsaturated (where an unsaturated alkyl group may have one double bond, two double bonds, more than two double bonds, and/or one triple bond, two triple bonds, or more than three triple bonds); is, or includes, a cyclic structure; is acyclic. Exemplary alkyl groups include $C_1$ alkyl (i.e., -CH$_3$ (methyl)), $C_2$ alkyl (i.e., -CH$_2$CH$_3$ (ethyl), -CH=CH$_2$ (ethenyl) and -C≡CH (ethynyl)) and $C_3$ alkyl (i.e., -CH$_2$CH$_2$CH$_3$ (n-propyl), -CH(CH$_3$)$_2$ (i-propyl), -CH=CH-CH$_3$ (1-propenyl), -C≡-C-CH$_3$ (1-propynyl), -CH$_2$-CH=CH$_2$ (2-propenyl), -CH$_2$-C≡CH (2-propynyl), -C(CH$_3$)=CH$_2$ (1-methylethenyl), and -CH(CH$_2$)$_2$ (cyclopropyl)).

"Alkylene" is a polyvalent, saturated or unsaturated, straight, branched or cyclic, aliphatic (i.e., not aromatic) hydrocarbon group. In various embodiments, the alkylene group has 1–20 carbon atoms, i.e., is a C1–C20 group, or is a C1–C18 group, a C1–C12 group, a C1–C6 group, or a C1–C4 group. Independently, in various embodiments, the alkylene group: has zero branches (i.e., is a straight chain), one branch, two branches, or more than two branches; is saturated; is unsaturated (where an unsaturated alkylene group may have one double bond, two double bonds, more than two double bonds, and/or one triple bond, two triple bonds, or more than three triple bonds); is or contains a cyclic group; is acyclic; is divalent, i.e., has two open sites that each bond to a non-alkylene group; is trivalent, i.e., has three open sites that each bond to a non-alkylene group; has more than three open sites. Exemplary alkylene groups include $C_1$ alkylene (i.e., -CH$_2$-) and $C_2$ alkylene (i.e., -CH$_2$CH$_2$-, -CH=CH-, -C≡C-, -C(=CH$_2$)-, and -CH(CH$_3$)-).

"Aralkenyl" is another name for arylalkenylene, wherein at least one of the open bonding sites of an alkenylene group is bonded to an aryl group.

"Aralkyl" is another name for arylalkylene, wherein at least one of the open bonding sites of an alkylene group is bonded to an aryl group, where benzyl is an example.

"Aryl" is a monovalent, aromatic, hydrocarbon, ring system. The ring system may be monocyclic or fused polycyclic (e.g., bicyclic, tricyclic, etc.). In various embodiments, the monocyclic aryl ring is C5–C10, or C5–C7, or C5–C6, where these carbon numbers refer to the number of carbon atoms that form the ring system. A C6 ring system, i.e., a phenyl ring, is an exemplary aryl group. In various embodiments, the polycyclic ring is a bicyclic aryl group, where exemplary bicyclic aryl groups are C8–C12, or C9–C10. A naphthyl ring, which has 10 carbon atoms, is an exemplary polycyclic aryl group.

"Arylene" is a polyvalent, aromatic hydrocarbon, ring system. The ring system may be monocyclic or fused polycyclic (e.g., bicyclic, tricyclic, etc.). In various embodiments, the monocyclic arylene group is C5–C10, or C5–C7, or C5–C6, where these carbon numbers refer to the number of carbon atoms that form the ring system. A C6 ring system, i.e., a phenylene ring, is an exemplary aryl group. In various embodiments, the polycyclic ring is a bicyclic arylene group, where exemplary bicyclic arylene groups are C8–C12, or C9–C10. A naphthylene ring, which has 10 carbon atoms, is an exemplary polycyclic aryl group. The arylene group may be divalent, i.e., it has two open sites that each bond to another group; or trivalent, i.e., it has three open sites that each bond to another group; or it may have more than three open sites.

"Cycloalkenyl" is a specie of alkyl group where a cycloalkenyl group is a cyclic hydrocarbon group with at least one double bond.

"Cycloalkenylene" is a specie of alkylene group which is a cyclic hydrocarbon with at least one double bond and with at least two bonding sites.

"Cycloalkyl" is a specie of alkyl group, where a cycloalkyl is a cyclic hydrocarbon group.

"Cycloalkylalkylene" is a species of alkyl group wherein at least one open bonding site of an alkylene group is joined to a cycloalkyl group.

"Cycloalkylene" is a specie of alkylene group which is a cyclic hydrocarbon group with at least two open bonding sites.

"Cycloalkylenealkylene" is a specie of alkylene group wherein a cycloalkylene group is bonded to a non-cyclic alkylene group, and each of the cycloalkylene and non-cyclic alkylene group have at least one open bonding site.

Haloalkyl is a specie of heteroalkyl wherein at least one carbon of an alkyl group is bonded to at least one halogen.

"Halogen" refers to fluorine, chlorine, bromine and iodide. Fluorine and chlorine are exemplary halogens in compounds and compositions of the present invention.

Heteroalkylenearyl is a heteroalkylene group with at least one of its open bonding sites joined to an aryl group, where benzoyl (-C(=O)-Ph) is an example.

"Heteroalkyl" is an alkyl group (as defined herein) wherein at least one of the carbon atoms is replaced with a heteroatom. Exemplary heteroatoms are nitrogen, oxygen, sulfur, and halogen. A hetcroatom may, but typically does not, have the same number of valence sites as carbon. Accordingly, when a carbon is replaced with a heteroatom, the number of hydrogens bonded to the heteroatom may need to be increased or decreased to match the number of valence sites of the heteroatom. For instance, if carbon (valence of four) is replaced with nitrogen (valence of three), then one of the hydrogens formerly attached to the replaced carbon must be deleted. Likewise, if carbon is replaced with halogen (valence of one), then three (i.e., all) of the hydrogens formerly bonded to the replaced carbon must be deleted.

"Heteroalkylene" is an alkylene group (as defined herein) wherein at least one of the carbon atoms is replaced with a heteroatom. Exemplary heteroatoms are nitrogen, oxygen, sulfur, and halogen. A heteroatom may, but typically does not, have the same number of valence sites as carbon. Accordingly, when a carbon is replaced with a heteroatom, the number of hydrogens bonded to the heteroatom may need to be increased or decreased to match the number of valence sites of the heteroatom, as explained elsewhere herein.

"Heteroaralkenyl" is another name for heteroarylalkenylene, wherein at least one of the open bonding sites of an alkenylene group is bonded to a heteroaryl group.

"Heteroaralkyl" is another name for heteroarylalkylene, wherein at least one of the open bonding sites of an alkylene group is bonded to a heteroalkyl group.

"Heteroaryl" is a monovalent aromatic ring system containing carbon and at least one heteroatom in the ring. The heteroaryl group may, in various embodiments, have one heteroatom, or 1–2 heteroatoms, or 1–3 heteroatoms, or 1–4 heteroatoms in the ring.

Heteroaryl rings may be monocyclic or polycyclic, where the polycyclic ring may contained fused, spiro or bridged ring junctions. In one embodiment, the heteroaryl is selected from monocyclic and bicyclic. Monocyclic heteroaryl rings may contain from about 5 to about 10 member atoms (carbon and heteroatoms), e.g., from 5–7, or from 5–6 member atoms in the ring. Bicyclic heteroaryl rings may contain from about 8–12 member atoms, or 9–10 member atoms in the ring. The heteroaryl ring may be unsubstituted or substituted. In one embodiment, the heteroaryl ring is unsubstituted. In another embodiment, the heteroaryl ring is substituted. Exemplary heteroaryl groups include benzofuran, benzothiophene, furan, imidazole, indole, isothiazole, oxazole, piperazine, pyrazine, pyrazole, pyridazine, pyridine, pyrimidine, pyrrole, quinoline, thiazole and thiophene.

"Heteroarylene" is a polyvalent aromatic ring system containing carbon and at least one heteroatom in the ring. In other words, a heteroarylene group is a heteroaryl group that has more than one open site for bonding to other groups. The heteroarylene group may, in various embodiments, have one heteroatom, or 1–2 heteroatoms, or 1–3 heteroatoms, or 1–4 heteroatoms in the ring. Heteroarylene rings may be monocyclic or polycyclic, where the polycyclic ring may contained fused, spiro or bridged ring junctions. In one embodiment, the heteroaryl is selected from monocyclic and bicyclic.

Monocyclic heteroarylene rings may contain from about 5 to about 10 member atoms (carbon and heteroatoms), e.g., from 5–7, or from 5–6 member atoms in the ring. Bicyclic heteroarylene rings may contain from about 8–12 member atoms, or 9–10 member atoms in the ring.

"Heteroatom" is a halogen, nitrogen, oxygen, silicon or sulfur atom. Groups, containing more than one heteroatom may contain different heteroatoms.

"Pharmaceutically acceptable salt" and "salts thereof" in the compounds of the present invention refers to acid addition salts and base addition salts.

Acid addition salts-refer to those salts formed from compounds of the present invention and inorganic acids such as hydrochloric acid, hydrobromic acid, sulfuric acid, nitric acid, phosphoric acid and the like, and/or organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

Base addition salts refer to those salts formed from compounds of the present invention and inorganic bases such as sodium, potassium, lithium, ammonium, calcium, magnesium, iron, zinc, copper, manganese,aluminum salts and the like. Suitable salts include the ammonium, potassium, sodium, calcium and magnesium salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamnine, ethanolamine, 2-dimethylaminoethanol, 2-diethylaminoethanol, trimethamine, dicyclohexylamine, lysine, arginine, histidine, caffeine, procaines, hydrabamine, choline, betaine, ethylenediamine, glucosamine, methylglucamine, theobromine, purines, piperazine, piperidine, N-ethylpiperidine, and the like.

Non-limiting examples of biologically active compounds are found in Example 5.

FORMULATIONS, DOSAGES, AND ROUTES OF ADMINISTRATION

Formulations

In the subject methods, the active agent(s) may be administered to a host using any convenient means capable of resulting in treatment of a mycobacterial infection.

Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

Other modes of administration will also find use with the subject invention. For instance, an agent of the invention can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), generally about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

An agent of the invention can be administered as injectables. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art See, e.g., Remington's Pharmaceutical Sciences, Mack Publishing Company, Easton, Pennsylvania, 17th edition, 1985. The composition or formulation to be administered will, in any event, contain a quantity of the agent adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Dosages

Although the dosage used will vary depending on the clinical goals to be achieved, a suitable dosage range is one which provides up to about 1 μg to about 1,000 μg or about 10,000 μg of an agent that treats a mycobacterial infection. Alternatively, a target dosage of a subject agent can be considered to be about in the range of about 0.1–1,000 μM, about 0.5–500 μM, about 1–100 μM, or about 5–50 μM in a sample of host blood drawn within the first 24–48 hours after administration of the agent.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

Routes of administration

A therapeutic agent is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, intratumoral, subcutaneous, intradermal, topical application, intravenous, rectal, nasal, oral and other parenteral routes of administration. Routes of administration may be combined, if desired, or adjusted depending upon the agent and/or the desired effect. The composition can be administered in a single dose or in multiple doses.

The agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

The agent can also be delivered to the subject by enteral administration. Enteral routes of administration include, but are not necessarily limited to, oral and rectal (e.g., using a suppository) delivery.

Methods of administration of the agent through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

Kits with unit doses of the active agent, e.g. in oral or injectable doses, are provided. In such kits, in addition to the containers containing the unit doses will be an informational package insert describing the use and attendant benefits of the drugs in treating pathological condition of interest. Preferred compounds and unit doses are those described herein above.

Combination therapies

In some embodiments, a therapeutic agent of the invention is administered in combination with a conventional anti-pathogenic agent in treatment of a mycobacterial infection. The additional anti-pathogenic agent may be any agent (e.g., chemotherapeutic agent) identified as having activity against the intracellular pathogen of interest (e.g., in inhibition of extracellular or intracellular growth stages of the intracellular pathogen (e.g., mycobacteria), enhancement of intracellular pathogen clearance (e.g., mycobacteria), etc.). Exemplary anti-pathogenic agents include, but are not necessarily limited to, antibiotics, including antimicrobial agents, (e.g., bacteriostatic and bacteriocidal agents (e.g., aminoglycosides, β-lactam antibiotics, cephalosporins, macrolides, penicillins, tetracyclines, quinolones, and the like), antivirals (e.g., amprenavirs, acyclovirs, amantadines, virus penciclovirs, and the like), and the like), antifungals, (e.g., imidazoles, triazoles, allylamines, polyenes, and the like), as well as anti-parasitic agents (e.g., atovaquones, chloroquines, pyrimethamines, ivermectins, mefloquines, pentamidines, primaquines, and the like). Where the subject being treated is particularly susceptible to infection by intracellular pathogens, including opportunistic pathogens, it may be desirable to administer a subject therapeutic agent in a combination therapeutic regimen with chemotherapeutic agents that exhibit activity against microbial and/or parasitic pathogens, e.g., antimicrobial agents, antiviral agents, antifungal agents, anti-parasitic agents, etc. Such combination therapies can involve simultaneous or consecutive administration of an anti-mycobacterial agent of the invention and such a chemotherapeutic agent(s).

Specific exemplary conventional anti-pathogenic/chemotherapeutic agents and combinatory therapies, particularly anti-mycobacterial agents and combinatory therapies, include, but are not necessarily limited to, clarithromycin (e.g., by oral administration or injection); capreomycin sulfate (e.g., by intramuscular injection or intravenous infusion, e.g., CAPASTAT®); ethambutol HCl (e.g., by oral administration of tablets or capsules, e.g.; MYAMBUTOL®); isoniazid (e.g., by intramuscular injection or oral administration, e.g., NYDRAZID®); aminosalicylic acid (e.g., aminosalicyclic acid granules for oral administration, e.g., PASER® GRANULES); rifapentine (e.g., by oral administration; e.g., PRIFTIN®); PYRAZINAMIDE (e.g., by oral administration); rifampin (e.g., by oral administration, e.g., RIFADIN®, or by intravenous administration, e.g., RIFADN IV®); rifampin and isoniazid combination therapy (e.g., by oral administration, e.g., RIFAMATE®); rifampin, isoniazid, and pyrazinamide combination therapy (e.g., by oral administration, e.g., RIFATER®); cycloserine (e.g., by oral administration, e.g., SEROMYCIN®); streptomycin sulfate (e.g., by injection or oral administration); ethionamide (e.g., by oral administration, e.g., TRECATORO®-SC), and the like.

The anti-pathogenic/chemotherapeutic agent and therapeutic agent of the invention can be administered within the same or different formulation; by the same or different routes; separately, simultaneously, or consecutively. The therapeutic agent can be delivered according to a regimen (e.g., frequency during a selected interval (e.g., number of times per day), delivery route, etc.) that is the same as, similar to, or different from that of the anti-pathogenic agent. When administered in combination, a therapeutic agent of the invention and an anti-pathogenic agent are generally administered within about 96 hours, about 72 hours, about 48 hours, about 24 hours, about 12 hours, about 8 hours, about 4 hours, about 2 hours, about 1 hour, or about 30 minutes or less, of each other. Thus, although it may be desirable to do so in some situations, it is not necessarily required that the therapeutic agent of the invention and an anti-pathogenic agent (e.g., antibacterial agent) be delivered simultaneously.

Vaccines

As discussed above, a subject genetically altered mycobacterium (e.g., a genetically modified mycobacterium that is avirulent, that has reduced virulence, or that is attenuated) finds use in immunogenic compositions, to elicit an immune response to a pathogenic mycobacterium. In many embodiments, a subject genetically altered mycobacterium elicits an immune response to a pathogenic mycobacterium, thereby providing immunoprotection against a pathogenic mycobacterium. Formulations, dosages, and routes of administration for the subject genetically altered mycobacteria are any conventional formulations, dosages, and routes of administration currently in use in mycobacteria (e.g., BCG) vaccines. Whether a subject genetically altered mycobacterium is effective in eliciting an immunoprotective immune response can be determined by administering the subject mycobacterium to a test animal, and, after a period of time, challenging the animal with a pathogenic strain of mycobacterium.

The invention provides immunogenic compositions comprising a genetically altered mycobacterium of the invention. When they are used to induce or enhance an immune response, the genetically modified mycobacteria of the present invention are administered to an individual using known methods. They will generally be administered by the same routes by which conventional (presently available) vaccines are administered and/or by routes which mimic the route by which infection by the pathogen of interest occurs. They can be administered in a composition which includes, in addition to the mutant mycobacterium, a physiologically acceptable carrier. The composition may also include an immunostimulating agent or adjuvant, flavoring agent, or stabilizer.

A subject immunogenic composition is administered in an "effective amount" that is, an amount of genetically altered mycobacterium that is effective in a selected route of administration to elicit or induce an immune response to the mycobacterium.

In some embodiments, an effective dose or a unit dose of immunogenic composition is in a range of from about $10^2$ to about $10^7$, from about $10^3$ to about $10^6$, or from about $10^4$ to about $10^5$ genetically altered mycobacteria. An optimal amount for a particular vaccine can be ascertained by standard studies involving observation of antibody titers and other responses in subjects. The levels of immunity provided by the immunogenic composition can be monitored to determine the need, if any, for boosters. For example, following an assessment of antibody titers in the serum and/or counting the number of mycobacterium in a sample from the individual, optional booster immunizations may be desired. The immune response to a subject genetically modified mycobacterium may be enhanced by the use of adjuvant and or an immunostimulant.

In some embodiments, a composition comprising the genetically altered mycobacterium is administered using conventional devices including but not limited to syringes, devices for intranasal administration of compositions, and vaccine guns. Thus, one embodiment of the present invention is a device comprising a member which receives the genetically altered mycobacterium (or composition comprising the genetically altered mycobacterium) in communication with a mechanism for delivering the immunogenic composition to the subject.

Compositions comprising a genetically modified mycobacterium of the invention may include a buffer, which is selected according to the desired use of the attenuated mycobacterium, and may also include other substances appropriate to the intended use. Those skilled in the art can readily select an appropriate buffer, a wide variety of which are known in the art, suitable for an intended use. In some instances, the composition can comprise a pharmaceutically acceptable excipient, a variety of which are known in the art and need not be discussed in detail herein. Pharmaceutically acceptable excipients have been amply described in a variety of publications, including, for example, Remington's Pharmaceutical Sciences, A. R. Gennaro editor (latest edition) Mack Publishing Company; A. Gennaro (2000) "Remington: The Science and Practice of Pharmacy", 20th edition, Lippincott, Williams, & Wilkins Pharmaceutical Dosage Forms and Drug Delivery Systems (1999) H. C. Ansel et al., eds 7$^{th}$ ed., Lippincott, Williams, & Wilkins; and Handbook of Pharmaceutical Excipients (2000) A.H. Kibbe et al., eds., 3$^{rd}$ ed. Amer. Pharmaceutical Assoc.

When used as an immunogenic composition, a genetically altered mycobacterium of the invention can be formulated in a variety of ways. In general, an immunogenic composition of the invention is formulated according to methods well known in the art using suitable pharmaceutical carrier(s) and/or vehicle(s). A suitable vehicle is sterile saline. Other aqueous and non-aqueous isotonic sterile injection solutions and aqueous and non-aqueous sterile suspensions known to be pharmaceutically acceptable carriers and well known to those of skill in the art may be employed for this purpose.

Optionally, an immunogenic composition of the invention may be formulated to contain other components, including, e.g., adjuvants, stabilizers, pH adjusters, preservatives and the like. Such components are well known to those of skill in the vaccine art. Adjuvants include, but are not limited to, aluminum salt adjuvants (Nicklas (1992) *Res. Immunol.* 143:489–493); saponin adjuvants; Ribi's adjuvants (Ribi ImmunoChem Research Inc., Hamilton, Mont.); Montanide ISA adjuvants (Seppic, Paris, France); Hunter's TiterMax adjuvants (CytRx Corp., Norcross, Ga.); Gerbu adjuvants (Gerbu Biotechnik GmbH, Gaiberg, Germany); and nitrocellulose (Nilsson and Larsson (1992) *Res. Immunol.* 143:553–557). In addition, other components that may modulate an immune response may be included in the formulation, including, but not limited to, cytokines, such as interleukins; colony-stimulating factors (e.g., GM-CSF, CSF, and the like); and tumor necrosis factor.

The invention further provides kits comprising a subject immunogenic composition in a pharmaceutically acceptable formulation, packaged in a sterile container or a sterile delivery device. In some embodiments, a sterile vial containing lyophilized subject genetically altered mycobacteria is provided. A separate vial containing a suspension base for reconstituting lyophilized genetically altered mycobacteria may also be provided. Typically, a kit contains a sterile vial containing a unit dosage form, e.g., an amount of genetically modified mycobacteria suitable for a single dose. The sterile vial may be a syringe. Additional components include needles. Package inserts containing information on the use of a subject kit may also be provided.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations are used, e.g., min (minutes); h (hours); s (seconds); U (Units); and the like.

EXAMPLE 1

Protocol For Generating *M. tuberculosis* Targeted Knockouts

Using H37Rv genomic DNA as a template and a polymerase chain reaction (PCR), amplify ~2 kilobase DNA sequences that directly flank the gene of interest. Subclone these fragments into the pNIL vector multiple cloning site. Using a restriction site present in pNIL that is placed between the two inserted flanking genomic fragments, subclone the hyg marker. This marker can be amplified-by PCR from a hyg vector with primers that add the unique site used for insertion into pNIL. Next, digest the pNIL vector that is now carrying a marked interrupted allele of the gene, with Pac I. This digestion will linearize the plasmid. In parallel, digest the pGOAL vector with Pac I. Purify the ~6 kB product resulting from this digestion. This fragment contains the counter selectable marker, SacB, as well as another marker, β-galactosidase. Subelone this cassette into the Pac I-linearized pNIL. The knockout plasmid is now complete.

In order to increase recombination efficiency, irradiate ~2 μg of the knockout plasmid with ultraviolet light. Immediately transform, by electroporation, an aliquot of competent H37Rv with the irradiated DNA. For the first selection, plate the transformation on hygromycin+kanamycin. Colonies that appear on this plate should be single crossover homologous recombinants. A small percentage of these colonies may be the result of illegitimate recombination. Remove colonies from this plate and plate again on media containing sucrose, bygromycin and X-gal. White colonies that grow on this plate are primarily double crossover homologous recombinants and thus the interrupted allele of the gene should have replaced the wild type allele. See, e.g., Parish and Stoker (2000) *Microbiology* 146(8):1969–75.

EXAMPLE 2

Phage Method for Generating *M. tuberculosis* Targeted Knockouts

Another method has recently become available for generating site-specific mutations in *M. tuberculosis.* This new method uses a genetically modified version of the mycobacterial phage, TM4, to introduce an interrupted allele of the target gene at a much higher frequency than that obtainable by electroporation. The phage transduction efficiency is high enough to directly screen for double crossover homologous recombinants.

Genomic DNA is isolated from colonies harvested at the last stage of selection. The presence of the interrupted allele can be screened using PCR or by southern blot analysis. See, e.g., Glickman et al. (2000) *Molecular Cell* 5(4):717–27.

Example 3

Identification of Mycobacterial sulfate assimilation proteins

Materials and Methods

Pfu DNA polymerase was obtained from Stratagene. Restriction enzymes were from NEB (New England Biolabs) or Amersham-Pharmacia Biotech. Calf intestinal alkaline phosphatase (CIAP) was from Amersham-Pharnacia Biotech. Plasmid miniprep kits and the QIAquick kit for DNA extraction from agarose gel were from Qiagen. T4 DNA ligase was from NEB. Plasmids used in this work are shown in Table 1.

TABLE 1

Bacterial strains and plasmids used in this study.

| Strain or plasmid | Relevant characteristics |
|---|---|
| *E. coli* strains | |
| JM81A | cysC92, tfr-8 |
| JM96 | thr-1, leuB6, lacY1, glnV44(AS), gal-6, $\lambda^-$ $^{\text{trp-1,}}$ hisG1(Fs), rfbD1, cysH56, galP63, $\Delta$(gltB-gltF)500, rpsL9, malT1($\lambda^R$), xylA7, mtlA2, $\Delta$argH1, thi-1 |
| BL21(DE3) | $F^-$ ompT $r_B^- m_B^-$ |
| DH5$\alpha$ | supE44, thi-1 $\Delta$lacU169(f80lacZ$\Delta$M15) endA1 recA1 hsdR17 gyrA96 relA1 |
| *M. smegmatis* strains | |
| mc²155::cysH | cysH deletion strain, Hyg$^r$ |
| mc²155::cysC | cysC deletion strain, Hyg |
| Plasmids | |
| pUC18/RBS | *E. coli* expression vector, Amp$^r$ |
| pUC18/RBS/BioB | pUC18/RBS containing *E. coli* bioB gene |
| pUC18/RBS/CysH | pUC18/RBS containing *M. tuberculosis* cysH gene |
| pUC18/RBS/CysC | pUC18/RBS containing putative cysC C-terminal fragment of *M. tuberculosis* cysNC gene |

Amp$^r$ and Kan$^r$ denote resistance to ampicillin and kanamycin, respectively.

Oligonucleotide primers are shown in Table 2. Sequences in bold indicate restriction sites.

TABLE 2

| Sequence | SEQ ID | Name |
|---|---|---|
| 5'-GATATACATATGAGCGGCGAGACAACCAGGC-3' | (SEQ ID NO:33) | MTCYSHF2 |
| 5'-GTGGTGCTCGAGCGAGGCGTGCAACCCG-3' | (SEQ ID NO:34) | MTCYSHR2 |
| 5'-AAGGGGCATATGAGCCCGAACACGGTGC-3' | (SEQ ID NO:35) | MTCYSCF |
| 5'-AAGGGGCTCGAGTTAAGACGATGACTCCAACAGGTC-3' | (SEQ ID NO:36) | MTCYSCR |
| 5'-GGGGCCATGGGTAGCGGCGAGACAACCAGG-3' | (SEQ ID NO:37) | CYSHPUCF |
| 5'-GGGGGGATCCCTCGAGTTACGAGGCGTGCAACCCG-3' | (SEQ ID NO:38) | CYSHPUCR |
| 5'-GGGGCCATGGGTAGCCCGAACACGGTGC-3' | (SEQ ID NO:39) | CYSCPUCF |
| 5'-GGGCCATGGGGACCGACGTGACGACGTCAACG-3' | (SEQ ID NO:40) | pUCMsHFor |
| 5'-GGGGCTCGAGTCACGAGACGTGCAGCCCGC-3' | (SEQ ID NO:41) | pUCMsHRev |
| 5'-GGGGAACCATGGGTTTAACGTATGATAATTGGGAAG-3' | (SEQ ID NO:42) | pUCCYSHBsF |
| 5'-GGGGAACTCGAGTTATTCATGCAGTCCGC-3' | (SEQ ID NO:43) | pUCCYSHBsR |
| 5'-GTGCTGGTGCCCGCGATCGGGCCCTTGCTGAGCACCGT-3' | (SEQ ID NO:44) | MTKONC5MF |
| 5'-ACGGTGCTCAGCAAGGGCCCGATCGCGGGCACCAGCAC-3' | (SEQ ID NO:45) | MTKONC5MR |
| 5'-TATTCTATCAAGCTTCACGAGATCGGCACCGATCAG-3' | (SEQ ID NO:46) | CysHKO#1 |
| 5'-AGATCATAGGTACCGATCAACCCGATCGCGGCGTGG-3' | (SEQ ID NO:47) | CysHKO#2 |
| 5'-CTTATTATGGTACCCTCGTCGGTCCAGCGCAGCAGC-3' | (SEQ ID NO:48) | CysHKO#3 |
| 5'-TAGATAATGCGGCCGCCGGTGTGTAGGTGTTGAAGTC-3' | (SEQ ID NO:49) | CysHKO#4 |
| 5'-GGGGTTAATTAACATGAGCGGCGAGACAACCAGG-3' | (SEQ ID NO:50) | CYSHPMSF |
| 5'-GGGGGGATCCCGAGGCGTGCAACCCG-3' | (SEQ ID NO:51) | CYSHPMSR |

Preliminary sequence data for *M. smegmatis* and *M. avium* were obtained from The Institute for Genomic Research website. *E. coli* JM81A and JM96 were obtained from the *E. coli* genetic stock center (CGSC), Yale University, USA.

Cloning of cysH and cysC genes from genomic DNA
Preparation of pET vectors

The gene encoding CysH (cysH) was amplified by the polymerase chain reaction (PCR) and subcloned into pCR4Blunt-TOPO. The PCR mixture contained 10 µM oligonucleotide primers (MYCYSHF2 and MTCYSHR2), 0.25 mM concentrations of the four deoxynucleotide triphosphates in 50 µl of Pfu polymerase buffer, 10% dimethylsulfoxide, and 100 ng of *M. tuberculosis* genomic DNA. After heating to 95° C., the reaction was initiated by adding 5 Units (U) of Pfu DNA polymerase. The PCR was performed in a thermal cycler (Perkin Elmer, GeneAmp PCR System 2400). The following PCR program was used: 25 cycles (20 seconds (s) at 94° C., 30 s at 50° C., and 55 s at 72° C.) and then incubation for 7 min at 72° C. Agarose gel electrophoresis of the PCR mixture revealed a single DNA fragment of approximately 500 bp. This fragment was cut from the gel and purified using the QIAquick kit.

The product was ligated into pCR4Blunt-TOPO according to the manufacturer's instructions (Invitrogen). Isolated colonies were grown overnight in liquid media and plasmid DNA isolated by miniprep. Plasmids containing insert were identified by restriction digest and confirmed by sequencing. The insert was excised by digestion with NdeI/XhoI, separated by agarose gel electrophoresis and purified using the QIAquick kit. The product was ligated into the NdeI/XhoI digested pET24b(+) vector (treated with CIAP) using T4 DNA ligase. After incubation at 16° C. for 2 hours (h), 8 µl of the reaction mixture was used to transform 100 µl of *E. coli* DH5α. After growth on LB amp, colonies were selected and grown overnight. Plasmid DNA minipreps were screened by restriction digest to afford pET24b(+)CysH.

The C-terminal portion of the cysNC gene was amplified from genomic DNA using primers MTCYSCF and MTCYSCR and cloned into pCR4Blunt-TOPO as above. After sequencing, the insert was excised from this vector by digestion with NdeI/XhoI and ligated into CIAP treated NdeI/XhoI digested pET28b(+) to afford pET28b(+)CysC.
Preparation of complementation vectors The gene encoding CysH (cysH) was amplified from the pET24b(+)CysH vector described above using primers CYSHPUCF and CYSHPUCR and cloned into pCR4Blunt-TOPO as above. After sequencing, the insert was excised by digestion with NcoI/BamHI and ligated into CLAP treated NcoI/BamHI digested pUC18/RBS, to generate pUC18/RBS/MtCysH.

The gene encoding CysC (cysC) was amplified as above using primers CYSCPUCF and MTCYSCR and cloned into pCR4Blunt-TOPO as above. After sequencing the insert was excised from this vector by digestion with NcoI/XhoI and the two fragments generated were separated by gel electrophoresis and purified as above. The longer NcoI/XhoI fragment was ligated into NcoI/XhoI digested pUC18/RBS/MtCysH from above and transformed into E. coli DH5α. Colonies containing the correct insert were verified by restriction digest. This vector was digested with NcoI and treated with calf intestinal alkaline phosphatase and ligated to the second NcoI/NcoI fragment. After transformation and plasmid isolation, the plasmid minipreps were screened for correctly oriented insert with EagI/XhoI, affording pUC18/RBS/MtCysC.

The gene encoding the M. smegmatis CysH(cysH) was amplified from M. smegmatis mc²155 genomic DNA using primers pUCMsHFor and pUCMsHRev and cloned into pCR4Blunt-TOPO as above. After sequencing, the insert was excised by digestion with NcoI/XhoI and ligated into CIAP treated NcoI/XhoI digested pUC18/RBS to yield pUC18/RBS/MsCysC.

The gene encoding the B. subtilis CysH (cysH) was amplified from pBS170 using primers pUCCYSHBsF and pUCCYSHBsR and cloned into pCR4Blunt-TOPO as above. After sequencing, the insert was excised by digestion with NcoI/XhoI and ligated into CIAP treated NcoI/AhoI digested pUC18/RBS to yield pUC18/RBS/BsCysH.

The S103G mutant of CysC in pUC18/RBS/CysC was generated using the QuikChange protocol from Stratagene. Briefly, two mutagenic primers MTKONC5MF and MTKONC5MR were used to amplify the template. Agarose gel electrophoresis was used to confirm that the reaction was successful. After the amplification reaction, DpnI was added to the reaction mixture and the mixture incubated at 37° C. for 1 h. 1 µl of the reaction mixture was used to transform 50 µl of super-competent E. coli XL1-Blue (Stratagene). The cells were grown on LB amp and, after miniprep of plasmid DNA, restriction digest with BanI (the mutagenic primers introduce a silent mutation creating a BanI restriction site) was used to identify mutants. These were sequenced to confirm the desired insert, affording PUC18/RBS/CysCS 103G.
Genetic Complementation E. coli JM81A and JM96 were grown in Oxoid CM1 media (1 g Oxoid Lab Lemco powder, 2 g yeast extract, 5 g peptone, 5 g NaCl per liter). Plasmid DNA was transformed into cells by electroporation (Bio-Rad Gene-Pulser, following the manufacturers protocol). Transformants were grown on CM1 agarose containing 100 mg/l ampicillin before transfer to M9 minimal media supplemented with thiamin (0.0005%), mannitol (0.2%), glucose (0.2%), and 18 amino acids excluding cysteine and methione (each 25 mg/L) and containing $MgSO_4$ (0.01%) as sole sulfur source. SDS-PAGE of crude, whole-cell extracts was used to confirm the constitutive expression of CysC, CysC S103G, and CysC PS103G from their respective plasmids in E. coli JM81A.
Construction of CysH M. smegmatis deletion mutant The cysH deletion mutant was constructed using the allelic replacement method of Parish and Stoker ((2000) Microbiol. 146:1969–1975). Oligonucleotide primers were used to amplify 2 kB regions upstream and downstream of the cysH gene. The upstream region was generated using primers CysHKO#3 and CysHKO#4, which generate a NotI/KpnI fragment and the downstream region was generated using primers CysHKO#1 and CysHKO#2, which generate a KpnI/HindIII fragment. The PCR products were gel purified and digested with the relevant restriction enzymes and ligated into a similarly digested p2NIL vector that was pre-treated with calf intestinal alkaline phosphatase. A hygromycin resistance marker was inserted between the two fragments into the KpnI restriction site. The final delivery vector, p2NIL_MsCysH was generated by adding the PacI cassette ($_{PAg8}$5-lacZ $_{Phsp6}$0-sacB) from pGOAL17 to the vector bearing the mutated allele. This cassette contains the lacZ reporter gene and the sacB negative selection marker. sacB, encoding levan sucrase, confers toxicity to the cell when grown on sucrose containing media. The delivery vector was pretreated with UV light (120 mJ $cm^{-2}$ and used to electroporate M. smegmatis mc²155.

Transformants were selected on Middlebrook 7H11 media containing 20 mg $L^{-1}$ kanamycin and 50 mg $L^{-1}$ hygromycin. After 5 days colonies were tested for the presence of the lacZ gene and positive colonies were grown in 7H9 media containing 50 mg $L^{31}$ $^1$hygromycin overnight. Serial dilutions were plated onto 7H11 plates containing 2% sucrose, 50 mg $L^{-1}$, and X-gal 50 mg $L^{-1}$. Colonies that did not turn blue were tested for kanamycin sensitivity and were then subjected to genotypic analysis. The construction of the cysC deletion mutant has been described elsewhere.
Genotypic analysis DNA was prepared from colonies by standard methods. Southern blotting analysis was carried out by generating two probes, one specific for the upstream region of the gene and one specific for the downstream region. Genomic DNA was digested with restriction enzymes that generated unique bands for the wildtype and mutant strains.
Construction of mycobacterial complementation vectors Complementation of the mutant strain was performed using the vector pMS3GS. This vector was constructed by inserting a 400 bp region containing the M. tuberculosis glutamine synthetase promoter into pMS3. A cloning site was introduced that allowed the cloning of a PacI-BamHI fragment. The M. tuberculosis cysH gene was amplified from genomic DNA using CYSHPMSF and CYSHPMSR and cloned into pCR4-TOPO as described above. After sequencing, the insert was excised from this vector by digestion with PacI/BamHI and ligated into CIAP treated PacI/BamHI digested pMS3GS to afford pMS3GSMtCysH.
Growth curves The growth rates of cultures of wildtype and mutant strains of M. smegmatis were determined in 7H9 Middlebrook media that contained 0.05% Tween 80, 20 mg $L^{-1}$ kanamycin and 2 mM methionine. Cultures were inoculated at 0.05 $OD_{600}$ and were own with shaking (250 rpm) at 37° C.
Expression of M. tuberculosis CysC pET28b(+)CysC was transformed into BL21 STAR and grown on LB agarose containing 50 mg/ml kanamycin. An isolated colony was picked and grown in 2 ml of LB media containing 50 mg/ml kanamycin. When this culture had reached an $A_{600}$=0.5, 1 ml was used to inoculate 500 ml of 2YT media containing 50 mg/ml kanamycin. The culture was grown at 37° C. with shaking until an $A_{600}$=0.5, then the suspension was cooled to 20° C. and IPTG added to a final concentration of 0.4 mM. The culture was allowed to grow overnight. Cells were collected by centrifugation (10 min at 4000 rpm), and suspended in lysis buffer (20 mM Tris buffer containing 100 mM NaCl and 10 mM imidazole) before disruption by ultrasonication. The cell lysate was cleared by centrifugation (10 min at 10000 rpm), and the supernatant applied to a column of NiNTA agarose resin and eluted with 20 mM Tris buffer (pH 7.8) containing 100 mM NaCl and a gradient of imidazole up to 250 mM. The fractions containing protein were concentrated and stored in the same buffer. Total yield was approximately 25 mg of protein per liter of culture. Further characterization was performed using a Perkin-Elmer Sciex API III electrospray mass spectrometer that gave a mass of 23192 Da. This compares satisfactorily with the calculated mass predicted for the protein with the loss of the N-terminal methionine (calc. 23168). Protein concentrations were measured using the Pierce Micro BCA analysis kit.

Assay of MtCysC

Kinetic parameters were measured at 25° C. using a 50 rnM Tris buffer (pH 8.0) containing 1 mM KCl and 0.1% bovine serum albumin. Each sample contained 700 µL of buffer, 25 U of lactate dehydrogenase and 35 U of pyruvate kinase (from rabbit muscle, 50% suspension in glycerol), 25 U of P1 nuclease, 100 µL of 50 mM ATP, 5mM $MgCl_2$ and 100 mM Tris base and varying amounts of APS. Prior to the addition of APS kinase, the background rate was measured and typically was 0.001 $A_{340}$ units per min. Measurements were started by addition of MtCysC. Measurements of the decrease of absorption at 340 nm per min in a continuous assay yielded reaction rates using an extinction coefficient for NADH of 6.22 $mM^{-1}$ $min^-$. The decrease was linear during all measurements. The concentration of APS was determined by measuring the total change in absorbance at 340 nm in a reaction catalyzed by APS kinase catalyzed but omitting $P_1$ nuclease. Michaelis parameters ($V_{max}$ and Km) were extracted from this data by best fit to the Michaelis-Menten equation using the program Grafit (Leatherbarrow, R. J., Erithacus Software, Staines). $K_m$ and $V_{max}/E_0$ values were obtained by measuring rates in a series of cells at a range of substrate concentrations (6–10 concentrations) which encompassed the $K_m$ value ultimately determined, generally from $0.2 \times K_m$ to $5 \times K_m$.

RESULTS

The *M. tuberculosis* H37Rv gene sequence annotated as CysH (Rv2392) was identified in the original publication of the genome. The amino acid sequence of the protein encoded by this gene is provided in FIG. 14. We have discovered homologs of this gene in the genomes of other Mycobacterial species, namely *M. avium* and *M. smegmatis* $mc^2$155. The amino acid sequence of the protein encoded by the CysH gene in *M. smegmatis* is provided in FIG. 15. The amino acid sequences of the protein encoded by-the CysH gene in *M. avium* is provided in FIG. 16. An alignment of the amino acid sequences of the protein encoded by the CysH gene in *M. tuberculosis* ("Myctub"), *M. avium* ("Mycavi"), and *M. smegmatis* ("Mycsme") is shown in FIG. 17. Additionally, sequences identical to that seen in *M. tuberculosis* H37Rv were seen in other members of the *M. tuberculosis* complex including *M. tuberculosis* CDC1551 and *M. bovis* BCG. These sequences were identified by the use of the BLAST algorithm. Our searches for homologs have thus far been confined to organisms for which a genomic sequencing project is underway or has already been completed.

We used genetic complementation in specific *E. coli* knockout strains to define the substrate specificity of two of these CysH homologs. In this approach, *E. coli* strains defective in known places in their pathway for sulfate assimilation may be used as an experimental organism. The two *E. coli* strains used in this study were JM96 and JM81 A and were obtained from the *E. coli* Genetic Stock Center (CGSC). The complete phenotypes of these organisms are shown in Table 1, above.

The genes for CysH of *M. tuberculosis* H37Rv and *M. smegmatis* $mc^2$155 were amplified from genomic DNA using the polymerase chain reaction and ligated into a pUC18-based plasmid with a lac promoter that allowed constitutive expression in these knockout strains. The plasmid was introduced into the two knockout strains by transformation and selection on media containing ampicillin. Resistance to ampicillin is conferred by the complementation plasmid. The complementation assay and results are shown in FIG. 18. The complemented strains were grown on minimal media containing sulfate as sole sulfur source. The original *E. coli* mutant strains are unable to grow on such media. In both cases, the CysH genes from *M. tuberculosis* H37Rv and *M. smegmalis* $mc^2$155 allowed the two mutant strains to survive, thereby confirming that these genes encode for APS reductases. High levels of identity between these two genes and the corresponding gene for CysH that we identified in *M. avium*, in particular the presence of conserved CCXXXKXXXL (SEQ ID NO:53) and CXXC (SEQ ID NO:54) motifs (see FIG. 17) lead us to the conclusion that the CysH gene of this organism that we have identified also encodes for an APS reductase.

This result allows us to redefine the sulfate assimilation pathway of *M. tuberculosis* and other Mycobacteria. Accordingly, the Mycobacteria APS reductase gene acts on APS to provide sulfite, which eventually is incorporated into cysteine and methionine. The APS kinase gene, which forms the carboxyl-terminal portion of Rv1286 and which we have demonstrated to be active, also acts on APS to produce PAPS. PAPS is produced for the use of this organism's sulfotransferases. Consequently, inhibition of the APS reductase will prevent the formation of cysteine and methionine. On the other hand, inhibition of APS kinase will prevent the formation of PAPS and, it follows, the formation of sulfated metabolites through the action of the sulfotransferases of this organism.

In order to confirm the presence of a functional APS kinase in *M. tuberculosis*, the carboxyl-terminal domain of Rv1286 (CysN/CysC) was amplified by PCR and subcloned into the complementation vector described above. This plasmid was transformed into the *E. coli* knockout strain JM81A (which contains a knockout of APS kinase). When grown on minimal media containing sulfate as sole sulfur source, the complementation plasmid bearing this portion of the CysN/CysC gene enabled the survival of this strain. This result confirms that *M. tuberculosis* possesses a functional APS kinase and shows that it Is encoded for by the carboxyl-terminal domain of this protein. We searched for homologs of CysC in other, sequenced members of the Mycobacteria, namely *M. smegmatis* and *M. avium* and in both cases identified genes with high levels of homology that we expect to contain APS kinases.

The amino acid sequence of the protein encoded by the CysN/CysC gene of *M. smegmatis* is shown in FIG. 19. The amino acid sequence of the protein encoded by the CysN/CysC gene of *M. avium* is shown in FIG. 20.

Identification of cysH, cysC and cysN homologs in *M. tuberculosis* and *M. smeginatis* cysH and cysC Homologs were identified in *M. tuberculosis* and *M. smegmatis* by BLAST analysis and in the former case correspond to the annotated sequences in the published genome. Interestingly, amino acid sequence comparison of these CysH proteins shows that they align well with both PAPS and APS reductases from a variety of organisms. However, the mycobacterial CysH proteins each contain two pairs of cysteine residues in the C-terminal half of the sequence. These two pairs of cysteine residues are common to all the known APS reductases and are absent in all but one of the proven PAPS reductases (that of *Bacillus subtilis*, vide infra).

The *M. tuberculosis* CysC gene is fused to the C-terminus of CysN, the GTPase that forms a heterodimer with CysD. This is not uncommon, for example, similar fusions are found in the functionally equivalent NodQ genes of *S. meliloti* and in CysN/CysC of *Pseudomonas aeruginosa*. Unlike these organisms, *M. tuberculosis* contains only single copies of each domain of cysH, cysC, and cysN, thereby representing a much simpler sulfate assimilation system than that of many other bacteria. The CysN/CysC protein overlaps the CysD protein by 4 nucleotides and appears to be part of the same operon. A putative RBS upstream of the start of CysN/CysC was located that lies within the C-terminus of the preceding gene, CysD.

Functional complementation of *E. coli* CysC and CysH knockout strains

Given the large degree of sequence similarity between the PAPS and APS reductases, we chose to confirm the function of the *M. tuberculosis* and *M. smegmatis* cysH genes using genetic complementation in *E. coli*. The cysH genes were amplified by PCR from genomic DNA using primers complementary to the N-and C-termini. The PCR products were ligated into a pUC18-based vector containing a ribosomal binding site (RBS) upstream of the insertion point. Owing to the high copy number of the pUC18 plasmid in *E. coli* (>100 copies per cell) and the !ow copy number of the lac repressor protein (approximately 10 per cell), this plasmid allows the constitutive expression of proteins in the absence of a chemical inducer. The plasmids bearing the *M. tuberculosis* and *M. smegmatis* cysH genes were separately transformed into *E. coli* JM81A (a mutant strain lacking APS kinase) and JM96 (a mutant strain lacking PAPS reductase), and grown on ampicillin containing CM 1 medium (a rich medium able to support the growth of these knockout *E. coli* strains). Isolated colonies were plated onto M9 minimal media supplemented with 18 amino acids (not cysteine or methionine), containing sulfate as the sole metabolizable sulfur source.

Complementation of JM96, an *E. coli* strain capable of the synthesis of PAPS but not its reduction, confirms that the gene product either has PAPS or APS reductase activity. Complementation of JM81A, an *E. coli* strain capable of the synthesis of APS, but not PAPS, shows that the gene must encode an APS reductase. pUC18/RBS/MtCysH and pUC18/RBS/MsCysH were able to complement both *E. coli* JM81A and JM96 strains to cysteine prototrophy. This result is consistent with the *M. tuberculosis* and *M. smegmatis* cysH encoding APS reductases. The assignment of APS reductase activity to both the *M. tuberculosis* and *M. smegmatis* CysH enzymes is in agreement with the observation that all proven APS reductases contain two pairs of conserved cysteine residues.

However, as noted above, there is one CysH, that from *B. subtilis*, that has been assigned PAPS reductase activity that contains these same two pairs of cysteines. We were concerned with the assignment of this gene product as a PAPS reductase, which was made on the basis of its ability to complement the *E. coli* mutant JM96, a strain lacking in PAPS reductase. While the ability to restore this strain to cysteine prototrophy is consistent with the gene product being a phosphosulfate reductase, it does not show whether the enzyme is an APS or PAPS reductase. Consequently, we obtained the plasmid used in the original study by Mendoza and colleagues, pBS170, and confirmed its ability to complement JM96, but also tested its ability to complement JM81A. Interestingly, we were able to repeat the original result of Mendoza and coworkers with JM96 but found that the plasmid did not restore prototrophy to JM81A. However, of particular concern here was the low growth rate seen with JM96. While colonies could be seen on plates with JM96 transformed with pUC18/RBS/MtCysH after 24h growth, similar sized colonies with JM96 transformed with pBS170 took around 48 h to appear. It was thought that the expression of the *B. subtilis* gene could be limiting from the pBluescript SKII(+) vector, particularly as this construct used the native *B. subtilis* PBS (−14 to −8, AGGAGAA) (Mansilla and deMendoza (1997) *J. Bacteriol* 179:976–981). Consequently, we subcloned the *B. subtilis* cysH into the pUC18/RBS vector (which uses a typical *E. coli* RBS, −13 to −8, AGGAGG) and tested it for its ability to complement JM96 and JM81A. Both mutant cell lines were transformed to cysteine prototrophy, thereby confirming an APS reductase activity of the *B. subtilis* enzyme.

Identification of an active CysC domain

We recently showed that *M. tuberculosis* possesses three open reading frames with high levels of homology to the sulfotransferase gene family. In this work we have shown that in *M. tuberculosis* APS is used directly for the production of sulfite; it appears that PAPS is produced for the sole use of these putative sulfotransferases. Given this newly defined sulfate assimilation pathway for *M. tuberculosis*, we were interested in generating a functional knockout of PAPS biosynthesis in this organism, and thereby of all the sulfotransferases. Consequently, we identified APS kinase, CysC, as a possible target for generating a functional knockout of PAPS biosynthesis and therefore of all sulfotransferase activity in *M. tuberculosis*. As discussed above, CysC is fused to CysN, thereby complicating the generation of a knockout.

In order to construct a defined knockout of CysC, the APS kinase domain of CysN/CysC needed to be identified. We decided to confirm the identification of the CysC domain by using genetic complementation. The C-terminal domain of CysN/CysC was identified by alignment to the CysN and CysC proteins of *E. coli*. According to our analysis, the CysN and CysC domains of *M. tuberculosis* are separated by a short linker with the sequence TPST. The C-terminal domain of CysN/CysC was amplified from genomic DNA and the product was subcloned into pUC18/RBS and tested for its ability to complement the *E. coli* strain JM81A. Transformation of this strain with the plasmid restored it to cysteine prototrophy. With a complementation system in hand for detecting alterations in function of CysC, we focused on generating a single point mutant incapable of complementing *E. coli* JM81A with the aim of establishing a method for the generation of a CysC knockout, without disrupting CysN. Our approach was inspired by the results of Satischandran et al. Satischandran et al. (1989) *J. Biol. Chem.* 264:15012–15021; and Satischandran et al. (1992)

Biochem. 31:11684–11688. These workers found that upon incubation of the E. coli CysC with γ$^{32}$P-ATP in the absence of APS, the enzyme was radiolabeled. Upon proteolysis, the radiolabelled peptide was isolated, and sequenced, indicating the presence of a phosphorylated serine, S109. On the basis of this result, these workers suggested that the enzyme mechanism of phosphoryl transfer proceeds through a covalent phosphoserine intermediate.

Consequently, we mutated the corresponding residue in the *M. tuberculosis* CysC, S103, to glycine. However, the plasmid bearing this mutation, pUC18/RBS/CysCS103G, still restored cysteine prototrophyto JM81A when grown on minimal media containing sulfate as sole sulfur source. This result, while surprising, was not entirely unexpected. Segel and coworkers found during studies with the closely related CysC from *Penicillium chrysogenum* that mutation of the corresponding serine residue (S107) in this enzyme to alanine gave a mutant with kinetic characteristics similar to the wild-type. MacRae et al. (1998) *J. Biol. Chem.* 273:28583–28589. While these workers identified other mutations in the phosphate binding loop of the *P. chrysogenum* CysC that abolished enzyme activity. *P. chysogenum* contains a second APS-like protein, with strong homology to CysC, that binds APS but has no kinase activity. This protein lacks both the conserved serine of APS kinases and contains several differences in the phosphate binding loop. Segel and coworkers showed that mutation of the *P. chrysogenum* CysC in the phosphate binding loop to the corresponding residues of the APS binding protein resulted in elimination of enzyme activity. In our case mutation of the phosphate binding loop of the *M. tuberculosis* S103G CysC mutant to the same residues as found in the *P. chrysogenum* APS binding protein generated a mutant protein that was unable to complement *E. coli* JM81A.

Construction of a CysH and CysC deletion mutant of *M. smegmatis*

To confirm the proposed route for sulfate assimilation of *M. smegmatis* we constructed two deletion mutants. The cysH and cysC genes were interrupted using the allelic replacement method of Parish and Stoker. Briefly, a delivery vector containing the interrupted allele was constructed in the suicide plasmid p2NIL by replacing the middle portion of the gene with a hygromycin resistance marker. After irradiation with UV light, a pre-treatment that has been shown to promote homologous recombination, the delivery vectors were transformed into *M. smegmatis* mc$^2$155 and kanamycin/hygromycin resistant colonies obtained. These colonies should be single crossovers that have integrated the suicide plasmid.

Putative single crossover colonies were grown in liquid media and then grown on media containing hygromycin, sucrose and X-gal. Sucrose acts as a negative selection marker and allows only those cells that have lost the sacB gene to grow. The loss of this gene is confirmed by the absence of the lacZ gene. Colonies that afforded colorless colonies represent potential knockouts and were confirmed by Southern analysis. The preparation of the cysC knockout was performed by a similar approach and will be reported elsewhere. These mutants were tested for auxotrophy in liquid media containing 2 mM cysteine or 2 mM methionine. In the case of the cysH deletion mutant, this strain was found to be both a cysteine and methionine auxotroph, thereby confirming the essentiality of the cysH gene for sulfate assimilation. However, the cysC mutant was not a methionine or cysteine auxotroph, a result consistent with our hypothesis that this gene is not required for the assimilation of sulfur into the sulfur containing amino acids. Further, complementation of the cysH knockout strain with the complementation plasmid pMS3GSMtCysH restored this strain to cysteine and methionine prototrophy, confirming the role of the *M. tuberculosis* cysH gene in the reduction of APS.

In vitro assay of *M. tuberculosis* CysC

CysC was cloned into pET28b(+) and over-expressed in *E. coli* as an N-terminal His$_x$6-fusion. Purification was achieved through affinity chromatography on NiNTA resin. The purified protein bad an apparent molecular weight of 23 kDa by SDS-PAGE and a MW as determined by ESI-MS of 23192 Da. This compares favorably with the predicted molecular weight of 23 168 Da for the protein with the loss of the N-terminal methionine, presumably effected by the endogenous methionyl aminopeptidase of the expression host. The enzyme was tested for its ability to phosphorylate APS using the coupled assay of Burnell and Whatley ((1975) *Anal. Biochem.* 68:281–288), with the modifications of Renosto et al. ((1984) *J. Biol. Chem.* 259:2113–2123). This assay allows the direct monitoring of rates by coupling the production of ADP (from ATP) to pyruvate kinase, and the lactate dehydrogenase catalyzed reduction of pyruvate by NADH. The decrease in the concentration of NADH maybe continuously monitored at 340 nm. P1 3'-nuclease is also included to regenerate APS from the product, PAPS, thereby enabling the measurement of very low $K_m$ values.

Using this assay, we measured an apparent $K_m$ value of $0.64\pm0.10$ μM and an apparent $V_{max}E_0$ value of $0.85\pm0.04$ s$^{-1}$ (for an apparent $V_{max}E_0/K_m$ 1334 mM$^{-1}$s$^{-1}$) for APS in the presence of saturating ATP (5 mM). In the presence of 75 mM sulfate, the apparent $K_m$ value increased nearly four-fold to $1.7\pm0.1$ μM with little change in the $V_{max}E_0$ value (1.05 s$^{-1}$) leading to a two-fold decrease in $V_{max}E_0$ (611 mM$^{-1}$s$^{-1}$). The higher $K_m$ value for the enzyme in 75 mM sulfate simplifies the kinetics somewhat and provides closer mimicry of the intracellular ionic strength. To confirm that the assay was being run at a saturating concentration of ATP, the kinetic parameters were measured in the presence of saturating APS (10 μM) in buffer containing 75 mM sulfate. The kinetic parameters confirmed that the concentration of ATP was saturating (apparent $K_m=0.91\pm0.10$ mM, apparent $V_{max}E_0=0.95\pm0.03$s$^{-1}$, apparent $(V_{max}E_0)/K_m=1.04$ mM$^{31}$ 1s$^{-1}$). This $K_m$ value is similar to that seen for the APS kinase of *E. coli* ($K_m=0.25$ μM). However, the *M. tuberculosis* enzyme differs from that of *E. coli* in that the former does not appear to suffer from the potent substrate inhibition seen for the latter (Satishchandran and Markham (2000) *Archiv. Biochem. Biophys* 378:210–215).

EXAMPLE 4

Figure 21A:
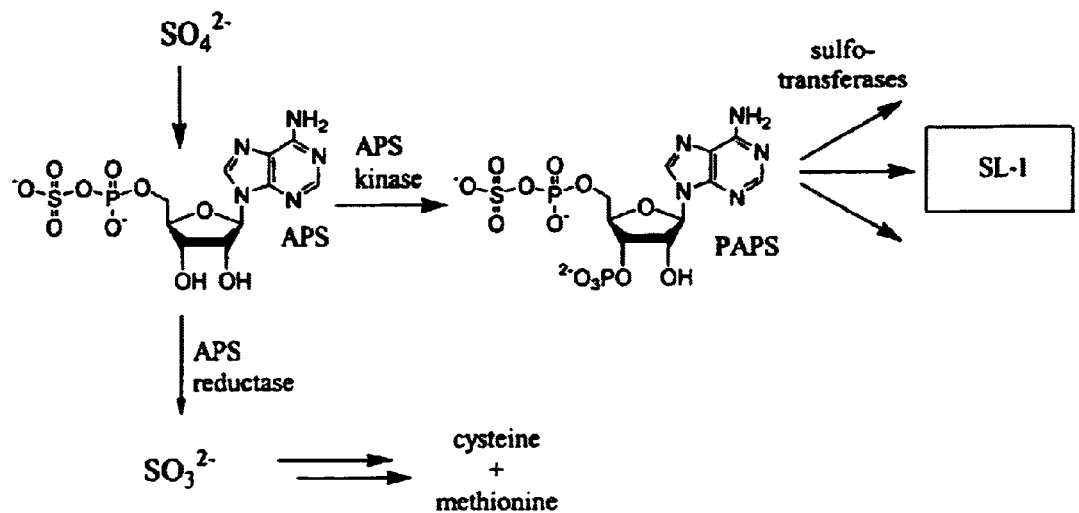
FIG. 21a depicts a sulfation assimilation pathway used by *M. tuberculosis, M smegmatis,* and *M. avium.
Figure 21B:
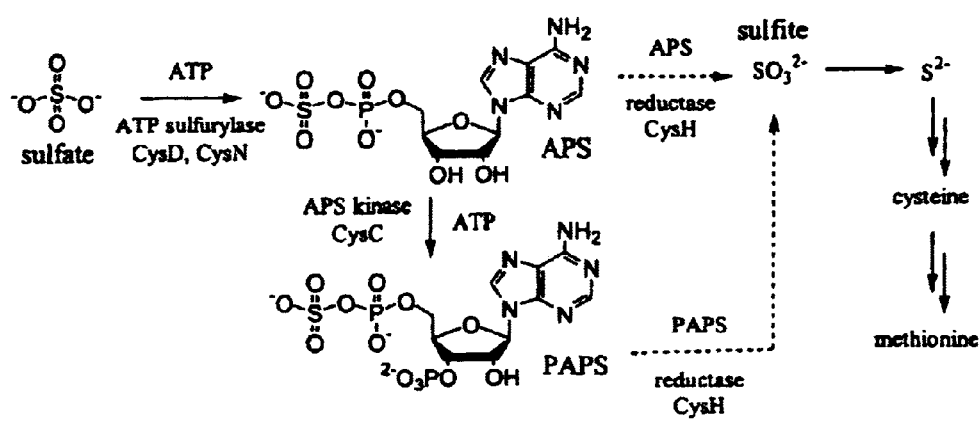
* FIG. 21b depicts sulfate assimilation pathways in plants and bacteria.

Screening method to identify inhibitors of mycobacterial APS reductase and APS kinase A sulfation assimilation pathway used by *M. tuberculosis, M. smegmatis,* and *M. avium* is shown in FIG. 21*a*. Sulfate assimilation pathways in plants and bacteria are shown in FIG. 21*b*. Common enzyme designations are given below each arrow in FIG. 21*b*.

To discover inhibitors of mycobacterial APS reductase and APS kinase, the above-described genetic complementation system is used. The screening method is shown schematically in FIG. 22.

Survival or death of these *E. coli* mutant strains grown in minimal media is used in a real-time assay system. Specifically, the complementation plasmids bearing the CysH and CysC genes described above allows *E. coli* JM81A to survive in minimal media using sulfate as the sole sulfur source through complementing the defective pathway in this strain. The knockout strain may be used as a control, being kept alive by the administration of either cysteine or methionine, thereby bypassing the defective pathway. Test compounds are administered to each, namely the complemented strain and the control strain, and the strains monitored for survival by measuring their cell density (usually absorbance measured on a spectrophotometer at 600 nm wavelength). An example of such an assay is shown in FIG. 23.

There are four possible outcomes.
(1) Both the complemented strain and the control strain survive,
(2) both strains die;
(3) the complemented strain dies and the control strain lives; or
(4) the complemented strain lives while the control strain dies.

These outcomes are depicted in Table 3.

TABLE 3

| Complemented strain | Control strain | Activity of test compound |
|---|---|---|
| Survive | Survive | No activity |
| Die | Die | Activity not selective |
| Die | Survive | Candidate selective inhibitor |
| Survive | Die | No activity against complementing gene or gene product |

In case (1) the compound has no activity. In case (2) the compound is not selective in its activity. In case (4) the compound has no activity against the gene borne on the complementation plasmid. However, in case (3), whatever factor the compound is acting upon in the complemented strain differs from that in the control strain. In this case it is likely that the compound is actually acting to inhibit the gene or gene product borne on the complementation plasmid. Thus, compounds that give a response corresponding to outcome (3) represent lead compounds that are likely to be inhibitors of APS kinase or APS reductase. These compounds should have the desirable properties of selectivity (being active against only the gene in question among all of the other essential genes in $E.\ coli$, and also of being bioavailable, that is they are able to enter the cell (in this case $E.\ coli$) and to act on the desired target.

This method is suitable as a first level screen as compounds that are identified may be causing outcome (3) by acting on other genes in the pathway, including the first step, production of APS that is catalyzed by ATP sulfurylase, or later steps such as the reduction of sulfite to sulfide, and the incorporation of sulfide into O-acetylserine to generate cysteine.

To determine the specificity of the inhibitor's action, a second complementation system may be used that operates in a different way to the first, enabling the determination of the compound's true site of action. In the case of the discovery of inhibitors of APS kinase and APS reductase, as these genes act in the same pathway, they can be used to determine the exact mode of action of an inhibitor. Thus, if an inhibitor acts only on one complemented strain, then this shows that it must act solely on that enzyme. Compounds that act on both strains must act on other enzymes in the pathway and themselves give a valuable indication of possible lead compounds for future screening efforts. As can be seen, this screen has many advantages for high-throughput screening given its simplicity and ease of scale-up.

EXAMPLE 5

Discovery of inhibitors of APS reductase and APS kinase

In order to discover inhibitors of these enzymes, we have made use of the genetic complementation system described in Example 4 to use survival or death of these $E.\ coli$ mutant strains grown in minimal media as a real-time assay system. Specifically, the complementation plasmids bearing the CysH and CysC genes described above allows $E.\ coli$ JM81A to survive in minimal media using sulfate as the sole sulfur source through complementing the defective pathway in this strain. The knockout strain itself may be used as a control, being-kept alive by supplementation with cysteine, thereby bypassing the defective pathway. Compounds from libraries may be administered to each strain, namely the complemented strain and the control strain, and the strains monitored for survival by measuring their cell density (usually absorbance measured on a spectrophotometer at 600 nm wavelength) (FIG. 23).

We used this complementation based screening approach to search for inhibitors of mycobacterial APS kinase and APS reductase. Strains bearing complementation plasmids were grown in M9 minimal media in 384 well plates. Using the High-throughput screening facility at the Institute of Chemistry and Chemical Biology at Harvard University, 18000 compounds were added to each of the two complemented strains and the control for a total of 54000 experiments. Compounds were transferred using robotic pin-transfer into each of the 384 well plates for a final concentration of 12–25 mg L$^{-1}$. Cells were then grown at 37° C. for two days before measuring their absorbance at 650 nm on a 384 well plate reader. Absorbance values for the experimental strains were converted into percentage inhibition relative to the reference strain. 50 compounds were found that gave a 40% or greater inhibition of growth on one or other experimental strain, but not on the control strain. These 50 compounds were cherry picked and the inhibition assay repeated on a larger scale to confirm the observed phenotype. Shown below are six of the most potent compounds detected so far.

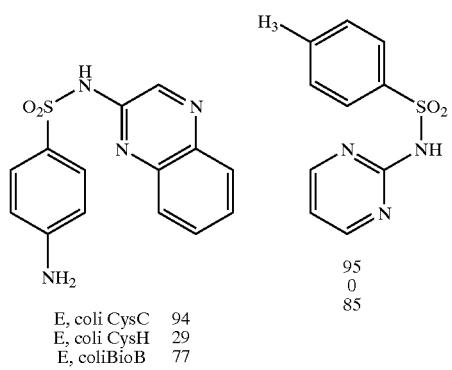

| | |
|---|---|
| E, coli CysC | 94 |
| E, coli CysH | 29 |
| E, coliBioB | 77 |

| | |
|---|---|
| | 95 |
| | 0 |
| | 85 |

[Structures shown with values:]

47
0
0

93
25
1

E, coli CysC  98
E, coli CysH  97
E, coliBioB    0

78
90
0

The values under each compound indicate the percent inhibition of growth of each complemented *E. coli* strain when grown in the presence of 25 μg/mL of each compound. *E. coli* CysC is JM81A complemented with *M. tuberculosis* CysC; *E. coli* CysH is JM81A complementaed with *M. smegmatis* CysH; *E. coli* BioB is JM81A control strain containing the BioB gene. 0% represents attenuation of growth or no inhibition of growth.

EXAMPLE 6

Sulfotransferase Knockout *M. tuberculosis* Strains

Individual *M. tuberculosis* mutant strains have been constructed that lack each of the sulfotransferases we identified: Rv2267c, Rv3529c, and Rv1373. The strains were generated following the method of Parish and Stoker. Parish, T. and N. G. Stoker (2000). "Use of a flexible cassette method to generate a double unmarked Mycobacterium tuberculosis tlyA plcABC mutant by gene replacement." *Microbiology* 146 (Pt 8): 1969–75. Briefly, PCR was used to amplify approximately 2 kB fragments of H37Rv genomic DNA flanking the sulfotransferase gene to be deleted. After digestion with appropriate restriction enzymes, these fragments were ligated into a vector with an antibiotic resistance marker insertion between them. This vector, carrying the interrupted allele of the sulfotransferase was transformed into *M. tuberculosis* H37Rv. After transformation, the cells were selected for homologous recombination between the plasmid and the genomic DNA. Sulfotransferase mutant strains were screened by southern blot hybridization analysis. We observed the expected pattern and molecular weight of bands in the Southern blot, thus confirming that Rv2267c had been deleted from the genome of *M. tuberculosis* H37Rv.

EXAMPLE 7

Assay for the Identification of Sulfated Molecules in Mycobacteria

An assay to search for sulfated compounds absent from the sulfotransferase mutant strains has been developed. The assay uses stable sulfur isotopic labeling and Fourier transform-ion cyclotron resonance mass spectrometry (FT-ICR MS) to quickly identify sulfur-containing compounds from crude lipid extracts of wild type *M. tuberculosis*. First, wild type *M. tuberculosis* is grown in minimal media containing either $Na_2^{32}SO_4$ or $Na_2^{34}SO_4$ as the sole sulfur source. In the cells grown with $Na_2^{34}SO_4$-containing media, compounds containing either sulfur or sulfate shift by 2.0 m/z x n, where n is the number of sulfur atoms. Comparison of these isotopically-labeled extracts drastically lowers the spectra complexity and facilitates the rapid identification of compounds containing sulfur. Once these few sulfur-containing compounds are identified, their presence or absence in the sulfotransferase mutant strains is determined. We have found empirically that the initial step using a stable isotope of sulfur to find sulfur-containing compounds is indispensable, although in only about 50% of the cases are these compounds found to be sulfated.

EXAMPLE 8

Genetic and Biochemical Evidence that Rv2267c is a Sulfotransferase

The assay described in Example 7 was used to search identified for a sulfated compound absent from the *M. tuberculosis* strain carrying the interrupted, nonfunctional Rv2267c allele. An ion carrying a single negative charge at m/z 881.6 was found shifted by 2.0 mass units when *M. tuberculosis* was incubated in $^{34}$S-containing medium. This same compound was found absent from the *M. tuberculosis* strain lacking Rv2267c (FIG. 24). Expression of the Rv2267c gene in the Rv2267c mutant returned the m/z 881 ion. This experiment, in combination with our bioinformatics analysis, shows that the Rv2267c gene product is a sulfotransferase responsible for sulfating the m/z 881.6 ion. Structural information is not yet available for the 881.6 compound; however preliminary data suggests it is a novel sulfated compound.

EXAMPLE 9

The CysH gene (APS reductase) in *M. tuberculosis* was deleted, and the effect of this deletion on the virulence of the commonly used H37Rv laboratory strain of *M. tuberculosis* was tested.

The cysH deletion mutant was constructed using the allelic replacement method of Parish and Stoker ((2000)

*Microbiology* 146(8):1969–75). Oligonucleotide primers were used to amplify 2 kB regions upstream and downstream of the cysH gene. The upstream region was generated using the primer pair MTKOH5F and MTKOH5R, which generates NotI/KpnI and KhindII/PmII fragments, respectively. The sequence of MTKOH5F is 5' TATTCTAT-CAAGCTTCACGAGATCGGCACCGATCAG 3' (SEQ ID NO:55). The sequence of MTKOH5R is 5' AGATCATAG-GTACCGATCAACCCGATCGCGGCGTGG 3' (SEQ ID NO:56). The downstream region was generated using primers MTKOH3F and MTKOH3R, which generate HindIII/ScaI and KpnI/NotI fragments. The sequence of MTKOH3F is CTTATTATGGTACCCTCGTCGGTC-CAGCGCAGCAGC 3' (SEQ ID NO:57). The sequence of MTKOH3R is 5' TAGATAATGCGGCCGCCGGTGTG-TAGGTGTTGAAGTC 3' (SEQ ID NO:58). The PCR products were gel purified and digested with the relevant restriction enzymes and ligated into a similarly digested p2NIL vector that was pre-treated with calf intestinal alkaline phosphatase (CIAP). A hygromycin resistance marker was inserted between the two fragments into the KpnI restriction site. The final delivery vectors, p2NIL_MtCysH and p2NIL_MtCysC were generated by adding the PacI cassette ($P_{Ag85}$-lacZ$P_{hsp60}$-sacB) from pGOAL17 to the vector bearing the mutated allele. This cassette contains the lacZ reporter gene and the sacb negative selection marker. sacB, which encodes levan sucrase, confers toxicity to the cell when grown on sucrose containing media. The delivery vector was pretreated with UV light (120 mJ cm$^{-2}$) and used to electroporate *M. tuberculosis* H37Rv. Transfonnants were selected on Middlebrook 7H11 medium containing 20 mg/l kanamycin and 50 mg/l hygromycin. After 3 weeks, colonies were tested for the presence of the lacZ gene and positive colonies were grown overnight in 7H9 medium containing 50 mg/l hygromycin. Serial dilutions were plated onto 7H11 plates containing 2% sucrose, 50 mg/l hygromycin, 2 mM methionine, and 5-bromo-4-chloro-3-indolyl-beta-D-galactopyranoside (X-gal; 50 mg/l). Colonies that did not turn blue were tested f6r kanamycin sensitivity and were then subjected to genotypic analysis.

Eight-week-old BALB/c mice were injected with either H37RvΔCysH or Mtb H37Rv (wild-type *M. tuberculosis*) (12 mice per strain). The bacteria were injected into the tail vein. Within 21 weeks, all of the mice infected with Mtb H37Rv succumbed to the infection. In contrast, all mice infected with Mtb H37RvΔCysH survived for at least 29 weeks following infection. The data are shown in FIG. 25. The appearance and behavior of the surviving H37RvΔCysH-infected mice were similar to those of uninfected mice. The sizes of the injections in colony forming units (CFU) were as follows: Mtb H37Rv: 1.21×10$^6$; Mtb H37RvΔCysH: 1.3×10$^6$. These results indicate that in vivo survival and growth of *M. tuberculosis* depends on intact sulfate assimilation.

A comparison of lungs of Mtb H37Rv-infected and H37RvΔCysH-infected mice at 13 weeks following infection was made. The Mtb H37Rv-infected mice showed extensive granuloma formation. H37RvΔCysH-infected mice showed few, if any, granulomas.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

SEQUENCE LISTING

<160> NUMBER OF SEQ ID NOS: 60

<210> SEQ ID NO 1
<211> LENGTH: 1185
<212> TYPE: DNA
<213> ORGANISM: Mycobacterium avium
<220> FEATURE:
<221> NAME/KEY: CDS
<222> LOCATION: (1)...(1185)

<400> SEQUENCE: 1

```
atg agc gac ttc gac aac atc acc acc gcc gac gac gtc ttc aag ctg      48
Met Ser Asp Phe Asp Asn Ile Thr Thr Ala Asp Asp Val Phe Lys Leu
 1               5                  10                  15 gcc gcg cag cgc acc ggc ctc agc gaa atc gac tcc gac tct tgg cga      96
Ala Ala Gln Arg Thr Gly Leu Ser Glu Ile Asp Ser Asp Ser Trp Arg
            20                  25                  30 gag ggc ctg gcg ctg atc gtc gac gag gtc aac acc tcg ccg gtc ttc     144
Glu Gly Leu Ala Leu Ile Val Asp Glu Val Asn Thr Ser Pro Val Phe
        35                  40                  45 acg ccg ttc ggg cgc cag cga gtc ctc gac gac gcc acc aac gcg ctg     192
Thr Pro Phe Gly Arg Gln Arg Val Leu Asp Asp Ala Thr Asn Ala Leu
    50                  55                  60 ggc cgg cgc cta cag gtg cac gcc tac atc cag gac cac ccc gag gtg     240
Gly Arg Arg Leu Gln Val His Ala Tyr Ile Gln Asp His Pro Glu Val
65                  70                  75                  80
```

```
                                                                    -continued ctc gac gcg ccg gtc gag cgg ccg ctc atc gtg ctc ggc atg ccg cgc      288
Leu Asp Ala Pro Val Glu Arg Pro Leu Ile Val Leu Gly Met Pro Arg
                 85                  90                  95 acc ggc acc acg gtc atc agt tac ctg ctc gac cag gac ccg gcc cgg      336
Thr Gly Thr Thr Val Ile Ser Tyr Leu Leu Asp Gln Asp Pro Ala Arg
            100                 105                 110 cgg tcg ctg ctg cac tgg cag tgc gtg cat ccg atc ccg ccg gcg agc      384
Arg Ser Leu Leu His Trp Gln Cys Val His Pro Ile Pro Pro Ala Ser
        115                 120                 125 acc gag acg ctg cgc acc gac ccg cgc tgc ctg gcc ctg ctg gac gag      432
Thr Glu Thr Leu Arg Thr Asp Pro Arg Cys Leu Ala Leu Leu Asp Glu
    130                 135                 140 cag cgc aag atc ctg gac gcc gtg aca cgg gcg aaa atg ccg ctg ccg      480
Gln Arg Lys Ile Leu Asp Ala Val Thr Arg Ala Lys Met Pro Leu Pro
145                 150                 155                 160 cac tgg gaa gac gcc gac ggc ccg acc gag gac atg ttc atc cac aac      528
His Trp Glu Asp Ala Asp Gly Pro Thr Glu Asp Met Phe Ile His Asn
                165                 170                 175 cag gac ttc aag ggc ctg tcc tgg gat tcc ttc ctg ccc aca gac cgc      576
Gln Asp Phe Lys Gly Leu Ser Trp Asp Ser Phe Leu Pro Thr Asp Arg
            180                 185                 190 tac gcg cgg tgg ctg ttc gac gaa gcc gac atg agc agc acg tac gag      624
Tyr Ala Arg Trp Leu Phe Asp Glu Ala Asp Met Ser Ser Thr Tyr Glu
        195                 200                 205 tac cag aag cga tac ctg cag gtg ctg cag tcc acc gcc ccg ggc agc      672
Tyr Gln Lys Arg Tyr Leu Gln Val Leu Gln Ser Thr Ala Pro Gly Ser
    210                 215                 220 tgg agc ctg aag atg ccg tcg cat tcg gtg cac atc gag gcg ctg ctc      720
Trp Ser Leu Lys Met Pro Ser His Ser Val His Ile Glu Ala Leu Leu
225                 230                 235                 240 aag gtg ttc ccg gac gcc cgg ctg atc tgg gcc cac cgc gac ccg tac      768
Lys Val Phe Pro Asp Ala Arg Leu Ile Trp Ala His Arg Asp Pro Tyr
                245                 250                 255 aag gcg acc ggt tcg ctg tgc aac ctg tgg cgg ctg ccg cag agc ctg      816
Lys Ala Thr Gly Ser Leu Cys Asn Leu Trp Arg Leu Pro Gln Ser Leu
            260                 265                 270 gtg atg aac acc gag ctt ctc gat cag acg gag atg ggc cgg ctg gcg      864
Val Met Asn Thr Glu Leu Leu Asp Gln Thr Glu Met Gly Arg Leu Ala
        275                 280                 285 atg tgg cag atg cgc tac cac gtc gac cgg ccg ctg cgg gcc cgc gag      912
Met Trp Gln Met Arg Tyr His Val Asp Arg Pro Leu Arg Ala Arg Glu
    290                 295                 300 cgc atc ggc gac gag cgc ttc ttc cac atg tac tac cac gag atg atg      960
Arg Ile Gly Asp Glu Arg Phe Phe His Met Tyr Tyr His Glu Met Met
305                 310                 315                 320 cgc gac ccg atg gac gtc atg cgg cgc atc tac gag tgg gcc gac gag     1008
Arg Asp Pro Met Asp Val Met Arg Arg Ile Tyr Glu Trp Ala Asp Glu
                325                 330                 335 ccg ttg acc gcc gaa acc gaa gcg cgc atg cgc aat tgg ctc gct cac     1056
Pro Leu Thr Ala Glu Thr Glu Ala Arg Met Arg Asn Trp Leu Ala His
            340                 345                 350 cac ccg cag gac cgg ttc gcg ctc aac gcc tat cgc ctc gac gaa tac     1104
His Pro Gln Asp Arg Phe Ala Leu Asn Ala Tyr Arg Leu Asp Glu Tyr
        355                 360                 365 ggc ctg acc gtc gaa gcg ctc cag ccg atc ttc gcc gaa tac ctc gac     1152
Gly Leu Thr Val Glu Ala Leu Gln Pro Ile Phe Ala Glu Tyr Leu Asp
    370                 375                 380 acc ttc gac att gaa ctg gaa ggc agg ccg tga                         1185
Thr Phe Asp Ile Glu Leu Glu Gly Arg Pro *
```

-continued

```
385            390

<210> SEQ ID NO 2
<211> LENGTH: 394
<212> TYPE: PRT
<213> ORGANISM: Mycobacterium avium

<400> SEQUENCE: 2

Met Ser Asp Phe Asp Asn Ile Thr Thr Ala Asp Asp Val Phe Lys Leu
 1               5                  10                  15

Ala Ala Gln Arg Thr Gly Leu Ser Glu Ile Asp Ser Asp Ser Trp Arg
            20                  25                  30

Glu Gly Leu Ala Leu Ile Val Asp Glu Val Asn Thr Ser Pro Val Phe
        35                  40                  45

Thr Pro Phe Gly Arg Gln Arg Val Leu Asp Asp Ala Thr Asn Ala Leu
    50                  55                  60

Gly Arg Arg Leu Gln Val His Ala Tyr Ile Gln Asp His Pro Glu Val
65                  70                  75                  80

Leu Asp Ala Pro Val Glu Arg Pro Leu Ile Val Leu Gly Met Pro Arg
                85                  90                  95

Thr Gly Thr Thr Val Ile Ser Tyr Leu Leu Asp Gln Asp Pro Ala Arg
            100                 105                 110

Arg Ser Leu Leu His Trp Gln Cys Val His Pro Ile Pro Pro Ala Ser
        115                 120                 125

Thr Glu Thr Leu Arg Thr Asp Pro Arg Cys Leu Ala Leu Leu Asp Glu
    130                 135                 140

Gln Arg Lys Ile Leu Asp Ala Val Thr Arg Ala Lys Met Pro Leu Pro
145                 150                 155                 160

His Trp Glu Asp Ala Asp Gly Pro Thr Glu Asp Met Phe Ile His Asn
                165                 170                 175

Gln Asp Phe Lys Gly Leu Ser Trp Asp Ser Phe Leu Pro Thr Asp Arg
            180                 185                 190

Tyr Ala Arg Trp Leu Phe Asp Glu Ala Asp Met Ser Ser Thr Tyr Glu
        195                 200                 205

Tyr Gln Lys Arg Tyr Leu Gln Val Leu Gln Ser Thr Ala Pro Gly Ser
    210                 215                 220

Trp Ser Leu Lys Met Pro Ser His Ser Val His Ile Glu Ala Leu Leu
225                 230                 235                 240

Lys Val Phe Pro Asp Ala Arg Leu Ile Trp Ala His Arg Asp Pro Tyr
                245                 250                 255

Lys Ala Thr Gly Ser Leu Cys Asn Leu Trp Arg Leu Pro Gln Ser Leu
            260                 265                 270

Val Met Asn Thr Glu Leu Leu Asp Gln Thr Glu Met Gly Arg Leu Ala
        275                 280                 285

Met Trp Gln Met Arg Tyr His Val Asp Arg Pro Leu Arg Ala Arg Glu
    290                 295                 300

Arg Ile Gly Asp Glu Arg Phe Phe His Met Tyr Tyr His Glu Met Met
305                 310                 315                 320

Arg Asp Pro Met Asp Val Met Arg Ile Tyr Glu Trp Ala Asp Glu
                325                 330                 335

Pro Leu Thr Ala Glu Thr Glu Ala Arg Met Arg Asn Trp Leu Ala His
            340                 345                 350

His Pro Gln Asp Arg Phe Ala Leu Asn Ala Tyr Arg Leu Asp Glu Tyr
        355                 360                 365
```

```
Gly Leu Thr Val Glu Ala Leu Gln Pro Ile Phe Ala Glu Tyr Leu Asp
    370                 375                 380

Thr Phe Asp Ile Glu Leu Glu Gly Arg Pro
385                 390
```

<210> SEQ ID NO 3
<211> LENGTH: 1146
<212> TYPE: DNA
<213> ORGANISM: Mycobacterium avium
<220> FEATURE:
<221> NAME/KEY: CDS
<222> LOCATION: (1)...(1146)

<400> SEQUENCE: 3

```
atg acg ttc gac gtc gac gag ttg gag cag ggc gct tgc gcg gcg acc      48
Met Thr Phe Asp Val Asp Glu Leu Glu Gln Gly Ala Cys Ala Ala Thr
 1               5                  10                  15 gat ctc gag gac ttc ggc tcg ccg tac tac cgc gag gga ctc gaa cgc      96
Asp Leu Glu Asp Phe Gly Ser Pro Tyr Tyr Arg Glu Gly Leu Glu Arg
             20                  25                  30 att gtt gac gcg ctg aac acc gag gcg gac ctg aac gac atg ggc cgg     144
Ile Val Asp Ala Leu Asn Thr Glu Ala Asp Leu Asn Asp Met Gly Arg
         35                  40                  45 gtc atc cag cac gcc act atc agc aac gcg cta atc caa cgt ctc aag     192
Val Ile Gln His Ala Thr Ile Ser Asn Ala Leu Ile Gln Arg Leu Lys
     50                  55                  60 gtc gag cag acc tac gct gcg cac cca gag atc gac gag cag gtg gtg     240
Val Glu Gln Thr Tyr Ala Ala His Pro Glu Ile Asp Glu Gln Val Val
 65                  70                  75                  80 ggc ggc ccc gtg ttc gtg atc gga tta ccc cgc acc ggg acc acc gcc     288
Gly Gly Pro Val Phe Val Ile Gly Leu Pro Arg Thr Gly Thr Thr Ala
                 85                  90                  95 ctg agc caa ctc gtc ggc gcc gat ccg cag ttc cgg tcg ctg cgg atg     336
Leu Ser Gln Leu Val Gly Ala Asp Pro Gln Phe Arg Ser Leu Arg Met
            100                 105                 110 tgg gaa tcc caa tca ccc acc ccg cca ccg gaa gcc gcc acc cag cac     384
Trp Glu Ser Gln Ser Pro Thr Pro Pro Pro Glu Ala Ala Thr Gln His
        115                 120                 125 agc gac cca cgg atc gca cag gcc gcc gcc ggc ctg aaa atg ctc gac     432
Ser Asp Pro Arg Ile Ala Gln Ala Ala Ala Gly Leu Lys Met Leu Asp
    130                 135                 140 gag atg ttc ccg ctg atg aaa acg ctg tac aac tcc gag ccc acg gca     480
Glu Met Phe Pro Leu Met Lys Thr Leu Tyr Asn Ser Glu Pro Thr Ala
145                 150                 155                 160 cct acc gaa tgc cag gac ttg atg gga atg agc ttt cgt acc ttt cac     528
Pro Thr Glu Cys Gln Asp Leu Met Gly Met Ser Phe Arg Thr Phe His
                165                 170                 175 ttt gac ggt gcc gtg cgc gca ccg gga tat ctg tcc tgg ctg atg ggc     576
Phe Asp Gly Ala Val Arg Ala Pro Gly Tyr Leu Ser Trp Leu Met Gly
            180                 185                 190 tgc gac atg cgg ggc acc tat ctg tat cac cgg cgg gtg ctc aaa ctc     624
Cys Asp Met Arg Gly Thr Tyr Leu Tyr His Arg Arg Val Leu Lys Leu
        195                 200                 205 ctg caa tgg cac tgc cca ccg gtg ctg tgg cac ctc aag act ccg gtg     672
Leu Gln Trp His Cys Pro Pro Val Leu Trp His Leu Lys Thr Pro Val
    210                 215                 220 cac atg ttc gcc ctc gac gcc ctc gtc gag gcc tac ccg gac gcc aag     720
His Met Phe Ala Leu Asp Ala Leu Val Glu Ala Tyr Pro Asp Ala Lys
225                 230                 235                 240 ttc ctg tgg agt cac cgc gac ccc gcc aag gtg atg gcc tcg gta tgc     768
Phe Leu Trp Ser His Arg Asp Pro Ala Lys Val Met Ala Ser Val Cys
```

-continued

```
                245                 250                 255
agc ctc att caa tac gta cgc agc tgg agt agc gac cgc aac gac cct      816
Ser Leu Ile Gln Tyr Val Arg Ser Trp Ser Ser Asp Arg Asn Asp Pro
            260                 265                 270 cac gag ctc ggc cgt gag cag gtc gac agc tgg gtc gaa gga gtc cgt      864
His Glu Leu Gly Arg Glu Gln Val Asp Ser Trp Val Glu Gly Val Arg
        275                 280                 285 cgc gca atg gat ttc cgt cgc cgc aac ggc gac gag cgc ttc gcc gac      912
Arg Ala Met Asp Phe Arg Arg Arg Asn Gly Asp Glu Arg Phe Ala Asp
    290                 295                 300 gtg tcc ttc gcc gac ttg cag acc gac ccg gtc ggc acc ctg cgc gcc      960
Val Ser Phe Ala Asp Leu Gln Thr Asp Pro Val Gly Thr Leu Arg Ala
305                 310                 315                 320 agc tac cag tcc ctg ggc ctg gac ttc acc gat gac act ttg cac gcg     1008
Ser Tyr Gln Ser Leu Gly Leu Asp Phe Thr Asp Asp Thr Leu His Ala
            325                 330                 335 gtc acg cag tgg gcg cgg acg cat cga ccc ggt tcc cgt ggc cac cat     1056
Val Thr Gln Trp Ala Arg Thr His Arg Pro Gly Ser Arg Gly His His
        340                 345                 350 gac tac gac ttg gcc gac tac ggc ctg acg ccc gaa ggt gtt cgg gaa     1104
Asp Tyr Asp Leu Ala Asp Tyr Gly Leu Thr Pro Glu Gly Val Arg Glu
    355                 360                 365 cgg ttc gcg gac tac ctc gcc gtc tac gac gcg acg gca tga             1146
Arg Phe Ala Asp Tyr Leu Ala Val Tyr Asp Ala Thr Ala *
370                 375                 380

<210> SEQ ID NO 4
<211> LENGTH: 381
<212> TYPE: PRT
<213> ORGANISM: Mycobacterium avium

<400> SEQUENCE: 4

Met Thr Phe Asp Val Asp Glu Leu Glu Gln Gly Ala Cys Ala Ala Thr
1               5                   10                  15

Asp Leu Glu Asp Phe Gly Ser Pro Tyr Tyr Arg Glu Gly Leu Glu Arg
            20                  25                  30

Ile Val Asp Ala Leu Asn Thr Glu Ala Asp Leu Asn Asp Met Gly Arg
        35                  40                  45

Val Ile Gln His Ala Thr Ile Ser Asn Ala Leu Ile Gln Arg Leu Lys
    50                  55                  60

Val Glu Gln Thr Tyr Ala Ala His Pro Glu Ile Asp Glu Gln Val Val
65                  70                  75                  80

Gly Gly Pro Val Phe Val Ile Gly Leu Pro Arg Thr Gly Thr Thr Ala
            85                  90                  95

Leu Ser Gln Leu Val Gly Ala Asp Pro Gln Phe Arg Ser Leu Arg Met
        100                 105                 110

Trp Glu Ser Gln Ser Pro Thr Pro Pro Glu Ala Ala Thr Gln His
    115                 120                 125

Ser Asp Pro Arg Ile Ala Gln Ala Ala Gly Leu Lys Met Leu Asp
130                 135                 140

Glu Met Phe Pro Leu Met Lys Thr Leu Tyr Asn Ser Glu Pro Thr Ala
145                 150                 155                 160

Pro Thr Glu Cys Gln Asp Leu Met Gly Met Ser Phe Arg Thr Phe His
            165                 170                 175

Phe Asp Gly Ala Val Arg Ala Pro Gly Tyr Leu Ser Trp Leu Met Gly
        180                 185                 190

Cys Asp Met Arg Gly Thr Tyr Leu Tyr His Arg Arg Val Leu Lys Leu
```

```
                195                 200                  205
Leu Gln Trp His Cys Pro Pro Val Leu Trp His Leu Lys Thr Pro Val
    210                 215                  220

His Met Phe Ala Leu Asp Ala Leu Val Glu Ala Tyr Pro Asp Ala Lys
225                 230                 235                 240

Phe Leu Trp Ser His Arg Asp Pro Ala Lys Val Met Ala Ser Val Cys
                245                 250                 255

Ser Leu Ile Gln Tyr Val Arg Ser Trp Ser Ser Asp Arg Asn Asp Pro
            260                 265                 270

His Glu Leu Gly Arg Glu Gln Val Asp Ser Trp Val Glu Gly Val Arg
        275                 280                 285

Arg Ala Met Asp Phe Arg Arg Asn Gly Asp Glu Arg Phe Ala Asp
    290                 295                 300

Val Ser Phe Ala Asp Leu Gln Thr Asp Pro Val Gly Thr Leu Arg Ala
305                 310                 315                 320

Ser Tyr Gln Ser Leu Gly Leu Asp Phe Thr Asp Thr Leu His Ala
                325                 330                 335

Val Thr Gln Trp Ala Arg Thr His Arg Pro Gly Ser Arg Gly His His
            340                 345                 350

Asp Tyr Asp Leu Ala Asp Tyr Gly Leu Thr Pro Glu Gly Val Arg Glu
        355                 360                 365

Arg Phe Ala Asp Tyr Leu Ala Val Tyr Asp Ala Thr Ala
    370                 375                 380

<210> SEQ ID NO 5
<211> LENGTH: 1170
<212> TYPE: DNA
<213> ORGANISM: Mycobacterium avium
<220> FEATURE:
<221> NAME/KEY: CDS
<222> LOCATION: (1)...(1170)

<400> SEQUENCE: 5 atg tcg ccg gcg gac agt gga tgg gct gat cca atg ccg gca gtc aac      48
Met Ser Pro Ala Asp Ser Gly Trp Ala Asp Pro Met Pro Ala Val Asn
 1               5                  10                  15 gat ctc ctg caa acc gcg gtt gcc cag acc ggt ctc gac gat ttc ggg      96
Asp Leu Leu Gln Thr Ala Val Ala Gln Thr Gly Leu Asp Asp Phe Gly
             20                  25                  30 gat gat tcc ttt cga gaa ggc ctc gag ata ctg ttg acg tcg ctg cgc     144
Asp Asp Ser Phe Arg Glu Gly Leu Glu Ile Leu Leu Thr Ser Leu Arg
         35                  40                  45 gat gag gcc cgg ctc aac gcc aaa ggt gag gcc ttc atc tat ccg cgg     192
Asp Glu Ala Arg Leu Asn Ala Lys Gly Glu Ala Phe Ile Tyr Pro Arg
     50                  55                  60 atc acc gca tac ctt gct cag cgg ctg cag gtc gag gat tgg tac cgc     240
Ile Thr Ala Tyr Leu Ala Gln Arg Leu Gln Val Glu Asp Trp Tyr Arg
 65                  70                  75                  80 cgg cat ccc gag atc gac gag gtg tcc ctc gag tct ccg ctg atc ggg     288
Arg His Pro Glu Ile Asp Glu Val Ser Leu Glu Ser Pro Leu Ile Gly
                 85                  90                  95 ctc ggc ttg ccg cgc aca ggg tcg acg gca ttg tcg atg ctg ctc gct     336
Leu Gly Leu Pro Arg Thr Gly Ser Thr Ala Leu Ser Met Leu Leu Ala
            100                 105                 110 cag gac ccc gat gtc cgg tat ctg cgc aaa tgg gag tcc tcc caa ccg     384
Gln Asp Pro Asp Val Arg Tyr Leu Arg Lys Trp Glu Ser Ser Gln Pro
        115                 120                 125 tgt ccg ccg ccg tcg acc gtg tgc ggt gtg gat ccg cgc atc ccg ccc     432
```

```
                                                          -continued

Cys Pro Pro Ser Thr Val Cys Gly Val Asp Pro Arg Ile Pro Pro
        130                 135                 140 ggc aag ggg gaa atg atc ggc act cgc cac cat gtg ccc acg gac gcc        480
Gly Lys Gly Glu Met Ile Gly Thr Arg His His Val Pro Thr Asp Ala
145                 150                 155                 160 aac ggg ccg atg gaa tgt cac gag ctg atg gct ctg agt ttc gcc tcc        528
Asn Gly Pro Met Glu Cys His Glu Leu Met Ala Leu Ser Phe Ala Ser
                    165                 170                 175 cac ctg ttc cag tcg ctg gcc caa gtt ccc acc tat tcg gcg tgg ctg        576
His Leu Phe Gln Ser Leu Ala Gln Val Pro Thr Tyr Ser Ala Trp Leu
                180                 185                 190 gtg gcc gac gcc gac ctc acc tcg gcg ctc gcg tac gag cgt cgg gtg        624
Val Ala Asp Ala Asp Leu Thr Ser Ala Leu Ala Tyr Glu Arg Arg Val
            195                 200                 205 ctc aag ctg ctg gcc tgg ggt gag ccg acg cgg ccg tgg agg ctg aaa        672
Leu Lys Leu Leu Ala Trp Gly Glu Pro Thr Arg Pro Trp Arg Leu Lys
        210                 215                 220 tgc ccc tcg cac gtg ctc tgg ctt gac cgc ctg gcc gcg gtc ttc cca        720
Cys Pro Ser His Val Leu Trp Leu Asp Arg Leu Ala Ala Val Phe Pro
225                 230                 235                 240 gac gcc aaa ttc gtg atg acg cac cgt gat ccc acc gac gtc atc ctg        768
Asp Ala Lys Phe Val Met Thr His Arg Asp Pro Thr Asp Val Ile Leu
                    245                 250                 255 tca gtc gcc gac ctc tac gcc gac atc atc ggc cag ttc acc gac gac        816
Ser Val Ala Asp Leu Tyr Ala Asp Ile Ile Gly Gln Phe Thr Asp Asp
                260                 265                 270 atc gac cgc ccc tat atc ggg cgg ctc aac gtc gag cat tgg tcg ttg        864
Ile Asp Arg Pro Tyr Ile Gly Arg Leu Asn Val Glu His Trp Ser Leu
            275                 280                 285 ggc atg gcc cgc acg ctg cag ttc cgg gca gcg ggc aac gat aac cgg        912
Gly Met Ala Arg Thr Leu Gln Phe Arg Ala Ala Gly Asn Asp Asn Arg
        290                 295                 300 ttc tat gac atc gac ttt cgc gcg atg cag gcc gac ccg atc ggc gag        960
Phe Tyr Asp Ile Asp Phe Arg Ala Met Gln Ala Asp Pro Ile Gly Glu
305                 310                 315                 320 gtg acg gga tta tat cgc tgg ctt ggc gaa cag gtc agc gac gaa ttc       1008
Val Thr Gly Leu Tyr Arg Trp Leu Gly Glu Gln Val Ser Asp Glu Phe
                    325                 330                 335 gag ggc cga atg aac agc tgg tgg gcg cag gcg gca acc gag cgc gaa       1056
Glu Gly Arg Met Asn Ser Trp Trp Ala Gln Ala Ala Thr Glu Arg Glu
                340                 345                 350 ccc agc agc cat gct gac cct gtt cag ttc ggg atc gac ctg gat tcg       1104
Pro Ser Ser His Ala Asp Pro Val Gln Phe Gly Ile Asp Leu Asp Ser
            355                 360                 365 ata cgg ccg ctg ttc gcc gac tac atc acg gcc gcc gcc gac tgg acc       1152
Ile Arg Pro Leu Phe Ala Asp Tyr Ile Thr Ala Ala Ala Asp Trp Thr
        370                 375                 380 gca cac gcc gac atc tag                                               1170
Ala His Ala Asp Ile *
385

<210> SEQ ID NO 6
<211> LENGTH: 389
<212> TYPE: PRT
<213> ORGANISM: Mycobacterium avium

<400> SEQUENCE: 6

Met Ser Pro Ala Asp Ser Gly Trp Ala Asp Pro Met Pro Ala Val Asn
1               5                   10                  15

Asp Leu Leu Gln Thr Ala Val Ala Gln Thr Gly Leu Asp Asp Phe Gly
```

```
                  20                  25                  30
Asp Asp Ser Phe Arg Glu Gly Leu Glu Ile Leu Leu Thr Ser Leu Arg
                35                  40                  45

Asp Glu Ala Arg Leu Asn Ala Lys Gly Glu Ala Phe Ile Tyr Pro Arg
                50                  55                  60

Ile Thr Ala Tyr Leu Ala Gln Arg Leu Gln Val Glu Asp Trp Tyr Arg
 65                 70                  75                  80

Arg His Pro Glu Ile Asp Glu Val Ser Leu Glu Ser Pro Leu Ile Gly
                    85                  90                  95

Leu Gly Leu Pro Arg Thr Gly Ser Thr Ala Leu Ser Met Leu Leu Ala
                100                 105                 110

Gln Asp Pro Asp Val Arg Tyr Leu Arg Lys Trp Glu Ser Ser Gln Pro
                115                 120                 125

Cys Pro Pro Ser Thr Val Cys Gly Val Asp Pro Arg Ile Pro Pro
                130                 135                 140

Gly Lys Gly Glu Met Ile Gly Thr Arg His His Val Pro Thr Asp Ala
145                 150                 155                 160

Asn Gly Pro Met Glu Cys His Glu Leu Met Ala Leu Ser Phe Ala Ser
                    165                 170                 175

His Leu Phe Gln Ser Leu Ala Gln Val Pro Thr Tyr Ser Ala Trp Leu
                180                 185                 190

Val Ala Asp Ala Asp Leu Thr Ser Ala Leu Ala Tyr Glu Arg Arg Val
                195                 200                 205

Leu Lys Leu Leu Ala Trp Gly Glu Pro Thr Arg Pro Trp Arg Leu Lys
210                 215                 220

Cys Pro Ser His Val Leu Trp Leu Asp Arg Leu Ala Ala Val Phe Pro
225                 230                 235                 240

Asp Ala Lys Phe Val Met Thr His Arg Asp Pro Thr Asp Val Ile Leu
                245                 250                 255

Ser Val Ala Asp Leu Tyr Ala Asp Ile Ile Gly Gln Phe Thr Asp Asp
                260                 265                 270

Ile Asp Arg Pro Tyr Ile Gly Arg Leu Asn Val Glu His Trp Ser Leu
                275                 280                 285

Gly Met Ala Arg Thr Leu Gln Phe Arg Ala Ala Gly Asn Asp Asn Arg
290                 295                 300

Phe Tyr Asp Ile Asp Phe Arg Ala Met Gln Ala Asp Pro Ile Gly Glu
305                 310                 315                 320

Val Thr Gly Leu Tyr Arg Trp Leu Gly Glu Gln Val Ser Asp Glu Phe
                325                 330                 335

Glu Gly Arg Met Asn Ser Trp Trp Ala Gln Ala Thr Glu Arg Glu
                340                 345                 350

Pro Ser Ser His Ala Asp Pro Val Gln Phe Gly Ile Asp Leu Asp Ser
                355                 360                 365

Ile Arg Pro Leu Phe Ala Asp Tyr Ile Thr Ala Ala Ala Asp Trp Thr
370                 375                 380

Ala His Ala Asp Ile
385

<210> SEQ ID NO 7
<211> LENGTH: 1164
<212> TYPE: DNA
<213> ORGANISM: Mycobacterium avium
<220> FEATURE:
<221> NAME/KEY: CDS
<222> LOC

<400> SEQUENCE: 7

```
atg atg gcc gcg atg gcc ccg cag tgc ccg ctg gat gcc gac gcg ctg      48
Met Met Ala Ala Met Ala Pro Gln Cys Pro Leu Asp Ala Asp Ala Leu
 1               5                  10                  15 cac gcc cag gcc agc gcc gac acc ggc ctg cac gac ttc ggg ccc gac      96
His Ala Gln Ala Ser Ala Asp Thr Gly Leu His Asp Phe Gly Pro Asp
                20                  25                  30 gac tac cgg gag cgc ctc gag gtc tac ctg acc gcg ctg cgc gaa atc     144
Asp Tyr Arg Glu Arg Leu Glu Val Tyr Leu Thr Ala Leu Arg Glu Ile
         35                  40                  45 gac ggg ctg cac gcc gcc ggg acg gtc aac ttc tac ggt cag ctg ctg     192
Asp Gly Leu His Ala Ala Gly Thr Val Asn Phe Tyr Gly Gln Leu Leu
     50                  55                  60 cag atc ctc aag aac cgg ctg ctg ctg acc gac ctg ctc aag cgc cat     240
Gln Ile Leu Lys Asn Arg Leu Leu Leu Thr Asp Leu Leu Lys Arg His
 65                  70                  75                  80 ccc gag atc cac gac atc gaa ctg cgc tcc ccg gtg gtg atc gcc ggg     288
Pro Glu Ile His Asp Ile Glu Leu Arg Ser Pro Val Val Ile Ala Gly
                 85                  90                  95 ctg ccc cgc acc ggc acc acc cac ctg cac aac ctg ctg gcc gcg cca     336
Leu Pro Arg Thr Gly Thr Thr His Leu His Asn Leu Leu Ala Ala Pro
                100                 105                 110 ccc acc ttc cgc acc atg ccc tac tgg gaa agc gtg gag ccg ttt ccg     384
Pro Thr Phe Arg Thr Met Pro Tyr Trp Glu Ser Val Glu Pro Phe Pro
            115                 120                 125 atg ccc aat gag gtt ggc gtg caa ccg gat ccg cgg cga acc cgg atg     432
Met Pro Asn Glu Val Gly Val Gln Pro Asp Pro Arg Arg Thr Arg Met
        130                 135                 140 gac gtc gcg gtc gcg gtg atc aac acg gtg atg ccg cat ttc gcg ctg     480
Asp Val Ala Val Ala Val Ile Asn Thr Val Met Pro His Phe Ala Leu
145                 150                 155                 160 atg cac gag atg acc acc gat cac gtc cac gag gag atc cag ttg ctg     528
Met His Glu Met Thr Thr Asp His Val His Glu Glu Ile Gln Leu Leu
                165                 170                 175 gcc aac gac gtg tcc acc atg ctg ctg gag acg ctc gcc gag gtg ccg     576
Ala Asn Asp Val Ser Thr Met Leu Leu Glu Thr Leu Ala Glu Val Pro
            180                 185                 190 cgc tgg cgc gcc tac tac cag gcc cac gat cag acg ccg cac tac gaa     624
Arg Trp Arg Ala Tyr Tyr Gln Ala His Asp Gln Thr Pro His Tyr Glu
        195                 200                 205 tat ctg gcc acc cag ctg cgg gcg atg cag ttc ctg cgc ggc ggc cgg     672
Tyr Leu Ala Thr Gln Leu Arg Ala Met Gln Phe Leu Arg Gly Gly Arg
    210                 215                 220 cgc tgg ctg ctc aag tcg cct cag cat ctc gag cag gtg ccg gtg ctg     720
Arg Trp Leu Leu Lys Ser Pro Gln His Leu Glu Gln Val Pro Val Leu
225                 230                 235                 240 gat cgg gtg ttc ccg gac agc atc gtc gtg ttc acc cac cgc gac ccg     768
Asp Arg Val Phe Pro Asp Ser Ile Val Val Phe Thr His Arg Asp Pro
                245                 250                 255 gtg ccg gtg gcg ctg tcg atg atc gcg atg atc acc tac tcg gcc cgc     816
Val Pro Val Ala Leu Ser Met Ile Ala Met Ile Thr Tyr Ser Ala Arg
            260                 265                 270 atg cac cgc tcg ccg gtg ccg gtg cgc cag atc gcc gag tcc tgg atc     864
Met His Arg Ser Pro Val Pro Val Arg Gln Ile Ala Glu Ser Trp Ile
        275                 280                 285 gac cgc ctg ggg cag atg ctg gcc gcg ctg gtc cgc gac cgc gac gtc     912
Asp Arg Leu Gly Gln Met Leu Ala Ala Leu Val Arg Asp Arg Asp Val
    290                 295                 300
```

```
atc ggc ccg gac cgt tcg atc gac atc cgc ttc gac gac ttc atg gcc    960
Ile Gly Pro Asp Arg Ser Ile Asp Ile Arg Phe Asp Asp Phe Met Ala
305                 310                 315                 320 gac gaa ctc ggc gtg gcc gag cgg gtc tac gcc ctg gcg gac gag ccg   1008
Asp Glu Leu Gly Val Ala Glu Arg Val Tyr Ala Leu Ala Asp Glu Pro
                325                 330                 335 ttc acc gac gac gcg cgc gcc gcc gtc gcc gac tac ctg gcg ggt cac   1056
Phe Thr Asp Asp Ala Arg Ala Ala Val Ala Asp Tyr Leu Ala Gly His
            340                 345                 350 cgc cgc ggc cgg ctg ggc aac gtc gaa acg tcc tac gag atg ttc ggg   1104
Arg Arg Gly Arg Leu Gly Asn Val Glu Thr Ser Tyr Glu Met Phe Gly
355                 360                 365 ttg gac gag gac agc ctg cgc gag cgt ttc gcc ccc tac gtc gag cgg   1152
Leu Asp Glu Asp Ser Leu Arg Glu Arg Phe Ala Pro Tyr Val Glu Arg
370                 375                 380 ttc ctg gcc taa                                                   1164
Phe Leu Ala *
385

<210> SEQ ID NO 8
<211> LENGTH: 387
<212> TYPE: PRT
<213> ORGANISM: Mycobacterium avium

<400> SEQUENCE: 8

Met Met Ala Ala Met Ala Pro Gln Cys Pro Leu Asp Ala Asp Ala Leu
1               5                   10                  15

His Ala Gln Ala Ser Ala Asp Thr Gly Leu His Asp Phe Gly Pro Asp
            20                  25                  30

Asp Tyr Arg Glu Arg Leu Glu Val Tyr Leu Thr Ala Leu Arg Glu Ile
        35                  40                  45

Asp Gly Leu His Ala Ala Gly Thr Val Asn Phe Tyr Gly Gln Leu Leu
    50                  55                  60

Gln Ile Leu Lys Asn Arg Leu Leu Leu Thr Asp Leu Leu Lys Arg His
65                  70                  75                  80

Pro Glu Ile His Asp Ile Glu Leu Arg Ser Pro Val Val Ile Ala Gly
                85                  90                  95

Leu Pro Arg Thr Gly Thr Thr His Leu His Asn Leu Leu Ala Ala Pro
            100                 105                 110

Pro Thr Phe Arg Thr Met Pro Tyr Trp Glu Ser Val Glu Pro Phe Pro
        115                 120                 125

Met Pro Asn Glu Val Gly Val Gln Pro Asp Pro Arg Arg Thr Arg Met
    130                 135                 140

Asp Val Ala Val Ala Val Ile Asn Thr Val Met Pro His Phe Ala Leu
145                 150                 155                 160

Met His Glu Met Thr Thr Asp His Val His Glu Ile Gln Leu Leu
                165                 170                 175

Ala Asn Asp Val Ser Thr Met Leu Leu Glu Thr Leu Ala Glu Val Pro
            180                 185                 190

Arg Trp Arg Ala Tyr Tyr Gln Ala His Asp Gln Thr Pro His Tyr Glu
        195                 200                 205

Tyr Leu Ala Thr Gln Leu Arg Ala Met Gln Phe Leu Arg Gly Gly Arg
    210                 215                 220

Arg Trp Leu Leu Lys Ser Pro Gln His Leu Glu Gln Val Pro Val Leu
225                 230                 235                 240

Asp Arg Val Phe Pro Asp Ser Ile Val Val Phe Thr His Arg Asp Pro
                245                 250                 255
```

-continued

```
Val Pro Val Ala Leu Ser Met Ile Ala Met Ile Thr Tyr Ser Ala Arg
            260                 265                 270

Met His Arg Ser Pro Val Pro Val Arg Gln Ile Ala Glu Ser Trp Ile
        275                 280                 285

Asp Arg Leu Gly Gln Met Leu Ala Ala Leu Val Arg Asp Arg Asp Val
    290                 295                 300

Ile Gly Pro Asp Arg Ser Ile Asp Ile Arg Phe Asp Asp Phe Met Ala
305                 310                 315                 320

Asp Glu Leu Gly Val Ala Glu Arg Val Tyr Ala Leu Ala Asp Glu Pro
                325                 330                 335

Phe Thr Asp Asp Ala Arg Ala Ala Val Ala Asp Tyr Leu Ala Gly His
            340                 345                 350

Arg Arg Gly Arg Leu Gly Asn Val Glu Thr Ser Tyr Glu Met Phe Gly
        355                 360                 365

Leu Asp Glu Asp Ser Leu Arg Glu Arg Phe Ala Pro Tyr Val Glu Arg
    370                 375                 380

Phe Leu Ala
385

<210> SEQ ID NO 9
<211> LENGTH: 1146
<212> TYPE: DNA
<213> ORGANISM: Mycobacterium avium
<220> FEATURE:
<221> NAME/KEY: CDS
<222> LOCATION: (1)...(1146)

<400> SEQUENCE: 9 atg ctc gcc gag gcg atc gaa cag gcc ggc ctg ccc ggc gcc gac ctc      48
Met Leu Ala Glu Ala Ile Glu Gln Ala Gly Leu Pro Gly Ala Asp Leu
  1               5                  10                  15 gac gac acg cac ggc ttc gtc gac cgt ctg cac gtc cac gtc gcg gcg      96
Asp Asp Thr His Gly Phe Val Asp Arg Leu His Val His Val Ala Ala
                 20                  25                  30 atc gaa gcc gac cac ggg ctg cgc cag ctc acc cgg ggg tcg ctg cgg     144
Ile Glu Ala Asp His Gly Leu Arg Gln Leu Thr Arg Gly Ser Leu Arg
             35                  40                  45 caa cgc gtg gtg cgg ctg ctg cgc aac cgg ttg tcg ctg acc gag ctg     192
Gln Arg Val Val Arg Leu Leu Arg Asn Arg Leu Ser Leu Thr Glu Leu
         50                  55                  60 ctc cag cgg tat ccc gag atc gag tcc atc ccg atc gag cag ccg ttc     240
Leu Gln Arg Tyr Pro Glu Ile Glu Ser Ile Pro Ile Glu Gln Pro Phe
 65                  70                  75                  80 atc gtc gtc ggg atg ccg cgt tcg ggc acc acg cat ctt gtg aac ctg     288
Ile Val Val Gly Met Pro Arg Ser Gly Thr Thr His Leu Val Asn Leu
                 85                  90                  95 atc gcc tgc gac ccg cgc cgg cgt gca ctg ccc tat tgg gag agc cag     336
Ile Ala Cys Asp Pro Arg Arg Arg Ala Leu Pro Tyr Trp Glu Ser Gln
                100                 105                 110 gag cct atc ccg gcc cgt ggt cag ggc ccc gac gtc ttc ggt gtc gac     384
Glu Pro Ile Pro Ala Arg Gly Gln Gly Pro Asp Val Phe Gly Val Asp
            115                 120                 125 ccc cgg tat gcc cgc gcc aag gcg gaa cac gag gcg ctg atg gcc agc     432
Pro Arg Tyr Ala Arg Ala Lys Ala Glu His Glu Ala Leu Met Ala Ser
        130                 135                 140 gcg ccc gtg gtg gcc gcc atg cac gac cgg ttt ccc gag gcg atc gag     480
Ala Pro Val Val Ala Ala Met His Asp Arg Phe Pro Glu Ala Ile Glu
145                 150                 155                 160
```

```
gag gaa gtg gaa ctg ctc gac ctc gat ctg gcc tcc tac gtc ctg gaa      528
Glu Glu Val Glu Leu Leu Asp Leu Asp Leu Ala Ser Tyr Val Leu Glu
            165                 170                 175 tgg cat gcg cgg gtg ccc gcc tgg cgc gat cac tac ctg agc ctg gac      576
Trp His Ala Arg Val Pro Ala Trp Arg Asp His Tyr Leu Ser Leu Asp
        180                 185                 190 caa acc cgg cac tac gcc tac ctg aag aag gtg ttg cag gcg ttg acc      624
Gln Thr Arg His Tyr Ala Tyr Leu Lys Lys Val Leu Gln Ala Leu Thr
    195                 200                 205 ttc ctg cgc ggg ccg cgg acc tgg gtg ctc aaa agt ccg cag cac tgc      672
Phe Leu Arg Gly Pro Arg Thr Trp Val Leu Lys Ser Pro Gln His Cys
210                 215                 220 gag cag ctc ggc ccg ctg atg gcg acc ttc ccc gat gcg acg atc gcg      720
Glu Gln Leu Gly Pro Leu Met Ala Thr Phe Pro Asp Ala Thr Ile Ala
225                 230                 235                 240 ttc acg cac cgc gac ccc gtc gca gtg atc cag tcg gcg atc acc atg      768
Phe Thr His Arg Asp Pro Val Ala Val Ile Gln Ser Ala Ile Thr Met
                245                 250                 255 atg gcc tac tcg gat cgg ttg cgc cgc acc agc att gac ccg cag tgg      816
Met Ala Tyr Ser Asp Arg Leu Arg Arg Thr Ser Ile Asp Pro Gln Trp
            260                 265                 270 ctg ctg gac tac tgg agc gac cgg gtg cac cga ctg ctg agc gcc tgc      864
Leu Leu Asp Tyr Trp Ser Asp Arg Val His Arg Leu Leu Ser Ala Cys
        275                 280                 285 gtc cgc gac cgc gac ctg gtg gcc ccg gaa cgc agc gtc gac atc agc      912
Val Arg Asp Arg Asp Leu Val Ala Pro Glu Arg Ser Val Asp Ile Ser
    290                 295                 300 ttc cat cag ttg agc ggc aac gag atc ccg gtg atc gaa cgg ctg tat      960
Phe His Gln Leu Ser Gly Asn Glu Ile Pro Val Ile Glu Arg Leu Tyr
305                 310                 315                 320 gag cgc ggc ggg gtg gaa ttg ccg cag cgg gtg cgc gac cgc ttt cag     1008
Glu Arg Gly Gly Val Glu Leu Pro Gln Arg Val Arg Asp Arg Phe Gln
                325                 330                 335 cgc tac ctg gac gga aat ccg cgc ggt aag cac ggc cgc atc cgc tac     1056
Arg Tyr Leu Asp Gly Asn Pro Arg Gly Lys His Gly Arg Ile Arg Tyr
            340                 345                 350 cag ttg cag cgc cat ttc ggc atc tcc gcc gac gag ctg cgc gcc cgt     1104
Gln Leu Gln Arg His Phe Gly Ile Ser Ala Asp Glu Leu Arg Ala Arg
        355                 360                 365 ttc ggc ttc tac ttc gac aag ttc gac gtg cgc ccc gaa tga             1146
Phe Gly Phe Tyr Phe Asp Lys Phe Asp Val Arg Pro Glu *
    370                 375                 380

<210> SEQ ID NO 10
<211> LENGTH: 381
<212> TYPE: PRT
<213> ORGANISM: Mycobacterium avium

<400> SEQUENCE: 10

Met Leu Ala Glu Ala Ile Glu Gln Ala Gly Leu Pro Gly Ala Asp Leu
1               5                   10                  15

Asp Asp Thr His Gly Phe Val Asp Arg Leu His Val His Val Ala Ala
            20                  25                  30

Ile Glu Ala Asp His Gly Leu Arg Gln Leu Thr Arg Gly Ser Leu Arg
        35                  40                  45

Gln Arg Val Val Arg Leu Leu Arg Asn Arg Leu Ser Leu Thr Glu Leu
    50                  55                  60

Leu Gln Arg Tyr Pro Glu Ile Glu Ser Ile Pro Ile Glu Gln Pro Phe
65                  70                  75                  80
```

```
Ile Val Val Gly Met Pro Arg Ser Gly Thr Thr His Leu Val Asn Leu
                85                  90                  95

Ile Ala Cys Asp Pro Arg Arg Ala Leu Pro Tyr Trp Glu Ser Gln
            100                 105                 110

Glu Pro Ile Pro Ala Arg Gly Gln Gly Pro Asp Val Phe Gly Val Asp
            115                 120                 125

Pro Arg Tyr Ala Arg Ala Lys Ala Glu His Glu Ala Leu Met Ala Ser
            130                 135                 140

Ala Pro Val Val Ala Ala Met His Asp Arg Phe Pro Glu Ala Ile Glu
145                 150                 155                 160

Glu Glu Val Glu Leu Leu Asp Leu Asp Leu Ala Ser Tyr Val Leu Glu
                165                 170                 175

Trp His Ala Arg Val Pro Ala Trp Arg Asp His Tyr Leu Ser Leu Asp
            180                 185                 190

Gln Thr Arg His Tyr Ala Tyr Leu Lys Lys Val Leu Gln Ala Leu Thr
            195                 200                 205

Phe Leu Arg Gly Pro Arg Thr Trp Val Leu Lys Ser Pro Gln His Cys
210                 215                 220

Glu Gln Leu Gly Pro Leu Met Ala Thr Phe Pro Asp Ala Thr Ile Ala
225                 230                 235                 240

Phe Thr His Arg Asp Pro Val Ala Val Ile Gln Ser Ala Ile Thr Met
                245                 250                 255

Met Ala Tyr Ser Asp Arg Leu Arg Arg Thr Ser Ile Asp Pro Gln Trp
            260                 265                 270

Leu Leu Asp Tyr Trp Ser Asp Arg Val His Arg Leu Leu Ser Ala Cys
            275                 280                 285

Val Arg Asp Arg Asp Leu Val Ala Pro Glu Arg Ser Val Asp Ile Ser
290                 295                 300

Phe His Gln Leu Ser Gly Asn Glu Ile Pro Val Ile Glu Arg Leu Tyr
305                 310                 315                 320

Glu Arg Gly Gly Val Glu Leu Pro Gln Arg Val Arg Asp Arg Phe Gln
                325                 330                 335

Arg Tyr Leu Asp Gly Asn Pro Arg Gly Lys His Gly Arg Ile Arg Tyr
            340                 345                 350

Gln Leu Gln Arg His Phe Gly Ile Ser Ala Asp Glu Leu Arg Ala Arg
            355                 360                 365

Phe Gly Phe Tyr Phe Asp Lys Phe Asp Val Arg Pro Glu
            370                 375                 380

<210> SEQ ID NO 11
<211> LENGTH: 1392
<212> TYPE: DNA
<213> ORGANISM: Mycobacterium avium
<220> FEATURE:
<221> NAME/KEY: CDS
<222> LOCATION: (1)...(1392)

<400> SEQUENCE: 11 atg cct gga gcc gcg ccg ccg gca cag ctc ggt gac gaa ccg cgg cgt    48
Met Pro Gly Ala Ala Pro Pro Ala Gln Leu Gly Asp Glu Pro Arg Arg
  1               5                  10                  15 gcg gcc gga cgc gga cgg acg ggt gcg cat cgc gat ctc cgc gcg gga    96
Ala Ala Gly Arg Gly Arg Thr Gly Ala His Arg Asp Leu Arg Ala Gly
                 20                  25                  30 ctt cgg gtt tgg cca ttg gct gga cac cgg cgg ccg gca tcg cgg ctt   144
Leu Arg Val Trp Pro Leu Ala Gly His Arg Arg Pro Ala Ser Arg Leu
         35                  40                  45
```

-continued

| | |
|---|---|
| cgt cgt gct gcg ctg gct gga caa ccc gag ccc gcc cga ggt cgc ggt<br>Arg Arg Ala Ala Leu Ala Gly Gln Pro Glu Pro Ala Arg Gly Arg Gly<br>50                      55                      60 | 192 |
| gtc ggt gcg cga agc gcg gga gcg acc gtg agc ctg cag gac cgg ttc<br>Val Gly Ala Arg Ser Ala Gly Ala Thr Val Ser Leu Gln Asp Arg Phe<br>65                      70                      75                      80 | 240 |
| gcc ccg gaa cgg ctg atc gcc gcc gcc tgt gag gag gcc ggc agc gac<br>Ala Pro Glu Arg Leu Ile Ala Ala Ala Cys Glu Glu Ala Gly Ser Asp<br>                      85                      90                      95 | 288 |
| gac ttc ggc gcc gag ggc tgg cgg ccc ggg ctg cac cgc ctc acc gac<br>Asp Phe Gly Ala Glu Gly Trp Arg Pro Gly Leu His Arg Leu Thr Asp<br>              100                      105                      110 | 336 |
| ggg ctg atc aac gac gcg cgg ctg tcc gac atc ggc gtc gag atc gct<br>Gly Leu Ile Asn Asp Ala Arg Leu Ser Asp Ile Gly Val Glu Ile Ala<br>                      115                      120                      125 | 384 |
| cac ctg gac atc atg cgg gcg ctg aag aac cgg ctc aac gta atc gct<br>His Leu Asp Ile Met Arg Ala Leu Lys Asn Arg Leu Asn Val Ile Ala<br>130                        135                      140 | 432 |
| tgg cgc aaa gca cat ccc gag gtg gcc gag cag aag atc agc gcc ccg<br>Trp Arg Lys Ala His Pro Glu Val Ala Glu Gln Lys Ile Ser Ala Pro<br>145                        150                      155                      160 | 480 |
| atc ttc atc gtc ggc cag ccg cgc acc ggg acg acg atc ctc tac gac<br>Ile Phe Ile Val Gly Gln Pro Arg Thr Gly Thr Thr Ile Leu Tyr Asp<br>                      165                      170                      175 | 528 |
| ctg ctc gcc cag gat ccc gcg ctg cgc gcg ccg ctc acc tgg gag gtc<br>Leu Leu Ala Gln Asp Pro Ala Leu Arg Ala Pro Leu Thr Trp Glu Val<br>                      180                      185                      190 | 576 |
| gac gag ccc tgt ccg gtg ccg cgg ccc gag acc tat cac gac gat ccg<br>Asp Glu Pro Cys Pro Val Pro Arg Pro Glu Thr Tyr His Asp Asp Pro<br>              195                      200                      205 | 624 |
| cgc atc gcc cgg aca cag gcc ggc atc gac ctg tcc gag cag atc atg<br>Arg Ile Ala Arg Thr Gln Ala Gly Ile Asp Leu Ser Glu Gln Ile Met<br>210                        215                      220 | 672 |
| ccc ggg ttc ctg gcc ttt cac ccg atg ggc gcg ctg gtc ggg cag gag<br>Pro Gly Phe Leu Ala Phe His Pro Met Gly Ala Leu Val Gly Gln Glu<br>225                        230                      235                      240 | 720 |
| tgt gtg cgc atc acc gcg gcc gag ttc gtc agc atg atc ttc tct gtg<br>Cys Val Arg Ile Thr Ala Ala Glu Phe Val Ser Met Ile Phe Ser Val<br>                      245                      250                      255 | 768 |
| cag tac cgg ctg ccg aac tac tac cgc tgg ctg ctg tac gag gcg gac<br>Gln Tyr Arg Leu Pro Asn Tyr Tyr Arg Trp Leu Leu Tyr Glu Ala Asp<br>                      260                      265                      270 | 816 |
| cac gcg ggc gcc tac cgc ttc cac cga att ttc ctg cag cac ttg cag<br>His Ala Gly Ala Tyr Arg Phe His Arg Ile Phe Leu Gln His Leu Gln<br>                      275                      280                      285 | 864 |
| tcc ggc gtg ccc ggg cag tgg ttg ctg aaa tcc ccg gcg cac ctg tgg<br>Ser Gly Val Pro Gly Gln Trp Leu Leu Lys Ser Pro Ala His Leu Trp<br>              290                      295                      300 | 912 |
| cag ctg gat gcg ctg ctg gcc gag tac ccg gac gcg ctg atc gtg cag<br>Gln Leu Asp Ala Leu Leu Ala Glu Tyr Pro Asp Ala Leu Ile Val Gln<br>305                        310                      315                      320 | 960 |
| acc cac cgc gat ccg ctc aac gtc atc tcc tcc atc gcg gcg ctg acc<br>Thr His Arg Asp Pro Leu Asn Val Ile Ser Ser Ile Ala Ala Leu Thr<br>                      325                      330                      335 | 1008 |
| cat cac ctg cgc ggg atg tgt agc gac gag tcc agc atc acc gag tgc<br>His His Leu Arg Gly Met Cys Ser Asp Glu Ser Ser Ile Thr Glu Cys<br>                      340                      345                      350 | 1056 |
| gcg gcg cag tcc tac gag gag atc gtc gtg ggc ctg gac cgc gag atg<br>Ala Ala Gln Ser Tyr Glu Glu Ile Val Val Gly Leu Asp Arg Glu Met | 1104 |

```
                355                 360                 365
gcc ctg cgc gac cgg ggc gcc gtg ccg ccc ggg cgc gtg atc gac gtg    1152
Ala Leu Arg Asp Arg Gly Ala Val Pro Pro Gly Arg Val Ile Asp Val
    370                 375                 380 cgg tac gcc gat ttc atg aag gac ccg tgg acc acg atc aaa gac atc    1200
Arg Tyr Ala Asp Phe Met Lys Asp Pro Trp Thr Thr Ile Lys Asp Ile
385                 390                 395                 400 tat gag cgg ctg gac cgc gag ctg cgg ccc gat gcc gag cag aga atg    1248
Tyr Glu Arg Leu Asp Arg Glu Leu Arg Pro Asp Ala Glu Gln Arg Met
                405                 410                 415 cgc gaa ttc ctc gcg tcg cat ccc tcc gac ggt ggg cgc agc cgc tac    1296
Arg Glu Phe Leu Ala Ser His Pro Ser Asp Gly Gly Arg Ser Arg Tyr
            420                 425                 430 acc tgg tcg gac acc ggg ctg gac gcc ggt gcg gtg cgt gag cgg gtg    1344
Thr Trp Ser Asp Thr Gly Leu Asp Ala Gly Ala Val Arg Glu Arg Val
        435                 440                 445 cgc gcc tat cag gac cgc tac ggg gta ccc acc gag gcg ttg cgc tga    1392
Arg Ala Tyr Gln Asp Arg Tyr Gly Val Pro Thr Glu Ala Leu Arg  *
    450                 455                 460

<210> SEQ ID NO 12
<211> LENGTH: 463
<212> TYPE: PRT
<213> ORGANISM: Mycobacterium avium

<400> SEQUENCE: 12

Met Pro Gly Ala Ala Pro Pro Ala Gln Leu Gly Asp Glu Pro Arg Arg
1               5                   10                  15

Ala Ala Gly Arg Gly Arg Thr Gly Ala His Arg Asp Leu Arg Ala Gly
            20                  25                  30

Leu Arg Val Trp Pro Leu Ala Gly His Arg Arg Pro Ala Ser Arg Leu
        35                  40                  45

Arg Arg Ala Ala Leu Ala Gly Gln Pro Glu Pro Ala Arg Gly Arg Gly
    50                  55                  60

Val Gly Ala Arg Ser Ala Gly Ala Thr Val Ser Leu Gln Asp Arg Phe
65                  70                  75                  80

Ala Pro Glu Arg Leu Ile Ala Ala Cys Glu Ala Gly Ser Asp
                85                  90                  95

Asp Phe Gly Ala Glu Gly Trp Arg Pro Gly Leu His Arg Leu Thr Asp
            100                 105                 110

Gly Leu Ile Asn Asp Ala Arg Leu Ser Asp Ile Gly Val Glu Ile Ala
        115                 120                 125

His Leu Asp Ile Met Arg Ala Leu Lys Asn Arg Leu Asn Val Ile Ala
    130                 135                 140

Trp Arg Lys Ala His Pro Glu Val Ala Glu Gln Lys Ile Ser Ala Pro
145                 150                 155                 160

Ile Phe Ile Val Gly Gln Pro Arg Thr Gly Thr Thr Ile Leu Tyr Asp
                165                 170                 175

Leu Leu Ala Gln Asp Pro Ala Leu Arg Ala Pro Leu Thr Trp Glu Val
            180                 185                 190

Asp Glu Pro Cys Pro Val Pro Arg Pro Glu Thr Tyr His Asp Asp Pro
        195                 200                 205

Arg Ile Ala Arg Thr Gln Ala Gly Ile Asp Leu Ser Glu Gln Ile Met
    210                 215                 220

Pro Gly Phe Leu Ala Phe His Pro Met Gly Ala Leu Val Gly Gln Glu
225                 230                 235                 240
```

```
Cys Val Arg Ile Thr Ala Ala Glu Phe Val Ser Met Ile Phe Ser Val
                245                 250                 255

Gln Tyr Arg Leu Pro Asn Tyr Tyr Arg Trp Leu Leu Tyr Glu Ala Asp
                260                 265                 270

His Ala Gly Ala Tyr Arg Phe His Arg Ile Phe Leu Gln His Leu Gln
            275                 280                 285

Ser Gly Val Pro Gly Gln Trp Leu Leu Lys Ser Pro Ala His Leu Trp
        290                 295                 300

Gln Leu Asp Ala Leu Leu Ala Glu Tyr Pro Asp Ala Leu Ile Val Gln
305                 310                 315                 320

Thr His Arg Asp Pro Leu Asn Val Ile Ser Ser Ile Ala Ala Leu Thr
                325                 330                 335

His His Leu Arg Gly Met Cys Ser Asp Glu Ser Ser Ile Thr Glu Cys
                340                 345                 350

Ala Ala Gln Ser Tyr Glu Glu Ile Val Val Gly Leu Asp Arg Glu Met
            355                 360                 365

Ala Leu Arg Asp Arg Gly Ala Val Pro Pro Gly Arg Val Ile Asp Val
        370                 375                 380

Arg Tyr Ala Asp Phe Met Lys Asp Pro Trp Thr Thr Ile Lys Asp Ile
385                 390                 395                 400

Tyr Glu Arg Leu Asp Arg Glu Leu Arg Pro Asp Ala Glu Gln Arg Met
                405                 410                 415

Arg Glu Phe Leu Ala Ser His Pro Ser Asp Gly Gly Arg Ser Arg Tyr
                420                 425                 430

Thr Trp Ser Asp Thr Gly Leu Asp Ala Gly Ala Val Arg Glu Arg Val
            435                 440                 445

Arg Ala Tyr Gln Asp Arg Tyr Gly Val Pro Thr Glu Ala Leu Arg
        450                 455                 460

<210> SEQ ID NO 13
<211> LENGTH: 139
<212> TYPE: PRT
<213> ORGANISM: Mycobacterium bovis

<400> SEQUENCE: 13

Ile Lys Arg Pro Ile Phe Val Thr Gly Leu Val Arg Thr Gly Thr Thr
1               5                   10                  15

Ala Leu His Arg Leu Leu Gly Ala Asp Pro Ala His Gln Gly Leu His
                20                  25                  30

Met Trp Leu Ala Glu Tyr Pro Gln Pro Arg Pro Pro Arg Glu Thr Trp
            35                  40                  45

Glu Ser Asn Pro Leu Tyr Arg Gln Leu Asp Ala Gln Phe Thr Gln His
        50                  55                  60

His Ala Glu Asn Pro Gly Tyr Thr Gly Leu His Phe Met Ala Ala Tyr
65                  70                  75                  80

Glu Leu Glu Glu Cys Trp Gln Leu Leu Arg Gln Ser Leu His Ser Val
                85                  90                  95

Ser Tyr Glu Ala Leu Ala His Val Pro Ser Tyr Ala Asp Trp Leu Ser
                100                 105                 110

Arg Gln Asp Trp Thr Pro Ser Tyr Cys Arg His Arg Arg Asn Leu Gln
            115                 120                 125

Leu Ile Gly Leu Asn Asp Ala Glu Lys Arg Trp
        130                 135

<210> SEQ ID NO 14
```

```
<211> LENGTH: 1155
<212> TYPE: DNA
<213> ORGANISM: Mycobacterium tuberculosis
<220> FEATURE:
<221> NAME/KEY: CDS
<222> LOCATION: (1)...(1155)

<400> SEQUENCE: 14 atg act cgg cgt ccc gat cgg aaa gat gtg gcc acc gtc gac gaa ctg      48
Met Thr Arg Arg Pro Asp Arg Lys Asp Val Ala Thr Val Asp Glu Leu
 1               5                  10                  15 cac gca tcg gct acc aaa ctg gtg ggt ctc gac gat ttt ggc acc gac      96
His Ala Ser Ala Thr Lys Leu Val Gly Leu Asp Asp Phe Gly Thr Asp
             20                  25                  30 gac gac aac tac cgt gag gcg ctg ggt gtg ttg ctg gac gct tac cag     144
Asp Asp Asn Tyr Arg Glu Ala Leu Gly Val Leu Leu Asp Ala Tyr Gln
         35                  40                  45 ggc gaa gcc ggc ctc acc gtg ttg ggc agc aag atg aac cgg ttc ttc     192
Gly Glu Ala Gly Leu Thr Val Leu Gly Ser Lys Met Asn Arg Phe Phe
 50                  55                  60 ctg cgc ggt gcg ctg gtg gcc agg cta ctg tcc cag tcc gcg tgg aag     240
Leu Arg Gly Ala Leu Val Ala Arg Leu Leu Ser Gln Ser Ala Trp Lys
 65                  70                  75                  80 cag tat ccg gag cac gtc gac gtt gcc atc aaa cgg cct atc ttc gtc     288
Gln Tyr Pro Glu His Val Asp Val Ala Ile Lys Arg Pro Ile Phe Val
                 85                  90                  95 acc ggg ttg gtg cgc acc gga acc act gcg ctg cac cgg ctg ctg ggc     336
Thr Gly Leu Val Arg Thr Gly Thr Thr Ala Leu His Arg Leu Leu Gly
            100                 105                 110 gcc gac ccg gcc cac caa ggc ctg cac atg tgg ctg gcc gag tac ccg     384
Ala Asp Pro Ala His Gln Gly Leu His Met Trp Leu Ala Glu Tyr Pro
        115                 120                 125 cag ccg cgc ccc ccg cgc gag acc tgg gag tca aac ccg ttg tat cgc     432
Gln Pro Arg Pro Pro Arg Glu Thr Trp Glu Ser Asn Pro Leu Tyr Arg
    130                 135                 140 cag ctc gat gca cag ttc acc cag cat cat gcc gag aat ccg gga tac     480
Gln Leu Asp Ala Gln Phe Thr Gln His His Ala Glu Asn Pro Gly Tyr
145                 150                 155                 160 acc ggc ttg cat ttc atg gcg gcc tac gag ttg gag gag tgt tgg cag     528
Thr Gly Leu His Phe Met Ala Ala Tyr Glu Leu Glu Glu Cys Trp Gln
                165                 170                 175 ctg ttg cgg cag tcg ctg cat tcg gtg tcg tac gag gcg ctg gcg cat     576
Leu Leu Arg Gln Ser Leu His Ser Val Ser Tyr Glu Ala Leu Ala His
            180                 185                 190 gta ccc agc tat gcc gac tgg ttg tca cgc cag gac tgg acg ccg tcg     624
Val Pro Ser Tyr Ala Asp Trp Leu Ser Arg Gln Asp Trp Thr Pro Ser
        195                 200                 205 tat tgc cgg cac cgc cgc aac ctg cag ctg att ggg ctc aac gat gcc     672
Tyr Cys Arg His Arg Arg Asn Leu Gln Leu Ile Gly Leu Asn Asp Ala
    210                 215                 220 gaa aag cgg tgg gta cta aag aat ccg agt cat cta ttt gcc ctg gat     720
Glu Lys Arg Trp Val Leu Lys Asn Pro Ser His Leu Phe Ala Leu Asp
225                 230                 235                 240 gcg ctg atg gcg acc tat ccc gat gcc ctg gtg gtg cag act cac cgg     768
Ala Leu Met Ala Thr Tyr Pro Asp Ala Leu Val Val Gln Thr His Arg
                245                 250                 255 ccg gtg gag acg atc atg gcg tcg atg tgc tcg ctg gcg cag cac acc     816
Pro Val Glu Thr Ile Met Ala Ser Met Cys Ser Leu Ala Gln His Thr
            260                 265                 270 aca gaa ggg tgg tcg acg aag ttt gtg ggc gcc cag atc ggt gcg gac     864
Thr Glu Gly Trp Ser Thr Lys Phe Val Gly Ala Gln Ile Gly Ala Asp
```

-continued

```
             275                280                285
gcg atg gac acc tgg tcg cgt ggg ctg gag cgg ttc aat gcc gca cgg      912
Ala Met Asp Thr Trp Ser Arg Gly Leu Glu Arg Phe Asn Ala Ala Arg
    290                295                300 gcc aaa tat gat tcg gcc cag ttc tac gac gtg gac tac cac gac ttg      960
Ala Lys Tyr Asp Ser Ala Gln Phe Tyr Asp Val Asp Tyr His Asp Leu
305                310                315                320 att gcc gat ccg ctg ggt acg gtg gca gat atc tac cgg cac ttc ggg     1008
Ile Ala Asp Pro Leu Gly Thr Val Ala Asp Ile Tyr Arg His Phe Gly
                325                330                335 ttg acg ctg tcc gac gag gct cga cag gca atg aca acc gtc cac gcc     1056
Leu Thr Leu Ser Asp Glu Ala Arg Gln Ala Met Thr Thr Val His Ala
            340                345                350 gag agc cag agc ggt gcc cgg gcc cca aag cat tcc tat tcg ttg gct     1104
Glu Ser Gln Ser Gly Ala Arg Ala Pro Lys His Ser Tyr Ser Leu Ala
        355                360                365 gac tac ggg ctc acg gtc gaa atg gtc aaa gag cgg ttc gcc ggg ctg     1152
Asp Tyr Gly Leu Thr Val Glu Met Val Lys Glu Arg Phe Ala Gly Leu
    370                375                380 tga                                                                  1155
 *
```

<210> SEQ ID NO 15
<211> LENGTH: 384
<212> TYPE: PRT
<213> ORGANISM: Mycobacterium tuberculosis

<400> SEQUENCE: 15

```
Met Thr Arg Arg Pro Asp Arg Lys Asp Val Ala Thr Val Asp Glu Leu
 1               5                  10                  15

His Ala Ser Ala Thr Lys Leu Val Gly Leu Asp Asp Phe Gly Thr Asp
                20                  25                  30

Asp Asp Asn Tyr Arg Glu Ala Leu Gly Val Leu Asp Ala Tyr Gln
            35                  40                  45

Gly Glu Ala Gly Leu Thr Val Leu Gly Ser Lys Met Asn Arg Phe Phe
        50                  55                  60

Leu Arg Gly Ala Leu Val Ala Arg Leu Leu Ser Gln Ser Ala Trp Lys
65                  70                  75                  80

Gln Tyr Pro Glu His Val Asp Val Ala Ile Lys Arg Pro Ile Phe Val
                85                  90                  95

Thr Gly Leu Val Arg Thr Gly Thr Thr Ala Leu His Arg Leu Leu Gly
                100                 105                 110

Ala Asp Pro Ala His Gln Gly Leu His Met Trp Leu Ala Glu Tyr Pro
            115                 120                 125

Gln Pro Arg Pro Arg Glu Thr Trp Glu Ser Asn Pro Leu Tyr Arg
        130                 135                 140

Gln Leu Asp Ala Gln Phe Thr Gln His Ala Glu Asn Pro Gly Tyr
145                 150                 155                 160

Thr Gly Leu His Phe Met Ala Ala Tyr Glu Leu Glu Glu Cys Trp Gln
                165                 170                 175

Leu Leu Arg Gln Ser Leu His Ser Val Ser Tyr Glu Ala Leu Ala His
                180                 185                 190

Val Pro Ser Tyr Ala Asp Trp Leu Ser Arg Gln Asp Trp Thr Pro Ser
            195                 200                 205

Tyr Cys Arg His Arg Arg Asn Leu Gln Leu Ile Gly Leu Asn Asp Ala
        210                 215                 220
```

```
Glu Lys Arg Trp Val Leu Lys Asn Pro Ser His Leu Phe Ala Leu Asp
225                 230                 235                 240

Ala Leu Met Ala Thr Tyr Pro Asp Ala Leu Val Val Gln Thr His Arg
                245                 250                 255

Pro Val Glu Thr Ile Met Ala Ser Met Cys Ser Leu Ala Gln His Thr
            260                 265                 270

Thr Glu Gly Trp Ser Thr Lys Phe Val Gly Ala Gln Ile Gly Ala Asp
        275                 280                 285

Ala Met Asp Thr Trp Ser Arg Gly Leu Glu Arg Phe Asn Ala Ala Arg
    290                 295                 300

Ala Lys Tyr Asp Ser Ala Gln Phe Tyr Asp Val Asp Tyr His Asp Leu
305                 310                 315                 320

Ile Ala Asp Pro Leu Gly Thr Val Ala Asp Ile Tyr Arg His Phe Gly
                325                 330                 335

Leu Thr Leu Ser Asp Glu Ala Arg Gln Ala Met Thr Thr Val His Ala
                340                 345                 350

Glu Ser Gln Ser Gly Ala Arg Ala Pro Lys His Ser Tyr Ser Leu Ala
            355                 360                 365

Asp Tyr Gly Leu Thr Val Glu Met Val Lys Glu Arg Phe Ala Gly Leu
        370                 375                 380

<210> SEQ ID NO 16
<211> LENGTH: 978
<212> TYPE: DNA
<213> ORGANISM: Mycobacterium avium
<220> FEATURE:
<221> NAME/KEY: CDS
<222> LOCATION: (1)...(978)

<400> SEQUENCE: 16 atg aat cgc ttc ttt ctg cgc ggc gcc ctg gtg gcg cgc ctg ctg tcg     48
Met Asn Arg Phe Phe Leu Arg Gly Ala Leu Val Ala Arg Leu Leu Ser
1               5                   10                  15 gag tcg gcc tgg aag caa tac ccg cag tac gcc gac gtc gcg atc caa     96
Glu Ser Ala Trp Lys Gln Tyr Pro Gln Tyr Ala Asp Val Ala Ile Gln
            20                  25                  30 cgg ccg atc ttc gtc acc ggc ctg gtg cgc acc ggg acc acg gcg ctg    144
Arg Pro Ile Phe Val Thr Gly Leu Val Arg Thr Gly Thr Thr Ala Leu
        35                  40                  45 cac cgg ctg ctg ggc gcc gat ccc gcg cat cag ggc ctg cac atg tgg    192
His Arg Leu Leu Gly Ala Asp Pro Ala His Gln Gly Leu His Met Trp
    50                  55                  60 ctg gcc gaa ttc ccg cag ccg cgg ccg ccg cgc gag acc tgg gag tcc    240
Leu Ala Glu Phe Pro Gln Pro Arg Pro Pro Arg Glu Thr Trp Glu Ser
65                  70                  75                  80 aac ccg ctg tac cgc cag ctc gac gcg caa ttc acc cag cac cac cgg    288
Asn Pro Leu Tyr Arg Gln Leu Asp Ala Gln Phe Thr Gln His His Arg
                85                  90                  95 gac aac ccc ggc tac acc ggg ctg cac ttc atg gcc gcc tac gag ctg    336
Asp Asn Pro Gly Tyr Thr Gly Leu His Phe Met Ala Ala Tyr Glu Leu
            100                 105                 110 gag gag tgc tgg cag ctg ctg cgg cag tcg ctg cac tcg gtg tcg tat    384
Glu Glu Cys Trp Gln Leu Leu Arg Gln Ser Leu His Ser Val Ser Tyr
        115                 120                 125 gaa acg ctg gcg cac gtc ccc agt tac gcg cag tgg ctg tcc gaa cag    432
Glu Thr Leu Ala His Val Pro Ser Tyr Ala Gln Trp Leu Ser Glu Gln
    130                 135                 140 gac tgg acg ccg tcg tat cag cgg cac cgc cgc aac ctt cag ctg atc    480
Asp Trp Thr Pro Ser Tyr Gln Arg His Arg Arg Asn Leu Gln Leu Ile
```

```
                      145                 150                 155                 160
ggg ctc aac gac gcc gat aag cgc tgg gtg ctg aag aac ccc agc cac       528
Gly Leu Asn Asp Ala Asp Lys Arg Trp Val Leu Lys Asn Pro Ser His
                    165                 170                 175 ctg ttc gcg ctg gac gcg ttg atg gcc acc tac ccg gat gcg ctg gtg       576
Leu Phe Ala Leu Asp Ala Leu Met Ala Thr Tyr Pro Asp Ala Leu Val
                180                 185                 190 atc cag act cat cgc ccg gtc gaa acg atc atg gcg tcg atg tgc tcg       624
Ile Gln Thr His Arg Pro Val Glu Thr Ile Met Ala Ser Met Cys Ser
                195                 200                 205 ctg gcc cag cac acc gcc gaa gga tgg tcg acc acg ttc gtc ggg gcc       672
Leu Ala Gln His Thr Ala Glu Gly Trp Ser Thr Thr Phe Val Gly Ala
            210                 215                 220 caa atc ggc gct gac gca atg gat acc tgg tcg cgg ggg ctg gag cgg       720
Gln Ile Gly Ala Asp Ala Met Asp Thr Trp Ser Arg Gly Leu Glu Arg
225                 230                 235                 240 ttc aac acc gca cgg gcc aag tac aac ccg gcg cag ttc tac gac gtc       768
Phe Asn Thr Ala Arg Ala Lys Tyr Asn Pro Ala Gln Phe Tyr Asp Val
                245                 250                 255 gac tac aag gag ttg atc gcc gac ccg ctg ggc acc gtg gcc gac atc       816
Asp Tyr Lys Glu Leu Ile Ala Asp Pro Leu Gly Thr Val Ala Asp Ile
                260                 265                 270 tac cgg cac ttc ggc ctg acg ctg acg gag gag gcg aag gcg gcc atg       864
Tyr Arg His Phe Gly Leu Thr Leu Thr Glu Glu Ala Lys Ala Ala Met
                275                 280                 285 gcc aag acc cac gcc gac agc cag tcc ggc gag cgg gcg ccc aag cac       912
Ala Lys Thr His Ala Asp Ser Gln Ser Gly Glu Arg Ala Pro Lys His
            290                 295                 300 agc tac tcg ctg gcc gac tac ggc ctc agc gtg gag acg gtc aag gag       960
Ser Tyr Ser Leu Ala Asp Tyr Gly Leu Ser Val Glu Thr Val Lys Glu
305                 310                 315                 320 cgg ttc gcc ggg ctg tga                                               978
Arg Phe Ala Gly Leu *
                325

<210> SEQ ID NO 17
<211> LENGTH: 325
<212> TYPE: PRT
<213> ORGANISM: Mycobacterium avium

<400> SEQUENCE: 17

Met Asn Arg Phe Phe Leu Arg Gly Ala Leu Val Ala Arg Leu Leu Ser
 1               5                  10                  15

Glu Ser Ala Trp Lys Gln Tyr Pro Gln Tyr Ala Asp Val Ala Ile Gln
            20                  25                  30

Arg Pro Ile Phe Val Thr Gly Leu Val Arg Thr Gly Thr Thr Ala Leu
        35                  40                  45

His Arg Leu Leu Gly Ala Asp Pro Ala His Gln Gly Leu His Met Trp
    50                  55                  60

Leu Ala Glu Phe Pro Gln Pro Arg Pro Arg Glu Thr Trp Glu Ser
65                  70                  75                  80

Asn Pro Leu Tyr Arg Gln Leu Asp Ala Gln Phe Thr Gln His His Arg
                85                  90                  95

Asp Asn Pro Gly Tyr Thr Gly Leu His Phe Met Ala Ala Tyr Glu Leu
            100                 105                 110

Glu Glu Cys Trp Gln Leu Leu Arg Gln Ser Leu His Ser Val Ser Tyr
        115                 120                 125

Glu Thr Leu Ala His Val Pro Ser Tyr Ala Gln Trp Leu Ser Glu Gln
```

```
            130                 135                 140
Asp Trp Thr Pro Ser Tyr Gln Arg His Arg Asn Leu Gln Leu Ile
145                 150                 155                 160

Gly Leu Asn Asp Ala Asp Lys Arg Trp Val Leu Lys Asn Pro Ser His
                165                 170                 175

Leu Phe Ala Leu Asp Ala Leu Met Ala Thr Tyr Pro Asp Ala Leu Val
            180                 185                 190

Ile Gln Thr His Arg Pro Val Glu Thr Ile Met Ala Ser Met Cys Ser
                195                 200                 205

Leu Ala Gln His Thr Ala Glu Gly Trp Ser Thr Thr Phe Val Gly Ala
210                 215                 220

Gln Ile Gly Ala Asp Ala Met Asp Thr Trp Ser Arg Gly Leu Glu Arg
225                 230                 235                 240

Phe Asn Thr Ala Arg Ala Lys Tyr Asn Pro Ala Gln Phe Tyr Asp Val
                245                 250                 255

Asp Tyr Lys Glu Leu Ile Ala Asp Pro Leu Gly Thr Val Ala Asp Ile
                260                 265                 270

Tyr Arg His Phe Gly Leu Thr Leu Thr Glu Glu Ala Lys Ala Ala Met
                275                 280                 285

Ala Lys Thr His Ala Asp Ser Gln Ser Gly Glu Arg Ala Pro Lys His
                290                 295                 300

Ser Tyr Ser Leu Ala Asp Tyr Gly Leu Ser Val Glu Thr Val Lys Glu
305                 310                 315                 320

Arg Phe Ala Gly Leu
                325

<210> SEQ ID NO 18
<211> LENGTH: 139
<212> TYPE: PRT
<213> ORGANISM: Mycobacterium

<400> SEQUENCE: 18

Ile Gln Arg Pro Ile Phe Val Thr Gly Leu Val Arg Thr Gly Thr Thr
1               5                   10                  15

Ala Leu His Arg Leu Leu Gly Ala Asp Pro Ala His Gln Gly Leu His
                20                  25                  30

Met Trp Leu Ala Glu Phe Pro Gln Pro Arg Pro Arg Glu Thr Trp
            35                  40                  45

Glu Ser Asn Pro Leu Tyr Arg Gln Leu Asp Ala Gln Phe Thr Gln His
50                  55                  60

His Arg Asp Asn Pro Gly Tyr Thr Gly Leu His Phe Met Ala Ala Tyr
65                  70                  75                  80

Glu Leu Glu Glu Cys Trp Gln Leu Leu Arg Gln Ser Leu His Ser Val
                85                  90                  95

Ser Tyr Glu Thr Leu Ala His Val Pro Ser Tyr Ala Gln Trp Leu Ser
                100                 105                 110

Glu Gln Asp Trp Thr Pro Ser Tyr Gln Arg His Arg Arg Asn Leu Gln
                115                 120                 125

Leu Ile Gly Leu Asn Asp Ala Asp Lys Arg Trp
130                 135

<210> SEQ ID NO 19
<211> LENGTH: 136
<212> TYPE: PRT
<213> ORGANISM: Mycobacterium bovis
```

```
<400> SEQUENCE: 19

Ala Asp Pro Pro Ile Phe Ile Val Gly His Trp Arg Thr Gly Thr Thr
 1               5                  10                 15

Leu Leu His Glu Leu Leu Val Val Asp Asp Arg His Thr Gly Pro Thr
            20                  25                 30

Gly Tyr Glu Cys Leu Ala Pro His His Phe Leu Leu Thr Glu Trp Phe
        35                  40                  45

Ala Pro Tyr Val Glu Phe Leu Val Ser Lys His Arg Ala Met Asp Asn
    50                  55                  60

Met Asp Leu Ser Leu His His Pro Gln Glu Asp Glu Phe Val Trp Cys
65                  70                  75                  80

Met Gln Gly Leu Pro Ser Pro Tyr Leu Thr Ile Ala Phe Pro Asn Arg
                85                  90                  95

Pro Pro Gln Tyr Glu Glu Tyr Leu Asp Leu Glu Gln Val Ala Pro Arg
                100                 105                 110

Glu Leu Glu Ile Trp Lys Arg Thr Leu Phe Arg Phe Val Gln Gln Val
            115                 120                 125

Tyr Phe Arg Arg Arg Lys Thr Val
    130                 135

<210> SEQ ID NO 20
<211> LENGTH: 1164
<212> TYPE: DNA
<213> ORGANISM: Mycobacterium tuberculosis
<220> FEATURE:
<221> NAME/KEY: CDS
<222> LOCATION: (1)...(1164)

<400> SEQUENCE: 20 atg aag gct ctc cgt tcg tcg tct cga ctt tcc cgg tgg cgc gag tgg      48
Met Lys Ala Leu Arg Ser Ser Ser Arg Leu Ser Arg Trp Arg Glu Trp
 1               5                  10                  15 gcc gca ccg ctg tgg gtc ggc tgc aac ttc tcg gcc tgg atg cgg ctt      96
Ala Ala Pro Leu Trp Val Gly Cys Asn Phe Ser Ala Trp Met Arg Leu
            20                  25                  30 ttg atc cgt aac cgc ttc gcc gtg cat cac agc cgc tgg cac ttc gcg     144
Leu Ile Arg Asn Arg Phe Ala Val His His Ser Arg Trp His Phe Ala
        35                  40                  45 gtc ctc tat acg ttt ctc agc atg gtc aat tcc tgt ctg ggg ttg tgg     192
Val Leu Tyr Thr Phe Leu Ser Met Val Asn Ser Cys Leu Gly Leu Trp
    50                  55                  60 cag aag atc gtt ttc ggt agg cga gtg gcc gaa acg gtg atc gcc gat     240
Gln Lys Ile Val Phe Gly Arg Arg Val Ala Glu Thr Val Ile Ala Asp
65                  70                  75                  80 ccg cca atc ttc att gtt ggg cat tgg cgt acc ggc acc acc ttg ctg     288
Pro Pro Ile Phe Ile Val Gly His Trp Arg Thr Gly Thr Thr Leu Leu
                85                  90                  95 cat gaa ctg ttg gtc gtc gat gat cgc cac acc ggt ccc acc ggc tac     336
His Glu Leu Leu Val Val Asp Asp Arg His Thr Gly Pro Thr Gly Tyr
                100                 105                 110 gaa tgc ctt gcg cca cac cat ttt cta ctg acc gag tgg ttt gcg cca     384
Glu Cys Leu Ala Pro His His Phe Leu Leu Thr Glu Trp Phe Ala Pro
            115                 120                 125 tat gtg gaa ttc ctg gta tcg aag cat cgg gca atg gac aac atg gat     432
Tyr Val Glu Phe Leu Val Ser Lys His Arg Ala Met Asp Asn Met Asp
        130                 135                 140 ttg agc ttg cat cac ccg cag gaa gac gag ttc gtg tgg tgt atg cag     480
Leu Ser Leu His His Pro Gln Glu Asp Glu Phe Val Trp Cys Met Gln
145                 150                 155                 160
```

-continued

```
ggc ctg ccg tcg ccg tat ctg acc atc gca ttc ccg aac cgg ccg ccc      528
Gly Leu Pro Ser Pro Tyr Leu Thr Ile Ala Phe Pro Asn Arg Pro Pro
            165                 170                 175 cag tat gag gag tac ctg gat cta gag cag gtg gca ccg cga gaa cta      576
Gln Tyr Glu Glu Tyr Leu Asp Leu Glu Gln Val Ala Pro Arg Glu Leu
        180                 185                 190 gaa atc tgg aaa cgg acc ctg ttc cgg ttc gtt cag cag gtg tac ttc      624
Glu Ile Trp Lys Arg Thr Leu Phe Arg Phe Val Gln Gln Val Tyr Phe
    195                 200                 205 cgc cgt cgc aag acg gtg atc ctc aag aat cca acg cat agt ttt cga      672
Arg Arg Arg Lys Thr Val Ile Leu Lys Asn Pro Thr His Ser Phe Arg
210                 215                 220 atc aag gtg ctg ctg gag gta ttc ccg caa gcg aag ttc atc cac atc      720
Ile Lys Val Leu Leu Glu Val Phe Pro Gln Ala Lys Phe Ile His Ile
225                 230                 235                 240 gtc cga gat ccc tat gtg gtc tat cca tca acc atc cat ctt cat aag      768
Val Arg Asp Pro Tyr Val Val Tyr Pro Ser Thr Ile His Leu His Lys
                245                 250                 255 gcg ctg tac cgc ata cat ggc ttg caa caa ccg acg ttc gac ggg ttg      816
Ala Leu Tyr Arg Ile His Gly Leu Gln Gln Pro Thr Phe Asp Gly Leu
            260                 265                 270 gac gac aag gtc gtg tcg acc tac gtc gac cta tac cga aag ttg gac      864
Asp Asp Lys Val Val Ser Thr Tyr Val Asp Leu Tyr Arg Lys Leu Asp
        275                 280                 285 gaa ggc cga gaa ctc gtt gac ccc aca cgc ttt tac gaa ttg cgt tat      912
Glu Gly Arg Glu Leu Val Asp Pro Thr Arg Phe Tyr Glu Leu Arg Tyr
    290                 295                 300 gag gat ttg atc ggt gat ccc gag gga cag ctg cgc cgg cta tac cag      960
Glu Asp Leu Ile Gly Asp Pro Glu Gly Gln Leu Arg Arg Leu Tyr Gln
305                 310                 315                 320 cac ctg gga ctg ggc gac ttc gag tgt tac ctg ccg cgt ctg cgg caa     1008
His Leu Gly Leu Gly Asp Phe Glu Cys Tyr Leu Pro Arg Leu Arg Gln
                325                 330                 335 tac cta gct gac cat gcg gac tac aaa acc aac agc tat caa ctg acc     1056
Tyr Leu Ala Asp His Ala Asp Tyr Lys Thr Asn Ser Tyr Gln Leu Thr
            340                 345                 350 gtc gag cag cgt gcg att gtc gat gag cac tgg ggc gag atc atc gac     1104
Val Glu Gln Arg Ala Ile Val Asp Glu His Trp Gly Glu Ile Ile Asp
        355                 360                 365 cgc tac ggc tac gat cgt cac aca cct gag ccg gca cgt ctt cgg cct     1152
Arg Tyr Gly Tyr Asp Arg His Thr Pro Glu Pro Ala Arg Leu Arg Pro
    370                 375                 380 gcg gtt ggc ggc                                                     1164
Ala Val Gly Gly
385
```

<210> SEQ ID NO 21
<211> LENGTH: 388
<212> TYPE: PRT
<213> ORGANISM: Mycobacterium tuberculosis

<400> SEQUENCE: 21

```
Met Lys Ala Leu Arg Ser Ser Arg Leu Ser Arg Trp Arg Glu Trp
1               5                   10                  15

Ala Ala Pro Leu Trp Val Gly Cys Asn Phe Ser Ala Trp Met Arg Leu
            20                  25                  30

Leu Ile Arg Asn Arg Phe Ala Val His His Ser Arg Trp His Phe Ala
        35                  40                  45

Val Leu Tyr Thr Phe Leu Ser Met Val Asn Ser Cys Leu Gly Leu Trp
```

```
                     50                  55                  60
Gln Lys Ile Val Phe Gly Arg Arg Val Ala Glu Thr Val Ile Ala Asp
 65                  70                  75                  80

Pro Pro Ile Phe Ile Val Gly His Trp Arg Thr Gly Thr Thr Leu Leu
                     85                  90                  95

His Glu Leu Leu Val Val Asp Asp Arg His Thr Gly Pro Thr Gly Tyr
                    100                 105                 110

Glu Cys Leu Ala Pro His His Phe Leu Leu Thr Glu Trp Phe Ala Pro
                115                 120                 125

Tyr Val Glu Phe Leu Val Ser Lys His Arg Ala Met Asp Asn Met Asp
            130                 135                 140

Leu Ser Leu His His Pro Gln Glu Asp Glu Phe Val Trp Cys Met Gln
145                 150                 155                 160

Gly Leu Pro Ser Pro Tyr Leu Thr Ile Ala Phe Pro Asn Arg Pro Pro
                165                 170                 175

Gln Tyr Glu Glu Tyr Leu Asp Leu Glu Gln Val Ala Pro Arg Glu Leu
                180                 185                 190

Glu Ile Trp Lys Arg Thr Leu Phe Arg Phe Val Gln Gln Val Tyr Phe
            195                 200                 205

Arg Arg Arg Lys Thr Val Ile Leu Lys Asn Pro Thr His Ser Phe Arg
210                 215                 220

Ile Lys Val Leu Leu Glu Val Phe Pro Gln Ala Lys Phe Ile His Ile
225                 230                 235                 240

Val Arg Asp Pro Tyr Val Val Tyr Pro Ser Thr Ile His Leu His Lys
                245                 250                 255

Ala Leu Tyr Arg Ile His Gly Leu Gln Gln Pro Thr Phe Asp Gly Leu
                260                 265                 270

Asp Asp Lys Val Val Ser Thr Tyr Val Asp Leu Tyr Arg Lys Leu Asp
            275                 280                 285

Glu Gly Arg Glu Leu Val Asp Pro Thr Arg Phe Tyr Glu Leu Arg Tyr
290                 295                 300

Glu Asp Leu Ile Gly Asp Pro Glu Gly Gln Leu Arg Arg Leu Tyr Gln
305                 310                 315                 320

His Leu Gly Leu Gly Asp Phe Glu Cys Tyr Leu Pro Arg Leu Arg Gln
                325                 330                 335

Tyr Leu Ala Asp His Ala Asp Tyr Lys Thr Asn Ser Tyr Gln Leu Thr
                340                 345                 350

Val Glu Gln Arg Ala Ile Val Asp Glu His Trp Gly Glu Ile Ile Asp
            355                 360                 365

Arg Tyr Gly Tyr Asp Arg His Thr Pro Glu Pro Ala Arg Leu Arg Pro
370                 375                 380

Ala Val Gly Gly
385

<210> SEQ ID NO 22
<211> LENGTH: 1143
<212> TYPE: DNA
<213> ORGANISM: Mycobacterium avium
<220> FEATURE:
<221> NAME/KEY: CDS
<222> LOCATION: (1)...(1143)

<400> SEQUENCE: 22 atg ctc gcg gcc gcc gag gcg gag acc ggg ctg cac gac tac ggc gat    48
Met Leu Ala Ala Ala Glu Ala Glu Thr Gly Leu His Asp Tyr Gly Asp
 1               5                  10                  15
```

-continued

| | | |
|---|---|---|
| ccg acg ttg ccg caa cgc ttc acc gtc gcc gtc gaa cac ctg aac gcc<br>Pro Thr Leu Pro Gln Arg Phe Thr Val Ala Val Glu His Leu Asn Ala<br>20 25 30 | 96 | |
| ctg ggg ctg gac gcc gat ggc cgc ttc gaa gcc gcg cag gtg tgt cgc<br>Leu Gly Leu Asp Ala Asp Gly Arg Phe Glu Ala Ala Gln Val Cys Arg<br>35 40 45 | 144 | |
| tgg ctg ctg acc tcc cgc ctg gaa ctc atc gag gac cgc aac cgc tac<br>Trp Leu Leu Thr Ser Arg Leu Glu Leu Ile Glu Asp Arg Asn Arg Tyr<br>50 55 60 | 192 | |
| ccg atc ggg gcc gag gtg atc gac gcg ccg atg ttc gtc act ggt gaa<br>Pro Ile Gly Ala Glu Val Ile Asp Ala Pro Met Phe Val Thr Gly Glu<br>65 70 75 80 | 240 | |
| cct cgt tcg ggc aca acg ctt atg cac gcg ctg atg tcg gtc gac ccg<br>Pro Arg Ser Gly Thr Thr Leu Met His Ala Leu Met Ser Val Asp Pro<br>85 90 95 | 288 | |
| cac gcg cgg gcg ttg cgg ttc tgg gag gtg atg tac ccg tcg ccg ccg<br>His Ala Arg Ala Leu Arg Phe Trp Glu Val Met Tyr Pro Ser Pro Pro<br>100 105 110 | 336 | |
| ccg ggg ctg gcg ggg ccc gac gac gac cgc cgg gcg cgg gcg gac gcc<br>Pro Gly Leu Ala Gly Pro Asp Asp Asp Arg Arg Ala Arg Ala Asp Ala<br>115 120 125 | 384 | |
| gac tgg cgt gag atc aac gcg aag atg ccg aag tgg ctg cac agc cac<br>Asp Trp Arg Glu Ile Asn Ala Lys Met Pro Lys Trp Leu His Ser His<br>130 135 140 | 432 | |
| ccc tac aac gac atg ctg ggc gac ggc ctg ccc gaa gac gaa cgc acc<br>Pro Tyr Asn Asp Met Leu Gly Asp Gly Leu Pro Glu Asp Glu Arg Thr<br>145 150 155 160 | 480 | |
| tgg gcg ttc gac ttc cgg gtg atg acg ccc acc gcg tgg tgg cgg gtg<br>Trp Ala Phe Asp Phe Arg Val Met Thr Pro Thr Ala Trp Trp Arg Val<br>165 170 175 | 528 | |
| ccg atg cag tcg ctg gtc gcc ggc ctg ccc acc gac ccg gcc gcg cag<br>Pro Met Gln Ser Leu Val Ala Gly Leu Pro Thr Asp Pro Ala Ala Gln<br>180 185 190 | 576 | |
| tac cgg ctg cac aaa gcg atg ctg caa cag ctg caa tac aac agg ccg<br>Tyr Arg Leu His Lys Ala Met Leu Gln Gln Leu Gln Tyr Asn Arg Pro<br>195 200 205 | 624 | |
| cga aag tat tgg gtg ctg aag ggc ttt cat ggg ttt cga ctc aag gag<br>Arg Lys Tyr Trp Val Leu Lys Gly Phe His Gly Phe Arg Leu Lys Glu<br>210 215 220 | 672 | |
| ctg ttc gac acc tac ccc gat gcg cgg atg gtg tgg ctg cac cgc gac<br>Leu Phe Asp Thr Tyr Pro Asp Ala Arg Met Val Trp Leu His Arg Asp<br>225 230 235 240 | 720 | |
| ccc gtc cag gtc gcc gcg tcg cgc acc atg atg atg gcc gac atc gcc<br>Pro Val Gln Val Ala Ala Ser Arg Thr Met Met Met Ala Asp Ile Ala<br>245 250 255 | 768 | |
| gag ggc atg gtc ggg ccg gtc gac ctg cac gca gag gcg aag aag cac<br>Glu Gly Met Val Gly Pro Val Asp Leu His Ala Glu Ala Lys Lys His<br>260 265 270 | 816 | |
| ctc gag atg acc cgg gcc agc atc gcc aac acg atg acc aat ccc ctg<br>Leu Glu Met Thr Arg Ala Ser Ile Ala Asn Thr Met Thr Asn Pro Leu<br>275 280 285 | 864 | |
| gtc gac gat ccg cgc atc ctg cac ctg agc tac acc gac ttc atc gcc<br>Val Asp Asp Pro Arg Ile Leu His Leu Ser Tyr Thr Asp Phe Ile Ala<br>290 295 300 | 912 | |
| gat cat gtt ggg gcc gtg cgg cgt tat tac gcg ttc tgc ggg cgc gag<br>Asp His Val Gly Ala Val Arg Arg Tyr Tyr Ala Phe Cys Gly Arg Glu<br>305 310 315 320 | 960 | |
| ctc acg gcc gag gcc gag tcg gcg atg cgg gcc tac ctg gcc gac aac<br>Leu Thr Ala Glu Ala Glu Ser Ala Met Arg Ala Tyr Leu Ala Asp Asn | 1008 | |

```
                      325                 330                 335
ccc  ggc  gac  cgg  tac  gga  aag  ttc  cgc  tat  tcc  acg  caa  ttg  ctg  acc      1056
Pro  Gly  Asp  Arg  Tyr  Gly  Lys  Phe  Arg  Tyr  Ser  Thr  Gln  Leu  Leu  Thr
               340                      345                      350 gac  atc  ggt  gag  gac  ctc  gac  gcg  ctg  cac  gcc  gaa  ttc  cgg  ccg  ttc      1104
Asp  Ile  Gly  Glu  Asp  Leu  Asp  Ala  Leu  His  Ala  Glu  Phe  Arg  Pro  Phe
               355                      360                      365 cgg  gaa  cgg  ttc  ggc  gtc  ccg  atc  gaa  aac  cgg  ggc  tga                     1143
Arg  Glu  Arg  Phe  Gly  Val  Pro  Ile  Glu  Asn  Arg  Gly   *
               370                      375                 380
```

<210> SEQ ID NO 23
<211> LENGTH: 380
<212> TYPE: PRT
<213> ORGANISM: Mycobacterium avium

<400> SEQUENCE: 23

```
Met Leu Ala Ala Glu Ala Glu Thr Gly Leu His Asp Tyr Gly Asp
 1               5                  10                  15

Pro Thr Leu Pro Gln Arg Phe Thr Val Ala Val Glu His Leu Asn Ala
                20                  25                  30

Leu Gly Leu Asp Ala Asp Gly Arg Phe Glu Ala Ala Gln Val Cys Arg
            35                  40                  45

Trp Leu Leu Thr Ser Arg Leu Glu Leu Ile Glu Asp Arg Asn Arg Tyr
 50                  55                  60

Pro Ile Gly Ala Glu Val Ile Asp Ala Pro Met Phe Val Thr Gly Glu
 65                  70                  75                  80

Pro Arg Ser Gly Thr Thr Leu Met His Ala Leu Met Ser Val Asp Pro
                85                  90                  95

His Ala Arg Ala Leu Arg Phe Trp Glu Val Met Tyr Pro Ser Pro Pro
            100                 105                 110

Pro Gly Leu Ala Gly Pro Asp Asp Arg Arg Ala Arg Ala Asp Ala
            115                 120                 125

Asp Trp Arg Glu Ile Asn Ala Lys Met Pro Lys Trp Leu His Ser His
130                 135                 140

Pro Tyr Asn Asp Met Leu Gly Asp Gly Leu Pro Glu Asp Glu Arg Thr
145                 150                 155                 160

Trp Ala Phe Asp Phe Arg Val Met Thr Pro Thr Ala Trp Trp Arg Val
                165                 170                 175

Pro Met Gln Ser Leu Val Ala Gly Leu Pro Thr Asp Pro Ala Ala Gln
            180                 185                 190

Tyr Arg Leu His Lys Ala Met Leu Gln Gln Leu Gln Tyr Asn Arg Pro
            195                 200                 205

Arg Lys Tyr Trp Val Leu Lys Gly Phe His Gly Phe Arg Leu Lys Glu
        210                 215                 220

Leu Phe Asp Thr Tyr Pro Asp Ala Arg Met Val Trp Leu His Arg Asp
225                 230                 235                 240

Pro Val Gln Val Ala Ala Ser Arg Thr Met Met Met Ala Asp Ile Ala
                245                 250                 255

Glu Gly Met Val Gly Pro Val Asp Leu His Ala Glu Ala Lys Lys His
            260                 265                 270

Leu Glu Met Thr Arg Ala Ser Ile Ala Asn Thr Met Thr Asn Pro Leu
            275                 280                 285

Val Asp Asp Pro Arg Ile Leu His Leu Ser Tyr Thr Asp Phe Ile Ala
        290                 295                 300
```

-continued

```
Asp His Val Gly Ala Val Arg Arg Tyr Tyr Ala Phe Cys Gly Arg Glu
305                 310                 315                 320

Leu Thr Ala Glu Ala Glu Ser Ala Met Arg Ala Tyr Leu Ala Asp Asn
                325                 330                 335

Pro Gly Asp Arg Tyr Gly Lys Phe Arg Tyr Ser Thr Gln Leu Leu Thr
            340                 345                 350

Asp Ile Gly Glu Asp Leu Asp Ala Leu His Ala Glu Phe Arg Pro Phe
        355                 360                 365

Arg Glu Arg Phe Gly Val Pro Ile Glu Asn Arg Gly
    370                 375                 380

<210> SEQ ID NO 24
<211> LENGTH: 978
<212> TYPE: DNA
<213> ORGANISM: Mycobacterium tuberculosis
<220> FEATURE:
<221> NAME/KEY: CDS
<222> LOCATION: (1)...(978)

<400> SEQUENCE: 24 atg aat tca gaa cac ccg atg acc gac cgg gtt gtg tat cga tcg ttg      48
Met Asn Ser Glu His Pro Met Thr Asp Arg Val Val Tyr Arg Ser Leu
1               5                   10                  15 atg gcc gac aac ctg cga tgg gat gcc ctg caa ttg cgc gac ggc gac      96
Met Ala Asp Asn Leu Arg Trp Asp Ala Leu Gln Leu Arg Asp Gly Asp
                20                  25                  30 atc att atc tcg gcg ccg tcc aag agc ggc ctg acc tgg aca cag cgc     144
Ile Ile Ile Ser Ala Pro Ser Lys Ser Gly Leu Thr Trp Thr Gln Arg
            35                  40                  45 ctg gtg tcc ctg ctg gtg ttc gac ggg ccc gac ttg ccc gga ccc ttg     192
Leu Val Ser Leu Leu Val Phe Asp Gly Pro Asp Leu Pro Gly Pro Leu
        50                  55                  60 tcg acg gtg tcc ccg tgg ctc gac cag acc att cgg ccc atc gag gaa     240
Ser Thr Val Ser Pro Trp Leu Asp Gln Thr Ile Arg Pro Ile Glu Glu
65                  70                  75                  80 gtg gtc gct act ctc gat gcc cag cag cac cgc cgg ttc atc aag acc     288
Val Val Ala Thr Leu Asp Ala Gln Gln His Arg Arg Phe Ile Lys Thr
                85                  90                  95 cac acg ccg ttg gac ggc ctg gtg ctc gac gac cgc gtc agc tac atc     336
His Thr Pro Leu Asp Gly Leu Val Leu Asp Asp Arg Val Ser Tyr Ile
            100                 105                 110 tgc gta gga cgc gac ccg cgc gat gcc gcg gtg tca atg ctg tac caa     384
Cys Val Gly Arg Asp Pro Arg Asp Ala Ala Val Ser Met Leu Tyr Gln
        115                 120                 125 tcg gcc aac atg aac gaa gac cgg atg cgg att ctg cac gag gcc gta     432
Ser Ala Asn Met Asn Glu Asp Arg Met Arg Ile Leu His Glu Ala Val
130                 135                 140 gtg ccg ttt cac gag cga atc gcc ccc ccg ttt gcg gaa ctc ggt cat     480
Val Pro Phe His Glu Arg Ile Ala Pro Pro Phe Ala Glu Leu Gly His
145                 150                 155                 160 gcg cgc agc ccg acc gag gag ttc cgg gat tgg atg gag ggg ccg aat     528
Ala Arg Ser Pro Thr Glu Glu Phe Arg Asp Trp Met Glu Gly Pro Asn
                165                 170                 175 cag cct ccc cct ggc ata ggt ttc aca cat ctg aag ggg atc ggc act     576
Gln Pro Pro Pro Gly Ile Gly Phe Thr His Leu Lys Gly Ile Gly Thr
            180                 185                 190 ctg gcc aac atc ctg cac cag cta ggc acg gta tgg gtc cgc cgt cac     624
Leu Ala Asn Ile Leu His Gln Leu Gly Thr Val Trp Val Arg Arg His
        195                 200                 205 cta ccc aac gtg gcc ttg ttt cat tac gcc gat tac cag gcg gac ttg     672
```

```
Leu Pro Asn Val Ala Leu Phe His Tyr Ala Asp Tyr Gln Ala Asp Leu
    210                 215                 220 gcg ggc gag ctg ctc cgg ccg gca agg gtc ctc ggt atc gcc gcg acc      720
Ala Gly Glu Leu Leu Arg Pro Ala Arg Val Leu Gly Ile Ala Ala Thr
225                 230                 235                 240 cgc gat cga gcc cgg gac ctg gcg cag tac gcc acg ctg gat gcg atg      768
Arg Asp Arg Ala Arg Asp Leu Ala Gln Tyr Ala Thr Leu Asp Ala Met
                245                 250                 255 cgc tcc cgc gcg tca gaa atc gct cct aac acc acc gac ggc atc tgg      816
Arg Ser Arg Ala Ser Glu Ile Ala Pro Asn Thr Thr Asp Gly Ile Trp
            260                 265                 270 cac agt gac gag cgt ttc ttc cgc cgg ggc ggg agt ggc gac tgg cag      864
His Ser Asp Glu Arg Phe Phe Arg Arg Gly Gly Ser Gly Asp Trp Gln
        275                 280                 285 cag ttc ttc acc gaa gcc gag cac ctg cgc tac tac cac cgc atc aac      912
Gln Phe Phe Thr Glu Ala Glu His Leu Arg Tyr Tyr His Arg Ile Asn
    290                 295                 300 cag ctg gcg cca cct gat ctg ctg gcc tgg gca cac gag ggc cgc cgg      960
Gln Leu Ala Pro Pro Asp Leu Leu Ala Trp Ala His Glu Gly Arg Arg
305                 310                 315                 320 gga tac gac ccg gcc aac                                              978
Gly Tyr Asp Pro Ala Asn
                325

<210> SEQ ID NO 25
<211> LENGTH: 326
<212> TYPE: PRT
<213> ORGANISM: Mycobacterium tuberculosis

<400> SEQUENCE: 25

Met Asn Ser Glu His Pro Met Thr Asp Arg Val Val Tyr Arg Ser Leu
1               5                   10                  15

Met Ala Asp Asn Leu Arg Trp Asp Ala Leu Gln Leu Arg Asp Gly Asp
                20                  25                  30

Ile Ile Ile Ser Ala Pro Ser Lys Ser Gly Leu Thr Trp Thr Gln Arg
            35                  40                  45

Leu Val Ser Leu Leu Val Phe Asp Gly Pro Asp Leu Pro Gly Pro Leu
    50                  55                  60

Ser Thr Val Ser Pro Trp Leu Asp Gln Thr Ile Arg Pro Ile Glu Glu
65                  70                  75                  80

Val Val Ala Thr Leu Asp Ala Gln Gln His Arg Arg Phe Ile Lys Thr
                85                  90                  95

His Thr Pro Leu Asp Gly Leu Val Leu Asp Asp Arg Val Ser Tyr Ile
            100                 105                 110

Cys Val Gly Arg Asp Pro Arg Asp Ala Ala Val Ser Met Leu Tyr Gln
        115                 120                 125

Ser Ala Asn Met Asn Glu Asp Arg Met Arg Ile Leu His Glu Ala Val
130                 135                 140

Val Pro Phe His Glu Arg Ile Ala Pro Pro Phe Ala Glu Leu Gly His
145                 150                 155                 160

Ala Arg Ser Pro Thr Glu Glu Phe Arg Asp Trp Met Glu Gly Pro Asn
                165                 170                 175

Gln Pro Pro Pro Gly Ile Gly Phe Thr His Leu Lys Gly Ile Gly Thr
            180                 185                 190

Leu Ala Asn Ile Leu His Gln Leu Gly Thr Val Trp Val Arg Arg His
        195                 200                 205

Leu Pro Asn Val Ala Leu Phe His Tyr Ala Asp Tyr Gln Ala Asp Leu
```

-continued

```
                210                 215                 220
Ala Gly Glu Leu Leu Arg Pro Ala Arg Val Leu Gly Ile Ala Ala Thr
225                 230                 235                 240

Arg Asp Arg Ala Arg Asp Leu Ala Gln Tyr Ala Thr Leu Asp Ala Met
                245                 250                 255

Arg Ser Arg Ala Ser Glu Ile Ala Pro Asn Thr Thr Asp Gly Ile Trp
                260                 265                 270

His Ser Asp Glu Arg Phe Phe Arg Arg Gly Gly Ser Gly Asp Trp Gln
                275                 280                 285

Gln Phe Phe Thr Glu Ala Glu His Leu Arg Tyr Tyr His Arg Ile Asn
                290                 295                 300

Gln Leu Ala Pro Pro Asp Leu Leu Ala Trp Ala His Glu Gly Arg Arg
305                 310                 315                 320

Gly Tyr Asp Pro Ala Asn
                325

<210> SEQ ID NO 26
<211> LENGTH: 269
<212> TYPE: PRT
<213> ORGANISM: consensus
<220> FEATURE:
<221> NAME/KEY: VARIANT
<222> LOCATION: (1)...(269)
<223> OTHER INFORMATION: Xaa = Any Amino Acid
<220> FEATURE:
<221> NAME/KEY: VARIANT
<222> LOCATION: 2, 6, 7, 8, 9, 10, 11, 12, 13, 15, 16, 17, 19, 23, 24,
      26, 27, 28, 29, 30, 31, 33, 34, 35, 37, 38, 39, 40, 41, 42,
      43, 45, 46, 47, 49, 50, 53, 55, 56, 57, 58, 59, 60, 61,
      63, 64, 65, 67, 68, 69, 71, 72, 75, 77, 86, 88, 89, 93,
      96
<223> OTHER INFORMATION: Xaa = Any Amino Acid
<220> FEATURE:
<221> NAME/KEY: VARIANT
<222> LOCATION: 97, 98, 99, 100, 101, 103, 104, 106, 107, 108, 109, 111,
      113, 115, 116, 117, 118, 119, 120, 121, 122, 123, 124, 125,
      127, 128, 129, 130, 131, 132, 134, 135, 136, 137, 138, 139,
      140, 141, 142, 143, 144, 145, 147, 148, 149, 150, 152
<223> OTHER INFORMATION: Xaa = Any Amino Acid
<220> FEATURE:
<221> NAME/KEY: VARIANT
<222> LOCATION: 153, 154, 155, 156, 157, 158, 159, 160, 161, 162, 163,
      165, 166, 167, 170, 171, 172, 173, 174, 177, 180, 181, 182, 183,
      186, 188, 189, 191, 192, 193, 194, 195, 197, 198, 199, 200,
      202, 203, 204, 207, 210, 212, 213, 214, 215, 216, 217
<223> OTHER INFORMATION: Xaa = Any Amino Acid
<220> FEATURE:
<221> NAME/KEY: VARIANT
<222> LOCATION: 219, 224, 226, 228, 230, 232, 233, 235, 236, 237, 242,
      243, 244, 245, 246, 254, 255, 258, 260, 261, 262, 263, 265, 266,
      268, 269
<223> OTHER INFORMATION: Xaa = Any Amino Acid

<400> SEQUENCE: 26

Leu Xaa Asp Phe Gly Xaa Xaa Xaa Xaa Xaa Xaa Xaa Xaa Tyr Xaa Xaa
1               5                   10                  15

Xaa Leu Xaa Val Ile Leu Xaa Xaa Leu Xaa Xaa Xaa Xaa Xaa Xaa Leu
                20                  25                  30

Xaa Xaa Xaa Gly Xaa Xaa Xaa Xaa Xaa Xaa Xaa Leu Xaa Xaa Xaa Leu
                35                  40                  45

Xaa Xaa Arg Leu Xaa Leu Xaa Xaa Xaa Xaa Xaa Xaa Pro Xaa Xaa
    50                  55                  60

Xaa Asp Xaa Xaa Xaa Ile Xaa Xaa Pro Ile Xaa Val Xaa Gly Leu Pro
65                  70                  75                  80

Arg Thr Gly Thr Thr Xaa Leu Xaa Xaa Leu Leu Gly Xaa Asp Pro Xaa
```

```
                   85                  90                  95
Xaa Xaa Xaa Xaa Xaa Leu Xaa Xaa Trp Xaa Xaa Xaa Xaa Pro Xaa Pro
                100                 105                 110
Xaa Pro Xaa Xaa Xaa Xaa Xaa Xaa Xaa Xaa Xaa Xaa Pro Xaa Xaa
                115                 120                 125
Xaa Xaa Xaa Xaa Ala Xaa Xaa Xaa Xaa Xaa Xaa Xaa Xaa Xaa
        130                 135                 140
Xaa Pro Xaa Xaa Xaa Xaa Leu Xaa Xaa Xaa Xaa Xaa Xaa Xaa Xaa
145                 150                 155                 160
Xaa Xaa Xaa Glu Xaa Xaa Xaa Leu Leu Xaa Xaa Xaa Xaa Ser Val
                165                 170                 175
Xaa Tyr Glu Xaa Xaa Xaa Xaa Val Pro Xaa Tyr Xaa Xaa Trp Xaa Xaa
                180                 185                 190
Xaa Xaa Xaa Asp Xaa Xaa Xaa Xaa Tyr Xaa Xaa Xaa Arg Arg Xaa Leu
                195                 200                 205
Gln Xaa Ile Xaa Xaa Xaa Xaa Xaa Lys Xaa Trp Val Leu Lys Xaa
        210                 215                 220
Pro Xaa His Xaa Phe Xaa Leu Xaa Xaa Leu Xaa Xaa Xaa Tyr Pro Asp
225                 230                 235                 240
Ala Xaa Xaa Xaa Xaa Xaa Val Ile Thr His Arg Asp Pro Xaa Xaa Val
                245                 250                 255
Met Xaa Ser Xaa Xaa Xaa Xaa Met Xaa Xaa Leu Xaa Xaa
                260                 265

<210> SEQ ID NO 27
<211> LENGTH: 254
<212> TYPE: PRT
<213> ORGANISM: Mycobacterium tuberculosis

<400> SEQUENCE: 27

Met Ser Gly Glu Thr Thr Arg Leu Thr Glu Pro Gln Leu Arg Glu Leu
1               5                   10                  15
Ala Ala Arg Gly Ala Ala Glu Leu Asp Gly Ala Thr Ala Thr Asp Met
                20                  25                  30
Leu Arg Trp Thr Asp Glu Thr Phe Gly Asp Ile Gly Gly Ala Gly Gly
            35                  40                  45
Gly Val Ser Gly His Arg Gly Trp Thr Thr Cys Asn Tyr Val Val Ala
        50                  55                  60
Ser Asn Met Ala Asp Ala Val Leu Val Asp Leu Ala Ala Lys Val Arg
65                  70                  75                  80
Pro Gly Val Pro Val Ile Phe Leu Asp Thr Gly Tyr His Phe Val Glu
                85                  90                  95
Thr Ile Gly Thr Arg Asp Ala Ile Glu Ser Val Tyr Asp Val Arg Val
                100                 105                 110
Leu Asn Val Thr Pro Glu His Thr Val Ala Glu Gln Asp Glu Leu Leu
                115                 120                 125
Gly Lys Asp Leu Phe Ala Arg Asn Pro His Glu Cys Cys Arg Leu Arg
        130                 135                 140
Lys Val Val Pro Leu Gly Lys Thr Leu Arg Gly Tyr Ser Ala Trp Val
145                 150                 155                 160
Thr Gly Leu Arg Arg Val Asp Ala Pro Thr Arg Ala Asn Ala Pro Leu
                165                 170                 175
Val Ser Phe Asp Glu Thr Phe Lys Leu Val Lys Val Asn Pro Leu Ala
                180                 185                 190
```

```
Ala Trp Thr Asp Gln Asp Val Gln Glu Tyr Ile Ala Asp Asn Asp Val
        195                 200                 205

Leu Val Asn Pro Leu Val Arg Glu Gly Tyr Pro Ser Ile Gly Cys Ala
        210                 215                 220

Pro Cys Thr Ala Lys Pro Ala Glu Gly Ala Asp Pro Arg Ser Gly Arg
225                 230                 235                 240

Trp Gln Gly Leu Ala Lys Thr Glu Cys Gly Leu His Ala Ser
            245                 250

<210> SEQ ID NO 28
<211> LENGTH: 236
<212> TYPE: PRT
<213> ORGANISM: Mycobacterium smegmatis

<400> SEQUENCE: 28

Met Thr Asp Val Thr Thr Ser Thr Glu Asn Glu Leu Arg Glu Leu Ala
1               5                   10                  15

Glu Arg Gly Ala Ala Glu Leu Ala Asp Ala Ser Ala Glu Glu Leu Leu
            20                  25                  30

Arg Trp Thr Asp Glu His Phe Gly Gly Asn Tyr Val Val Ala Ser Asn
        35                  40                  45

Met Gln Asp Ala Val Leu Val Glu Met Ala Ala Lys Val Arg Pro Gly
    50                  55                  60

Val Asp Val Leu Phe Leu Asp Thr Gly Tyr His Phe Ala Glu Thr Ile
65                  70                  75                  80

Gly Thr Arg Asp Ala Val Glu Ala Val Tyr Asp Val His Val Val Asn
                85                  90                  95

Val Thr Pro Glu Arg Thr Val Ala Glu Gln Asp Glu Leu Leu Gly Lys
            100                 105                 110

Asn Leu Phe Ala Arg Asp Pro Gly Glu Cys Cys Arg Leu Arg Lys Val
        115                 120                 125

Val Pro Leu Thr Asn Ala Leu Lys Gly Tyr Ser Ala Trp Val Thr Gly
    130                 135                 140

Ile Arg Arg Val Glu Ala Pro Thr Arg Ala Asn Ala Pro Leu Ile Ser
145                 150                 155                 160

Trp Asp Asn Ala Phe Gly Leu Val Lys Ile Asn Pro Ile Ala Ala Trp
                165                 170                 175

Thr Asp Glu Asp Met Gln Asn Tyr Ile Asp Ala Asn Gly Ile Leu Val
            180                 185                 190

Asn Pro Leu Val Tyr Glu Gly Tyr Pro Ser Ile Gly Cys Ala Pro Cys
        195                 200                 205

Thr Ser Lys Pro Ile Pro Gly Ala Asp Pro Arg Ser Gly Arg Trp Ala
    210                 215                 220

Gly Leu Ser Lys Thr Glu Cys Gly Leu His Val Ser
225                 230                 235

<210> SEQ ID NO 29
<211> LENGTH: 247
<212> TYPE: PRT
<213> ORGANISM: Mycobacterium avium

<400> SEQUENCE: 29

Met Thr Glu Arg Thr Thr Lys Leu Pro Glu Ala Glu Leu Arg Glu Leu
1               5                   10                  15

Ala Ala Arg Gly Ala Ala Glu Leu Glu Gly Ala Ser Ala Ser Asp Val
            20                  25                  30
```

-continued

```
Leu Arg Trp Thr Asp Glu Thr Phe Gly Gly Val Asn Gly Pro Arg Gly
         35                  40                  45

Trp Ala Thr Cys Asn Tyr Val Val Ala Ser Ser Met Gln Glu Ala Val
     50                  55                  60

Leu Ile Asp Leu Ala Ala Lys Val Arg Pro Gly Val Pro Val Val Phe
 65                  70                  75                  80

Leu Asp Thr Gly Tyr His Phe Ala Glu Thr Ile Gly Thr Arg Asp Ala
                 85                  90                  95

Ile Glu Ser Val Tyr Asp Ile Arg Val Leu Asn Val Thr Pro Glu His
                100                 105                 110

Ser Val Ala Glu Gln Asp Lys Leu Leu Gly Lys Asp Leu Phe Ala Arg
            115                 120                 125

Asp Pro Gly Glu Cys Cys Arg Leu Arg Lys Val Ala Pro Leu Gly Lys
        130                 135                 140

Thr Leu Arg Gly Tyr Ser Ala Trp Val Thr Gly Leu Arg Arg Ser Glu
145                 150                 155                 160

Ala Ala Thr Arg Ala Asn Ala Pro Val Ile Gly Phe Asp Glu Gly Phe
                165                 170                 175

Lys Leu Val Lys Val Asn Pro Met Ala Thr Trp Thr Asp Glu Asp Val
                180                 185                 190

Gln Asn Tyr Ile Asp Glu His Asn Val Leu Val Asn Pro Leu Ile Tyr
            195                 200                 205

Glu Gly Tyr Ser Ser Ile Gly Cys Ala Pro Cys Thr Ala Lys Pro Leu
        210                 215                 220

Ala Gly Ala Asp Pro Arg Ser Gly Arg Trp Gln Gly Leu Ala Lys Thr
225                 230                 235                 240

Glu Cys Gly Leu His Ala Ser
                245
```

<210> SEQ ID NO 30
<211> LENGTH: 254
<212> TYPE: PRT
<213> ORGANISM: consensus
<220> FEATURE:
<221> NAME/KEY: VARIANT
<222> LOCATION: (1)...(254)
<223> OTHER INFORMATION: Xaa = Any Amino Acid
<220> FEATURE:
<221> NAME/KEY: VARIANT
<222> LOCATION: 3, 11, 42, 44, 46, 47, 48, 49, 50, 51, 52, 53, 57, 207, 232
<223> OTHER INFORMATION: Xaa = Any Amino Acid

<400> SEQUENCE: 30

```
Met Ser Xaa Glu Thr Thr Arg Leu Thr Glu Xaa Glu Leu Arg Glu Leu
 1               5                  10                  15

Ala Ala Arg Gly Ala Ala Glu Leu Asp Gly Ala Ser Ala Thr Asp Met
            20                  25                  30

Leu Arg Trp Thr Asp Glu Thr Phe Gly Xaa Ile Xaa Gly Xaa Xaa Xaa
         35                  40                  45

Xaa Xaa Xaa Xaa Xaa Arg Gly Trp Xaa Thr Cys Asn Tyr Val Val Ala
 50                  55                  60

Ser Asn Met Gln Asp Ala Val Leu Val Asp Leu Ala Ala Lys Val Arg
 65                  70                  75                  80

Pro Gly Val Pro Val Ile Phe Leu Asp Thr Gly Tyr His Phe Ala Glu
                 85                  90                  95

Thr Ile Gly Thr Arg Asp Ala Ile Glu Ser Val Tyr Asp Val Arg Val
                100                 105                 110
```

-continued

```
Leu Asn Val Thr Pro Glu His Thr Val Ala Glu Gln Asp Glu Leu Leu
            115                 120                 125
Gly Lys Asp Leu Phe Ala Arg Asp Pro Gly Glu Cys Cys Arg Leu Arg
        130                 135                 140
Lys Val Val Pro Leu Gly Lys Thr Leu Arg Gly Tyr Ser Ala Trp Val
145                 150                 155                 160
Thr Gly Leu Arg Arg Val Glu Ala Pro Thr Arg Ala Asn Ala Pro Leu
                165                 170                 175
Ile Ser Phe Asp Glu Gly Phe Lys Leu Val Lys Val Asn Pro Leu Ala
            180                 185                 190
Ala Trp Thr Asp Glu Asp Val Gln Asn Tyr Ile Asp Asp Asn Xaa Val
        195                 200                 205
Leu Val Asn Pro Leu Val Tyr Glu Gly Tyr Pro Ser Ile Gly Cys Ala
    210                 215                 220
Pro Cys Thr Ala Lys Pro Leu Xaa Gly Ala Asp Pro Arg Ser Gly Arg
225                 230                 235                 240
Trp Gln Gly Leu Ala Lys Thr Glu Cys Gly Leu His Ala Ser
                245                 250

<210> SEQ ID NO 31
<211> LENGTH: 617
<212> TYPE: PRT
<213> ORGANISM: Mycobacterium smegmatis

<400> SEQUENCE: 31

Met Ser Ala Asn Thr Thr Leu Leu Arg Leu Ala Thr Ala Gly Ser Val
1               5                   10                  15
Asp Asp Gly Lys Ser Thr Leu Ile Gly Arg Leu Leu Tyr Asp Ser Lys
            20                  25                  30
Ala Val Met Glu Asp Gln Leu Ala Ala Val Glu Arg Thr Ser Lys Glu
        35                  40                  45
Arg Gly His Asp Tyr Thr Asp Leu Ala Leu Val Thr Asp Gly Leu Arg
    50                  55                  60
Ala Glu Arg Glu Gln Gly Ile Thr Ile Asp Val Ala Tyr Arg Tyr Phe
65                  70                  75                  80
Ala Thr Ala Lys Arg Lys Phe Ile Ile Ala Asp Thr Pro Gly His Ile
                85                  90                  95
Gln Tyr Thr Arg Asn Met Val Thr Gly Thr Ser Thr Ala Gln Leu Ala
            100                 105                 110
Ile Val Leu Val Asp Ala Arg Asn Gly Leu Leu Glu Gln Ser Arg Arg
        115                 120                 125
His Ala Phe Leu Ala Ser Leu Leu Gly Ile Arg His Ile Val Leu Ala
    130                 135                 140
Val Asn Lys Met Asp Leu Ile Gly Trp Asp Gln Glu Arg Phe Glu Ala
145                 150                 155                 160
Ile Arg Asp Glu Phe His Thr Phe Ala Ala Arg Leu Asp Val His Asp
                165                 170                 175
Val Thr Ala Ile Pro Leu Ser Ala Leu Gln Gly Asp Asn Val Val Thr
            180                 185                 190
Lys Ser Asp Lys Thr Pro Trp Tyr Glu Gly Pro Ala Leu Leu Ala His
        195                 200                 205
Leu Glu Asp Val Tyr Ile Ala Gly Asp Arg Asn Leu Val Asp Val Arg
    210                 215                 220
Phe Pro Val Gln Tyr Val Ile Arg Pro Gln Thr Leu Asp His Ala Asp
```

```
            225                 230                 235                 240

His Arg Ser Tyr Ala Gly Thr Val Ala Ser Gly Val Met Arg Pro Gly
                245                 250                 255

Asp Glu Ile Val Val Leu Pro Ser Gly Lys Ser Ser Arg Ile Thr Glu
            260                 265                 270

Ile Ala Gly Pro Gly Gly Pro Val Asp Glu Ala Phe Pro Pro Met Ala
            275                 280                 285

Val Ser Ile Ser Leu Ala Asp Asp Ile Asp Ile Ser Arg Gly Asp Met
            290                 295                 300

Ile Ala Arg Pro Gly Asn Gln Pro Arg Val Thr Gln Asp Phe Asp Ala
305                 310                 315                 320

Thr Val Cys Trp Met Ala Asp Asp Ala Ser Leu Glu Pro Gly Arg Glu
                325                 330                 335

Tyr Leu Ile Lys His Thr Thr Arg Thr Arg Ala Lys Val Val Asp
                340                 345                 350

Leu Asp Tyr Arg Leu Asp Val Asn Thr Leu His Arg Asp Lys Ser Ala
                355                 360                 365

Thr Ala Leu Lys Leu Asn Glu Leu Gly Arg Ile Ser Leu Arg Thr Arg
370                 375                 380

Thr Pro Leu Leu Leu Asp Glu Tyr Ser Arg Asn Pro Ala Thr Gly Ser
385                 390                 395                 400

Phe Ile Leu Ile Asp Pro His Thr Asn Gly Thr Val Gly Ala Gly Met
                405                 410                 415

Val Leu Arg Asp Ala Arg Asn Glu Ser Ala Ser Pro Asn Thr Val Arg
                420                 425                 430

His Glu Asn Leu Ile Thr Ala Glu Asp Arg Leu Thr Arg Gly Arg Thr
                435                 440                 445

Val Trp Phe Thr Gly Leu Ser Gly Ser Gly Lys Ser Ser Val Ala Met
                450                 455                 460

Leu Val Glu Gln Lys Leu Leu Gly Lys Gly Val Pro Ala Tyr Val Leu
465                 470                 475                 480

Asp Gly Asp Asn Leu Arg His Gly Leu Asn Ala Asp Leu Gly Phe Ser
                485                 490                 495

Met Ala Asp Arg Ala Glu Asn Leu Arg Arg Leu Ala His Val Ala Ser
                500                 505                 510

Leu Leu Ala Asp Ser Gly Gln Ile Val Leu Pro Ala Ile Ser Pro
                515                 520                 525

Leu Glu Glu His Arg Glu Leu Ala Arg Arg Val Ser Thr Glu Ser Gly
                530                 535                 540

Val Glu Phe Phe Glu Val Phe Cys Asp Thr Pro Leu Ala Asp Cys Glu
545                 550                 555                 560

Ala Arg Asp Pro Lys Gly Leu Tyr Ala Lys Ala Arg Ala Gly Glu Ile
                565                 570                 575

Thr His Phe Thr Gly Ile Asp Ser Pro Tyr Gln Arg Pro Lys His Pro
                580                 585                 590

Asp Leu Arg Leu Thr Pro Glu His Ser Leu Asp Glu Leu Ala Asp Met
                595                 600                 605

Val Ile Glu Met Leu Glu Thr Arg Arg
    610                 615

<210> SEQ ID NO 32
<211> LENGTH: 616
<212> TYPE: PRT
<213> ORGANISM: Mycobacterium avium
```

<400> SEQUENCE: 32

Met Ala Ala Pro Thr Thr Leu Leu Arg Leu Ala Thr Ala Gly Ser Val
1               5                   10                  15

Asp Asp Gly Lys Ser Thr Leu Ile Gly Arg Leu Leu Tyr Asp Ser Lys
            20                  25                  30

Ala Val Met Glu Asp Gln Trp Ala Ala Val Glu Gln Thr Ser Lys Asp
        35                  40                  45

Arg Gly His Asp Tyr Thr Asp Leu Ala Leu Val Thr Asp Gly Leu Arg
    50                  55                  60

Ala Glu Arg Glu Gln Gly Ile Thr Ile Asp Val Ala Tyr Arg Tyr Phe
65                  70                  75                  80

Ala Thr Pro Lys Arg Lys Phe Ile Ile Ala Asp Thr Pro Gly His Ile
                85                  90                  95

Gln Tyr Thr Arg Asn Met Val Thr Gly Ala Ser Thr Ala Gln Leu Val
            100                 105                 110

Ile Val Leu Val Asp Ala Arg His Gly Leu Leu Glu Gln Ser Arg Arg
        115                 120                 125

His Ala Phe Leu Ala Ser Leu Leu Gly Ile Gln His Ile Val Leu Ala
    130                 135                 140

Val Asn Lys Met Asp Leu Ile Gly Trp Asp Arg Glu Lys Phe Glu Ser
145                 150                 155                 160

Ile Arg Asp Glu Phe His Ala Phe Ala Ala Arg Leu Asp Val His Asp
                165                 170                 175

Val Ala Thr Ile Pro Ile Ser Ala Leu His Gly Asp Asn Val Val Thr
            180                 185                 190

Lys Ser Asp Gln Thr Pro Trp Tyr Glu Gly Pro Ala Leu Leu Ser His
    195                 200                 205

Leu Glu Glu Val Tyr Ile Ala Gly Asp Arg Asn Leu Val Asp Val Arg
210                 215                 220

Phe Pro Val Gln Tyr Val Ile Arg Pro His Thr His Glu His Gln Asp
225                 230                 235                 240

His Arg Ser Tyr Ala Gly Thr Val Ala Ser Gly Val Met Arg Pro Gly
                245                 250                 255

Asp Glu Val Val Val Leu Pro Val Gly Lys Arg Thr Arg Ile Thr Ala
            260                 265                 270

Ile Glu Gly Pro Asn Gly Pro Val Gln Glu Ala Phe Pro Pro Met Ala
    275                 280                 285

Val Ser Leu Thr Leu Ala Asp Glu Ile Asp Ile Ser Arg Gly Asp Leu
290                 295                 300

Ile Ala Arg Thr His Asn Gln Pro Arg Ile Ala Gln Asp Phe Asp Ala
305                 310                 315                 320

Thr Val Cys Trp Met Ala Asp Asn Thr Thr Leu Glu Pro Gly Arg Asp
                325                 330                 335

Tyr Val Ile Lys His Thr Thr Arg Thr Thr His Ala Arg Val Thr Gly
            340                 345                 350

Leu Asp Tyr Arg Leu Asp Val Asn Thr Leu His Arg Asp Lys Thr Ala
    355                 360                 365

Thr Ala Leu Lys Leu Asn Glu Leu Gly Arg Ile Ser Leu Arg Thr Gln
370                 375                 380

Val Pro Leu Leu Leu Asp Glu Tyr Thr Arg Asn Pro Ser Thr Gly Ser
385                 390                 395                 400

Phe Ile Leu Ile Asp Pro His Thr Asn Gly Thr Val Ala Ala Gly Met

```
                405                 410                 415
Val Leu Arg Asp Ala Ser Ala Gln Ala Ala Ser Pro Asn Thr Val Arg
            420                 425                 430

His Lys Ser Ser Ala Ile Ala Ala Ala Arg Pro Arg Gly Lys Thr Val
            435                 440                 445

Trp Phe Thr Gly Leu Ser Gly Ser Gly Lys Ser Ser Val Ala Met Leu
            450                 455                 460

Val Glu Gln Lys Leu Leu Glu Lys Gly Ala Gln Ala Tyr Val Leu Asp
465                 470                 475                 480

Gly Asp Asn Leu Arg His Gly Leu Asn Ala Asp Leu Gly Phe Ser Met
            485                 490                 495

Ala Asp Arg Ala Glu Asn Leu Arg Arg Leu Ala His Val Ala Ala Leu
            500                 505                 510

Leu Ala Asp Cys Gly Asn Val Val Leu Val Pro Ala Ile Ser Pro Leu
            515                 520                 525

Ala Glu Gln Arg Glu Leu Ala Arg Lys Val His Ala Asp Ala Gly Phe
            530                 535                 540

Asp Phe Ile Glu Val Phe Cys Asp Thr Pro Ile Glu Glu Cys Glu Lys
545                 550                 555                 560

Arg Asp Pro Lys Gly Leu Tyr Ala Lys Ala Arg Ala Gly Glu Ile Thr
            565                 570                 575

Gln Phe Thr Gly Ile Asp Ser Pro Tyr Gln Pro Pro Ala Lys Pro Asp
            580                 585                 590

Leu Arg Leu Thr Pro Asp Gly Thr Val Glu Glu Gln Ala Gln Arg Val
            595                 600                 605

Ile Asp Leu Leu Glu Ser Arg Gly
    610                 615

<210> SEQ ID NO 33
<211> LENGTH: 31
<212> TYPE: DNA
<213> ORGANISM: Artificial Sequence
<220> FEATURE:
<223> OTHER INFORMATION: artificial primer

<400> SEQUENCE: 33
gatatacata tgagcggcga gacaaccagg c                              31

<210> SEQ ID NO 34
<211> LENGTH: 28
<212> TYPE: DNA
<213> ORGANISM: Artificial Sequence
<220> FEATURE:
<223> OTHER INFORMATION: artificial primer

<400> SEQUENCE: 34
gtggtgctcg agcgaggcgt gcaacccg                                  28

<210> SEQ ID NO 35
<211> LENGTH: 28
<212> TYPE: DNA
<213> ORGANISM: Artificial Sequence
<220> FEATURE:
<223> OTHER INFORMATION: artificial primer

<400> SEQUENCE: 35 aagggggcata tgagcccgaa cacggtgc                                 28

<210> SEQ ID NO 36
```

```
<211> LENGTH: 36
<212> TYPE: DNA
<213> ORGANISM: Artificial Sequence
<220> FEATURE:
<223> OTHER INFORMATION: artificial primer

<400> SEQUENCE: 36 aagggctcg agttaagacg atgactccaa caggtc                                    36

<210> SEQ ID NO 37
<211> LENGTH: 30
<212> TYPE: DNA
<213> ORGANISM: Artificial Sequence
<220> FEATURE:
<223> OTHER INFORMATION: artificial primer

<400> SEQUENCE: 37
ggggccatgg gtagcggcga gacaaccagg                                          30

<210> SEQ ID NO 38
<211> LENGTH: 35
<212> TYPE: DNA
<213> ORGANISM: Artificial Sequence
<220> FEATURE:
<223> OTHER INFORMATION: artificial primer

<400> SEQUENCE: 38 gggggatcc ctcgagttac gaggcgtgca acccg                                     35

<210> SEQ ID NO 39
<211> LENGTH: 28
<212> TYPE: DNA
<213> ORGANISM: Artificial Sequence
<220> FEATURE:
<223> OTHER INFORMATION: artificial primer

<400> SEQUENCE: 39
ggggccatgg gtagcccgaa cacggtgc                                            28

<210> SEQ ID NO 40
<211> LENGTH: 32
<212> TYPE: DNA
<213> ORGANISM: Artificial Sequence
<220> FEATURE:
<223> OTHER INFORMATION: artificial primer

<400> SEQUENCE: 40
gggccatggg gaccgacgtg acgacgtcaa cg                                       32

<210> SEQ ID NO 41
<211> LENGTH: 29
<212> TYPE: DNA
<213> ORGANISM: Artificial Sequence
<220> FEATURE:
<223> OTHER INFORMATION: artificial primer

<400> SEQUENCE: 41
gggctcgagt cacgagacgt gcagcccgc                                           29

<210> SEQ ID NO 42
<211> LENGTH: 36
<212> TYPE: DNA
<213> ORGANISM: Artificial Sequence
<220> FEATURE:
<223> OTHER INFORMATION: artificial primer

<400> SEQUENCE: 42
```

```
ggggaaccat gggtttaacg tatgataatt gggaag                              36

<210> SEQ ID NO 43
<211> LENGTH: 29
<212> TYPE: DNA
<213> ORGANISM: Artificial Sequence
<220> FEATURE:
<223> OTHER INFORMATION: artificial primer

<400> SEQUENCE: 43
ggggaactcg agttattcat gcagtccgc                                     29

<210> SEQ ID NO 44
<211> LENGTH: 39
<212> TYPE: DNA
<213> ORGANISM: Artificial Sequence
<220> FEATURE:
<223> OTHER INFORMATION: artificial primer

<400> SEQUENCE: 44
gtgctggtgc ccgcgatcgg gccccttgct gagcaccgt                           39

<210> SEQ ID NO 45
<211> LENGTH: 39
<212> TYPE: DNA
<213> ORGANISM: Artificial Sequence
<220> FEATURE:
<223> OTHER INFORMATION: artificial primer

<400> SEQUENCE: 45
acggtgctca gcaaggggcc cgatcgcggg caccagcac                           39

<210> SEQ ID NO 46
<211> LENGTH: 36
<212> TYPE: DNA
<213> ORGANISM: Artificial Sequence
<220> FEATURE:
<223> OTHER INFORMATION: artificial primer

<400> SEQUENCE: 46
tattctatca agcttcacga gatcggcacc gatcag                              36

<210> SEQ ID NO 47
<211> LENGTH: 36
<212> TYPE: DNA
<213> ORGANISM: Artificial Sequence
<220> FEATURE:
<223> OTHER INFORMATION: artificial primer

<400> SEQUENCE: 47
agatcatagg taccgatcaa cccgatcgcg gcgtgg                              36

<210> SEQ ID NO 48
<211> LENGTH: 36
<212> TYPE: DNA
<213> ORGANISM: Artificial Sequence
<220> FEATURE:
<223> OTHER INFORMATION: artificial primer

<400> SEQUENCE: 48
cttattatgg taccctcgtc ggtccagcgc agcagc                              36

<210> SEQ ID NO 49
<211> LENGTH: 37
<212> TYPE: DNA
```

```
<213> ORGANISM: Artificial Sequence
<220> FEATURE:
<223> OTHER INFORMATION: artificial primer

<400> SEQUENCE: 49
tagataatgc ggccgccggt gtgtaggtgt tgaagtc                              37

<210> SEQ ID NO 50
<211> LENGTH: 34
<212> TYPE: DNA
<213> ORGANISM: Artificial Sequence
<220> FEATURE:
<223> OTHER INFORMATION: artificial primer

<400> SEQUENCE: 50
ggggttaatt aacatgagcg gcgagacaac cagg                                 34

<210> SEQ ID NO 51
<211> LENGTH: 26
<212> TYPE: DNA
<213> ORGANISM: Artificial Sequence
<220> FEATURE:
<223> OTHER INFORMATION: artificial primer

<400> SEQUENCE: 51 gggggatcc cgaggcgtgc aacccg                                           26

<210> SEQ ID NO 52
<211> LENGTH: 6
<212> TYPE: PRT
<213> ORGANISM: Artificial Sequence
<220> FEATURE:
<223> OTHER INFORMATION: amino acid motif

<400> SEQUENCE: 52

Arg Tyr Tyr Glu Asp Leu
 1               5

<210> SEQ ID NO 53
<211> LENGTH: 10
<212> TYPE: PRT
<213> ORGANISM: Artificial Sequence
<220> FEATURE:
<223> OTHER INFORMATION: amino acid motif
<220> FEATURE:
<221> NAME/KEY: VARIANT
<222> LOCATION: 3, 4, 5, 7, 8, 9
<223> OTHER INFORMATION: Xaa = Any Amino Acid
<220> FEATURE:
<221> NAME/KEY: VARIANT
<222> LOCATION: (1)...(10)
<223> OTHER INFORMATION: Xaa = Any Amino Acid
<220> FEATURE:
<221> NAME/KEY: VARIANT
<222> LOCATION: (1)...(10)
<223> OTHER INFORMATION: Xaa = Any Amino Acid
<220> FEATURE:
<221> NAME/KEY: VARIANT
<222> LOCATION: (1)...(10)
<223> OTHER INFORMATION: Xaa = Any Amino Acid

<400> SEQUENCE: 53

Cys Cys Xaa Xaa Xaa Lys Xaa Xaa Xaa Leu
 1               5                  10

<210> SEQ ID NO 54
<211> LENGTH: 4
<212> TYPE: PRT
<213> ORGANISM: Artificial Sequence
```

```
<220> FEATURE:
<223> OTHER INFORMATION: amino acid motif
<220> FEATURE:
<221> NAME/KEY: VARIANT
<222> LOCATION: 2, 3
<223> OTHER INFORMATION: Xaa = Any Amino Acid
<220> FEATURE:
<221> NAME/KEY: VARIANT
<222> LOCATION: (1)...(4)
<223> OTHER INFORMATION: Xaa = Any Amino Acid
<220> FEATURE:
<221> NAME/KEY: VARIANT
<222> LOCATION: (1)...(4)
<223> OTHER INFORMATION: Xaa = Any Amino Acid
<220> FEATURE:
<221> NAME/KEY: VARIANT
<222> LOCATION: (1)...(4)
<223> OTHER INFORMATION: Xaa = Any Amino Acid

<400> SEQUENCE: 54

Cys Xaa Xaa Cys
 1

<210> SEQ ID NO 55
<211> LENGTH: 36
<212> TYPE: DNA
<213> ORGANISM: Artificial Sequence
<220> FEATURE:
<223> OTHER INFORMATION: synthetic primer

<400> SEQUENCE: 55
tattctatca agcttcacga gatcggcacc gatcag                                36

<210> SEQ ID NO 56
<211> LENGTH: 36
<212> TYPE: DNA
<213> ORGANISM: Artificial Sequence
<220> FEATURE:
<223> OTHER INFORMATION: synthetic primer

<400> SEQUENCE: 56
agatcatagg taccgatcaa cccgatcgcg gcgtgg                                36

<210> SEQ ID NO 57
<211> LENGTH: 36
<212> TYPE: DNA
<213> ORGANISM: Artificial Sequence
<220> FEATURE:
<223> OTHER INFORMATION: synthetic primer

<400> SEQUENCE: 57
cttattatgg taccctcgtc ggtccagcgc agcagc                                36

<210> SEQ ID NO 58
<211> LENGTH: 37
<212> TYPE: DNA
<213> ORGANISM: Artificial Sequence
<220> FEATURE:
<223> OTHER INFORMATION: synthetic primer

<400> SEQUENCE: 58
tagataatgc ggccgccggt gtgtaggtgt tgaagtc                               37

<210> SEQ ID NO 59
<211> LENGTH: 21
<212> TYPE: DNA
<213> ORGANISM: Artificial Sequence
<220> FEATURE:
<223> OTHER INFORMATION: exemplary target sequence
```

```
<400> SEQUENCE: 59
gcgcgaaata ctcactcgag g                                            21

<210> SEQ ID NO 60
<211> LENGTH: 22
<212> TYPE: DNA
<213> ORGANISM: Artificial Sequence
<220> FEATURE:
<223> OTHER INFORMATION: exemplary query sequence

<400> SEQUENCE: 60
tatagcccta ccactagagt cc                                           22
```

What is claimed is:

1. A method of increasing an immune response to a pathogenic mycobacterium in a host, comprising administering to the host an immunogenic composition, wherein said composition comprises a genetically modified mycobacterium, wherein said genetically modified mycobacterium comprises a functionally disabled sulfation pathway gene, such that said functionally disabled sulfation pathway gene does not direct expression of a functional sulfation pathway polypeptide, and wherein said genetically modified mycobacterium is avirulent.

2. The method of claim 1, wherein said administering is intramuscular.

3. The method of claim 1, wherein an immune response to a wild-type, virulent mycobacterium is induced.

4. The method of claim 3, wherein the virulent mycobacterium is of the same species as the genetically modified mycobacterium.

5. The method of claim 3, wherein the virulent mycobacterium is of a different species than the genetically modified mycobacterium.

6. The method of claim 1, wherein the cytotoxic T lymphocytes specific for mycobacterium are induced.

7. The method of claim 1, wherein said functionally disabled sulfation pathway gene is a functionally disabled adenylyl phosphosulfate reductases gene.

8. The method of claim 1, wherein said functionally disabled sulfation pathway gene is a functionally disabled adenylyl phosphosulfate kinase gene.

9. The method of claim 1, wherein said functionally disabled sulfation pathway gene is a functionally disabled sulfotransferase gene.

10. The method of claim 1, wherein said functionally disabled sulfation pathway gene is a functionally disabled ATP sulfurylase.

11. The method of claim 1, wherein said functionally disabled sulfation pathway gene is a functionally disabled 3'-phosphoadenosine-5'-phosphosulfate reductase.

12. The method of claim 1, wherein the pathogenic mycobacterium is *Mycobacterium tuberculosis,* and wherein the genetically modified mycobacterium is a genetically modified *Mycobacterium tuberculosis.*

13. The method of claim 1, wherein the pathogenic mycobacterium is *Mycobacterium tuberculosis,* and wherein the genetically modified mycobacterium is a genetically modified *Mycobacterium bovis.*

* * * * *